(12) United States Patent
Bowen et al.

(10) Patent No.: US 11,738,002 B2
(45) Date of Patent: Aug. 29, 2023

(54) METHODS OF TREATING NEUROLOGICAL AND PSYCHIATRIC DISORDERS

(71) Applicant: Sunovion Pharmaceuticals Inc., Marlborough, MA (US)

(72) Inventors: Carrie A. Bowen, Uxbridge, MA (US); Seth Cabot Hopkins, Northborough, MA (US); Colleen M. Synan, Townsend, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 26 days.

(21) Appl. No.: 17/228,796

(22) Filed: Apr. 13, 2021

(65) Prior Publication Data

US 2021/0315859 A1  Oct. 14, 2021

Related U.S. Application Data

(60) Provisional application No. 63/039,722, filed on Jun. 16, 2020, provisional application No. 63/009,595, filed on Apr. 14, 2020.

(51) Int. Cl.
*A61K 31/381* (2006.01)
*A61P 25/18* (2006.01)

(52) U.S. Cl.
CPC ............ *A61K 31/381* (2013.01); *A61P 25/18* (2018.01)

(58) Field of Classification Search
CPC ............................. A61K 31/381; A61P 25/18
USPC ........................................................ 514/443
See application file for complete search history.

(56) References Cited

U.S. PATENT DOCUMENTS

| | | | |
|---|---|---|---|
| 4,021,451 A | 5/1977 | Dobson et al. | |
| 4,021,452 A | 5/1977 | Floyd, Jr. | |
| 4,036,842 A | 7/1977 | Dobson et al. | |
| 4,127,665 A | 11/1978 | Sarges et al. | |
| 4,337,343 A | 6/1982 | Maillard et al. | |
| 5,532,233 A | 7/1996 | Weber et al. | |
| 6,262,044 B1 | 7/2001 | Moller et al. | |
| 6,313,309 B1 | 11/2001 | Baxter et al. | |
| 7,019,026 B1 | 3/2006 | Andersen et al. | |
| 8,710,245 B2* | 4/2014 | Shao .................. A61P 25/16 | 549/50 |
| 9,351,954 B2 | 5/2016 | Shao et al. | |
| 10,085,968 B2 | 10/2018 | Shao et al. | |
| 10,815,249 B2 | 10/2020 | Bauer et al. | |
| 10,894,033 B2 | 1/2021 | Shao et al. | |
| 11,129,807 B2 | 9/2021 | Hopkins et al. | |
| 11,440,921 B2 | 9/2022 | Bauer et al. | |
| 2002/0049223 A1 | 4/2002 | Elmore et al. | |
| 2004/0180883 A1 | 9/2004 | Gilmore | |
| 2004/0220402 A1 | 11/2004 | Chow et al. | |
| 2005/0075366 A1 | 4/2005 | Heidelbaugh et al. | |
| 2005/0187281 A1 | 8/2005 | Hinze et al. | |
| 2006/0047127 A1 | 3/2006 | Arjona | |
| 2006/0148872 A1 | 7/2006 | Chow et al. | |
| 2007/0072926 A1 | 3/2007 | Chow et al. | |
| 2007/0154534 A1 | 7/2007 | Sheitman et al. | |
| 2008/0081910 A1 | 4/2008 | Sabb et al. | |
| 2008/0113961 A1 | 5/2008 | Nishi et al. | |
| 2008/0255239 A1 | 10/2008 | Chow et al. | |
| 2009/0318690 A1 | 12/2009 | Sasaki et al. | |
| 2010/0035887 A1 | 2/2010 | Ricciardi | |
| 2012/0295881 A1 | 11/2012 | Lange et al. | |
| 2019/0125722 A1 | 5/2019 | Shao et al. | |
| 2019/0256525 A1 | 8/2019 | Bauer et al. | |
| 2020/0129477 A1 | 4/2020 | Hopkins et al. | |
| 2020/0179336 A1 | 6/2020 | Hopkins | |
| 2021/0008030 A1 | 1/2021 | Blum | |
| 2021/0053983 A1 | 2/2021 | Bauer et al. | |
| 2021/0267938 A1 | 9/2021 | Shao et al. | |
| 2022/0062229 A1 | 3/2022 | Hopkins et al. | |

(Continued)

FOREIGN PATENT DOCUMENTS

| | | |
|---|---|---|
| AU | 2010325925 A1 | 6/2011 |
| AU | 2016200448 A1 | 2/2016 |

(Continued)

OTHER PUBLICATIONS

International Search Report and Written Opinion in International Application No. PCT/US2021/026953, 12 pages dated Jul. 6, 2021.

(Continued)

*Primary Examiner* — Yevgeny Valenrod
(74) *Attorney, Agent, or Firm* — Heslin Rothenberg Farley & Mesiti P.C.

(57) ABSTRACT

The present disclosure relates to methods of treating neurological or psychiatric diseases or disorders, such as schizophrenia. Compound 1, or a pharmaceutically acceptable salt thereof, is an antipsychotic agent with a non-D2 mechanism of action. Adverse events associated with antipsychotic agents that target the D2 dopamine receptor can be reduced by treating disorders with Compound 1, or a pharmaceutically acceptable salt thereof.

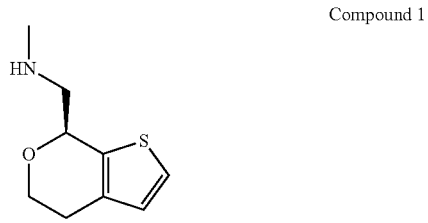

Compound 1

21 Claims, 32 Drawing Sheets

(56) References Cited

U.S. PATENT DOCUMENTS

| | | |
|---|---|---|
| 2022/0387382 A1 | 12/2022 | Shao et al. |
| 2022/0402937 A1 | 12/2022 | Bauer et al. |

FOREIGN PATENT DOCUMENTS

| | | |
|---|---|---|
| CA | 2031684 A1 | 6/1991 |
| CA | 2781716 A1 | 6/2011 |
| CN | 1300291 A | 6/2001 |
| CN | 101353321 A | 1/2009 |
| CN | 101759710 A | 6/2010 |
| CN | 102731574 A | 10/2012 |
| CN | 104193761 A | 12/2014 |
| DE | 3827727 A1 | 2/1990 |
| DE | 4104257 A1 | 8/1992 |
| EP | 333427 A1 | 9/1989 |
| EP | 366327 A1 | 5/1990 |
| EP | 0368175 A1 | 5/1990 |
| EP | 370732 A2 | 5/1990 |
| EP | 416740 A2 | 3/1991 |
| EP | 431945 A2 | 6/1991 |
| EP | 483647 A1 | 5/1992 |
| EP | 0518805 A1 | 12/1992 |
| EP | 555824 A1 | 8/1993 |
| EP | 574313 A1 | 12/1993 |
| EP | 600836 A2 | 6/1994 |
| EP | 745598 A1 | 12/1996 |
| EP | 1634873 A1 | 3/2006 |
| EP | 1829869 A1 | 9/2007 |
| EP | 1982714 A1 | 10/2008 |
| EP | 1982987 A1 | 10/2008 |
| EP | 2377850 A1 | 10/2011 |
| FR | 2875230 A1 | 3/2017 |
| JP | 54109975 A | 8/1979 |
| JP | S567772 A | 1/1981 |
| JP | 2243691 A | 9/1990 |
| JP | 4009367 A | 1/1992 |
| JP | 03163068 B2 | 5/2001 |
| JP | 03223277 B2 | 10/2001 |
| JP | 2002179678 A | 6/2002 |
| JP | 2003261566 A | 9/2003 |
| JP | 2004269449 A | 9/2004 |
| JP | 2005145859 A | 6/2005 |
| JP | 2005523925 A | 8/2005 |
| JP | 2006117568 A | 5/2006 |
| JP | 2008530229 A | 8/2008 |
| JP | 2009505948 A | 2/2009 |
| JP | 2015227348 A | 12/2015 |
| JP | 6333382 B2 | 5/2018 |
| MX | 2012006326 A | 10/2012 |
| RU | 2128649 C1 | 4/1999 |
| SG | 181498 A1 | 7/2012 |
| WO | 9108205 A1 | 6/1991 |
| WO | 9203434 A1 | 3/1992 |
| WO | 9215592 A1 | 9/1992 |
| WO | 9400441 A1 | 1/1994 |
| WO | 9604287 A1 | 2/1996 |
| WO | 9946237 A1 | 9/1999 |
| WO | 9946267 A1 | 9/1999 |
| WO | 0023445 A1 | 4/2000 |
| WO | 2000023445 | 4/2000 |
| WO | 0035915 A1 | 6/2000 |
| WO | 2000035915 | 6/2000 |
| WO | 2000043397 A1 | 7/2000 |
| WO | 2000068230 A1 | 11/2000 |
| WO | 0117516 A2 | 3/2001 |
| WO | 0119831 A1 | 3/2001 |
| WO | 2001017516 | 3/2001 |
| WO | 2001019831 | 3/2001 |
| WO | 0132655 A2 | 5/2001 |
| WO | 2001032610 A1 | 5/2001 |
| WO | 0212189 A1 | 2/2002 |
| WO | 2002012189 | 2/2002 |
| WO | 2002022614 A1 | 3/2002 |
| WO | 02096908 A1 | 12/2002 |
| WO | 02102387 A1 | 12/2002 |
| WO | 02102793 A2 | 12/2002 |
| WO | 03006455 A1 | 1/2003 |
| WO | 03035065 A1 | 5/2003 |
| WO | 03092374 A2 | 11/2003 |
| WO | 2004004726 A1 | 1/2004 |
| WO | 2004035812 A2 | 4/2004 |
| WO | 2004066912 A2 | 8/2004 |
| WO | 2004078723 A1 | 9/2004 |
| WO | 2004082687 A1 | 9/2004 |
| WO | 2004087680 A1 | 10/2004 |
| WO | 2005072412 A2 | 8/2005 |
| WO | 2005073236 A2 | 8/2005 |
| WO | 2005087779 A1 | 9/2005 |
| WO | 2006014135 A1 | 2/2006 |
| WO | 2006014136 A1 | 2/2006 |
| WO | 2006015259 A2 | 2/2006 |
| WO | 2006030124 A1 | 3/2006 |
| WO | 2006053274 A2 | 5/2006 |
| WO | 2006089053 A2 | 8/2006 |
| WO | 2007001939 A1 | 1/2007 |
| WO | 2007002681 A2 | 1/2007 |
| WO | 2007006546 A1 | 1/2007 |
| WO | 2007095586 A2 | 8/2007 |
| WO | 2007098961 A1 | 9/2007 |
| WO | 2007102999 A2 | 9/2007 |
| WO | 2007126041 A1 | 11/2007 |
| WO | 2008042422 A2 | 4/2008 |
| WO | 2008048981 A2 | 4/2008 |
| WO | 2008058342 A1 | 5/2008 |
| WO | 2008155132 A1 | 12/2008 |
| WO | 2009009550 A1 | 1/2009 |
| WO | 2009067202 A1 | 5/2009 |
| WO | 2009068467 A1 | 6/2009 |
| WO | 2009072621 A1 | 6/2009 |
| WO | 2009085256 A1 | 7/2009 |
| WO | 2010053583 A2 | 5/2010 |
| WO | 2010092180 A1 | 8/2010 |
| WO | 2010092181 A1 | 8/2010 |
| WO | 2011036889 A1 | 3/2011 |
| WO | 2011060035 A1 | 5/2011 |
| WO | 2011060217 A1 | 5/2011 |
| WO | 2011069063 A2 | 6/2011 |
| WO | 2011081205 A1 | 7/2011 |
| WO | 2011133729 A2 | 10/2011 |
| WO | 2012016879 A1 | 2/2012 |
| WO | 2012020133 A1 | 2/2012 |
| WO | 2012122340 A1 | 9/2012 |
| WO | 2013010453 A1 | 1/2013 |
| WO | 2018151861 | 8/2018 |
| WO | 2018151861 A1 | 8/2018 |
| WO | 2019161236 A1 | 8/2019 |
| WO | 2019161238 A1 | 8/2019 |
| WO | 2020118032 A1 | 6/2020 |
| WO | 2021211489 A1 | 10/2021 |
| WO | 2022060758 A1 | 3/2022 |
| ZA | 9102744 A | 2/1992 |

OTHER PUBLICATIONS

CAS Registry No. 1082475-31-7, 1 page. Dec. 9, 2008.
CAS Registry No. 924976-20-5, 1 page. Mar. 6, 2007.
CAS Registry No. 138993-75-6, 4 pages. Feb. 14, 1992.
Balbach et al., "Pharmaceutical Evaluation of Eady Development Candidates" the 100 mg-approach, International Journal of Pharmaceutics, vol. 275, pp. 1-12. Jan. 27, 2004.
Singhal et al., "Drug Polymorphism and Dosage Form Design: A Practical Perspective", Advanced Drug Delivery Reviews, vol. 56, pp. 335-347. 2004.
Synan et al., "Ulotaront, a Novel TAAR1 Agonist with 5-HT1A Agonist Activity, Lacks Abuse Liability and Attenuates Cocaine Cue-Induced Relapse in Rats", Drug and Alcohol Dependence, 39 pages. 2021.
Correll et al., "Safety and Effectiveness of Ulotaront (SEP-363856) in Schizophrenia: Results of a 6-month, Open-Label Extension Study", NPJ Schizophrenia, vol. 7, No. 63, 9 pages. 2021.
Dedic et al., "Therapeutic Potential of TAAR1 Agonists in Schizophrenia: Evidence from Preclinical Models and Dlinical Studies",

(56) References Cited

OTHER PUBLICATIONS

International Journal of Molecular Sciences, vol. 22, 23 pages. 2021.
Heffernan et al., "Ulotaront: A TAAR1 Agonist for the Treatment of Schizophrenia", ACS Medical Chemistry Letters, vol. 13, pp. 92-98. 2022.
Raab et al., "Incretin-like Effects of Small Molecule Trace Amine-Associated Receptor 1 Agonists", Molecular Metabolism, vol. 5, pp. 47-56. 2016 (available online Nov. 1, 2015).
Revel et al., "A New Perspective for Schizophrenia: TAAR1 Agonists Reveal Antipyschotic- and Antidepressant-like Activity, Improve Cognition and Control BodyWeight", Molecular Psychiatry, vol. 18, pp. 543-556. 2013.
Hopkins et al., "Depicting Safety Profile of TAAR1 Agonist Ulotaront Relative to Reactions Anticipated for a Dopamine D2-Based Pharmacological Class in FAERS", Clinical Drug Investigation, vol. 41, pp. 1067-1073. 2021.
Koblan et al., "Understanding Negative Symptoms in Clinical Trials of Acute Schizophrenia", Neuropsychopharmacology, vol. 46, 1 page. 2021.
Krogsgaard-Larsen et al. "Textbook of Drug Design and Discovery", Taylor & Francis. Apr. 2002.
Langa et al. "Generation and Phenotypic Analysis of Sigma Receptor Type 1 (Sigma1) Knockout Mice", European Journal of Neuroscience, vol. 18, pp. 2188-2196. 2003.
Lowry et al. "Protein Measurement with the Folin Phenol Reagent", Journal Bio. Chem., vol. 193, p. 265. 1951.
Mahableshwarkar et. al., "Replication of a statistical method to reduce pseudospecificity and enhance understanding of score changes among PANSS factors", poster presented at meeting for Int. Soc. For CNS clinical trials and methodology, presented between Aug. 31-2017-Sep. 2, 2017. 2017.
Maier et al., "Novel Spiropiperidines as Highly Potent and Subtype Selective σ-Receptor Ligands. Part 1", Journal Med. Chem., vol. 45, pp. 438-448. 2002.
Maier et al., "Novel σ Receptor Ligands. Part 2. SAR of Spiro[[2]benzopyran-1,4'-piperidines] and Spiro [[2] benzofuran-1,4'-piperidines] with Carbon Substituents in Position 3", Journal Med. Chem., vol. 45, pp. 4923-4930. 2002.
Marcus et al. "The Efficacy and Safety of Aripiprazole as Adjunctive Therapy in Major Depressive Disorder. A second Multicenter Randomized, Double-Blind, Placebo-Controlled Study", Journal of Clinical Psychopharmacology, vol. 28, No. 2, pp. 15-165. Apr. 2008.
Mashkovskiy "Drugs", Moscow, NewWave, LLC, vol. 1, p. 11 with translation. 2002.
Moreno et al. "Preclinical Models of Antipsychotic Drug Action", International Journal of Neuropsychopharmacology, vol. 16, pp. 2131-2144. Jun. 10, 2013.
Nordquist et al. "Effects of Aripiprazole/OPC-14597 on Motor Activity, Pharmacological Models of Psychosis, and Brain Activity in Rats", Neuropharmacology, vol. 54, pp. 405-416. 2008.
Pittenger et al. "The NMDA Receptor as a Therapeutic Target in Major Depressive Disorder", CNS & Neurological Disorders—Drug Targets, vol. 6, No. 2, pp. 101-115. Feb. 19, 2007.
Poola et al. "Pharmacokinetics, Safety, and Tolerability of Sep-363856 in Healthy Adult Male Subjects and in Adult Patients With Schizophrenia Following Oral Administration", American College of Clinical Pharmacology, Poster. Sep. 2018.
PubChem CID 4878038 (search date Feb. 22, 2019). Sep. 17, 2005.
PubChem CID 4878041 (search date Feb. 22, 2019). Sep. 17, 2005.
Quirion et al. "A Proposal for the Classification of Sigma Binding Sites", Trends Pharmacol. Sci., vol. 13, pp. 86-86. Mar. 1992.
Radesca "Synthesis and Receptor Binding Enantiomeric N-Substituted cis-N-[2-(3,4-Dichlorophenyl)ethyl]-2-(1-pyrrolidiny) Cyclohexylamines as High-Affinity O' Receptor Ligands", Journal Med. Chem., vol. 34, pp. 3065-3074. 1991.
Registry (STN) [online] CAS Registry No. 933704-21-3, 1 page. Apr. 30, 2007.
Ross et al., "α2 Adrenoceptor Agonists as Potential Analgesic Agents. 2. Discovery of 4 (4-Imidazo) 1,3-dimethyl 6,7-dihydro-thianaphthene as a High-Affinity Ligand for the α2D Adrenergic Receptor", J. Med. Chem., vol. 43, pp. 1423-1426. 2000.
Schmitz et al. "Hippocampal Neuron Loss Exceeds Amyloid Plaque Load in a Transgenic Mouse Model of Alzheimer's Disease", American Journal of Pathology, vol. 164, p. 1495. 2004.
Schow "Novel Sigma Receptor Ligands 2", Bioorganic and Medicinal Chemistry Letters, No. 2, pp. 221-224. 1993.
Sheitman et al., "Secretin for refractory schizophrenia" Elsevier, Science Direct, Schizophrenia Research 66, pp. 177-181. 2004.
Snyder et al. "Receptor Mechanisms in Antipsychotic Drug Action: Focus on Sigma Receptors", Journal Neuropsychiatry, vol. 1, pp. 7-15. 1989.
Stanetty et al., "Heterocyclische Spiroverbindungen Spiroverbindungen: Spiro [benzo[b]thiophen-4(5H),3'-pyrrolidine]". Arch. Pharm. vol. 317, pp. 168-176. 1984.
Swerdlow et al. "Seroquel Restores Sensorimotor Gating in Phencyclidine—Treated Rats", Journal of Pharmacology and Experimental Therapeutics, vol. 279, No. 3, pp. 1290-1299. Dec. 1996.
Torrado et al. "Novel Selective and Potent 5-HT Reuptake Inhibitors with 5-HT1D Antagonist Activity: Chemistry and Pharmacological Evaluation of a Series of Thienopyran Derivatives", Bioorganic & Medicinial Chemistry, 12(20), pp. 5277-5295. Oct. 15, 2004.
Trehan "A New Synthesis of 13-aza-18-nor-17-oxo-A-nor-3-thiaestra-1,5(10), 9(11)-triene", retrieved from STN Database Accession No. 1986:225089 and Indian Journal of Chemistry, Section 6: Organic Chemistry Including Medicinal Chemistry, vol. 24B(6), pp. 659-661. 1985.
Trehan "Synthesis of 2, 3, 13-Triaza-18-nor-17-oxo-3-phenyl-A-nor-estra-1,5(10), 9(11)-triene & 2, 3,13-Triaza-7,7-dimethyl-18-nor-17-oxo-3-phenyl-A-nor-estra-1,5(10), 9(11)-triene", Indian Journal of Chemistry, vol. 19B, pp. 243-245. 1980.
Vecchietti et al. "(1 S)-1-(Aminomethyl)-2-(Arylacetyl)-1,2,3,4-tetrahydroisoquinoline and Heterocycle-Condensed Tetrahydropyridine Derivatives: Members of a Novel Class of Very Potent K Opioid Analgesics", Journal of Medicinal Chemistry, vol. 34, No. 8, pp. 2624-2633. 1991.
Walker: Pharmacological Reviews, "Sigma Receptors: Biology and Function", vol. 42, No. 4, pp. 355-402. 1990.
Written Opinion in International Application No. PCT/US2018/000078. dated May 25, 2018.
Written Opinion in International Application No. PCT/US2019/018263. dated Apr. 2, 2019.
Written Opinion in International Application No. PCT/US2019/064646. dated Mar. 9, 2020.
Bakshi et al. "Antagonism of Phencyclidine-Induced Deficits in Prepulse Inhibition by the Putative Atypical Antipsychotic Olanzapine", Psychopharmacology, vol. 122, No. 2, pp. 198-201. Nov. 1995.
Berardi et al. "4-(Tetralin-1-yl)-and 4-(Naphthalen-1-yl) alkyl Derivatives Ligands with Agonist s2 Activity", Journal of Medicinal Chemistry, American Chemical Society, vol. 47, No. 9, pp. 2308-2317. 2004.
Berardi et al. "A Multireceptorial Binding Reinvestigation on an Extended Class of s Ligands: N-[w-(Indan-1-yl and Tetralin-1-yl)alkyl] Derivatives of 3,3-Dimethylpiperidine Reveal High Affinities Towards s1 and EBP Sites", Bioorganic & Medicinal Chemistry, vol. 9, No. 5, pp. 1325-1335. 2001.
Berardi et al. "Novel Potent s1 Ligands: N-[w-(Tetralin-1-yl)alkyl] piperidine Derivatives" Journal of Medicinal Chemistry, American Chemical Society, vol. 39, No. 21, pp. 4255-4260. 1996.
Caira "Crystalline Polymorphism of Organic Compounds" Topics in Current Chemistry, vol. 198, pp. 163-208. Jan. 1, 1998.
Chihara et al. "Preparation of Benzothiophene Derivatives as Blood Platelet Aggregation Inhibitors", Retrieved from STN Database Accession No. 1992:128652 and JP03223277A, Yoshitomi Pharmaceutical Industries Ltd. Oct. 2, 1991.
Corbera et al. "A Medicinal-Chemistry-Guided Approach to Selective and Druglike Sigma 1 Ligands", Chemmedchem, vol. 1, No. 1, pp. 140-154. Jan. 2006.
Correll et al. "Safety and Effectiveness of SEP-363856 in Schizophrenia: Results of a 6-Month, Open-Label Extension Study", American College of Neuropsychopharmacology, Poster. Dec. 2019.

(56) References Cited

OTHER PUBLICATIONS

Datta et al., "Studies in Sulphur Heterocycles. Part 5. Further Use of 6,7-Dihydribenzo[b]thiphen-4[5H]-one in the Synthesis of Substituted Benzo[b]thiophene Derivatives", J. Chem. Research (S), pp. 72-73. 1988.

Deakin et al. "A Phase 1 Functional Neuroimaging Study of SEP-363856 in Healthy Volunteers With High or Low Schizotype", American College of Neuropsychopharmacology, Poster. Dec. 2016.

Dedic et al. "SEP-363856, A Novel Psychotropic Agent With a Unique, Non-D2 Receptor Mechanism of Action", The Journal of Pharmacology and Experimental Therapeutics, Manuscript. Oct. 2019.

Dedic et al. "The Novel, Non-D2 Psychotropic Agent SEP-363856 Modulates Presynaptic Dopamine Function in Mice", American College of Neuropsychopharmacology, Poster. Dec. 9, 2019.

Dehaven-Hudkins et al. "Characterization of the Binding of [3H](+)pentazocine to sigma Recognition Sites in Guinea Pig Brain" Eur. Journal Pharmacol, vol. 277, pp. 371-378. 1992.

Devani et al., "Synthesis of 2-Aminothiophenes & Thieno[2,3-d]pyrimidines", Indian Journal of Chemistry, vol. 14B, pp. 357-360. May 1976.

Extended European Search Report for EP Application No. 10835185.9, pp. 1-15. dated Apr. 4, 2013.

Frohlich et al., "A Novel Synthesis of 3,3-(Spiro)Substituted Azetidines", Heterocycles, vol. 37, No. 3, pp. 1897-1891. 1994.

Fujima et al. "Synthesis of (S)-3-(N-Methylamino)-1-(2-thienyl)propan-1-ol: Revisiting Eli Lilly's Resolution-Racemization-Recycle Synthesis of Duloxetine for its Robust Processes", Organic Process Research and Development, vol. 10, No. 5, pp. 905-913. Jan. 1, 2006.

Ghaemi et al. "Does Olanzapine have Antidepressant Properties? A Retrospective Preliminary Study", Bipolar Disorders, vol. 2, pp. 196-199. 2000.

Ghasemi et al. "The Role of NMDA Receptors in the Pathophysiology and Treatment of Mood Disorders", Neuroscience and Biobehavioral Reviews, vol. 47, pp. 336-358. Sep. 16, 2014.

Gleason et al. "Blockade of Phencyclidine-Induced Hyperlocomotion by Olanzapine, Clozapine and Serotonin Receptor Subtype Selective Antagonists in Mice", Psychopharmacology, vol. 129, pp. 79-84. 1997.

Hanner et al. "Purification, Molecular Cloning, and Expression of the Mammalian Sigmal-Binding Site", Proc. Natl. Aca. Sci, vol. 93, pp. 8072-8077. 1996.

Hejl et al. "Prepulse Inhibition in Patients with Alzheimer's Disease", Neurobiology of Aging, vol. 25, p. 1045. 2004.

Hopkins et al. "Effects of SEP-363856 on Negative Symptoms in Schizophrenia: Analysis of an Acute, Placebo-Controlled Trial of a Novel Psychotropic Agent With No Dopamine-D2/5-Ht2a Antagonist Activity", American College of Neuropsychopharmacology, Poster. Dec. 2019.

Hopkins et al., "Transformed PANSS Factors Intended to Reduce Pseudospecificity Among Symptom Domains and Enhance Understanding of Symptom Change in Antipsychotic-Treated Patients With Schizophrenia", Schizophrenia Bulletin, vol. 44, No. 3, pp. 593-602. 2018.

Hopkins, "Improving the Specificity and Precision of PANSS Factors: One Approach to Facilitate Development of Novel Treatments in Schizophrenia", The International Society for CNS Clinical Trials and Methodology, (ISCTM) 14th Annual Scientific Meeting. Feb. 20, 2018.

Hopkins, "Transformed PANSS Factors Intended to Reduce Pseudospecificity Among Domains, Enhancing Understanding of Symptom Change in Antipsychotic—Treated Patients with Schizophrenia", The International Society for CNS Clinical Trials and Methodology (ISCTM) 13th Annual Scientific Meeting. Feb. 23, 2017.

International Search Report in International Application No. PCT/US2019/018263 dated Apr. 2, 2019.

International Search Report and Written Opinion issued in PCT/US2010/05884, 10 pages. dated Aug. 25, 2011.

International Search Report and Written Opinion issued in PCT/US2019/018265 dated Jun. 18, 2019.

International Search Report in International Application No. PCT/US2018/000078. dated May 25, 2018.

International Search Report in International Application No. PCT/US2019/064646. dated Mar. 9, 2020.

Jacobs et al. "1-Imidazolyl(alkyl)-Substituted Di- and Tetrahydroquinolines and Analogues: Syntheses and Evaluation of Dual Inhibitors of Thromboxane A2 Synthase and Aromatase", Journal of Medicinal Chemistry, vol. 43, No. 9, pp. 1841-1851. Apr. 12, 2000.

Kostin et al. "Lack of Hypocretin Attenuates Behavioral Changes Produced by Glutamatergic Activation of the Perifornical-Lateral Hypothalamic Area", Sleep, vol. 37, No. 5, pp. 1011-1020. 2014.

Jentsch et al., "The Neuropsychopharmacology of Phencyclidine: From NMDA Receptor Hypofunction to the Dopamine Hypothesis of Schizophrenia", Neuropsychopharmacology, vol. 20, No. 3, pp. 201-225. 1999.

Dobson et al. "Pyrano Heterocycles. I. The Syntheses of Isochromans and the Novel thieno[3,2-c]pyran, benzothieno[3,2-c]pyran, benzothieno[2,3-c]pyran, and pyrano[4,3-b] benzofuran Systems", Journal of Heterocyclic Chemistry, 12 (3), pp. 591-594. Jan. 1, 1975.

Jones et al. "SEP-0363856, A Novel Psychotropic Agent With a Unique, Non-D2 Mechanism of Action", European College of Neuropsychopharmacology, Poster. Sep. 2019.

Kapur et al. "NMDA Receptor Antagonist Ketamine and PCP Have Direct Effects on the Dopamine D2 and Serotonin 5-HT2 Receptors-Implications for Models of Schizophrenia", Molecular Psychiatry, vol. 7, pp. 837-844. 2002.

Karran et al. "The Amyloid Cascade Hypothesis for Alzheimer's Disease: an Appraisal for the Development of Therapeutics", Nature, vol. 10, p. 698. 2011.

Katsuki et al., "Excitotoxic Degeneration of Hypothalamic Orexin Neurons in Slice Culture", Neurobiology of Disease, vol. 15, pp. 61-69. 2004.

Kay et al., Schizophrenia Bulletin, vol. 13(2), pp. 261-276. 1987.

Koblan et al. "A Non-D2-Receptor-Binding Drug for the Treatment of Schizophrenia" The New England Journal of Medicine, vol. 382, No. 16, pp. 1497-1506. Apr. 16, 2020.

Koblan et al. "A Phase 1 Open Label Safety and Tolerability Study of Sep-363856, A Novel Non-D2 Mechanism of Action Molecule, in Patients With Schizophrenia", American College of Neuropsychopharmacology, Poster Dec. 2016.

Koblan et al. "Efficacy and Safety of Sep-363856 in the Treatment of Schizophrenia: A 4-Week, Randomized, Placebo-Controlled Trial of a Novel Compound With a Non-D2 Mechanism of Action", American College of Neuropsychopharmacology, Poster. Dec. 2018.

Koblan et al. "Efficacy and Safety of SEP-363856, A Novel Non-D2 Agent, in the Treatment of Schizophrenia: A 4-Week, Randomized, Placebo-Controlled Trial", European College of Neuropsychopharmacology, Poster. Sep. 2019.

Koblan et al. "Efficacy And Safety of SEP-363856, A Novel Psychotropic Agent With a Non-D2 Mechanism of Action, in the Treatment of Schizophrenia: A 4-Week, Randomized, Placebo-Controlled Trial", American Psychiatric Association, Poster. Oct. 2019.

Koblan et al. "Efficacy and Safety of SEP-363856, A Novel Psychotropic Agent With a Non-D2 Mechanism of Action, in the Treatment of Schizophrenia: A 4-Week, Randomized, Placebo-Controlled Trial", US Psychiatric and Mental Health Congress, Poster. May 2019.

Koblan et al. "Efficacy and Safety of SEP-363856, A Novel Psychotropic Agent With a Non-D2 Mechanism of Action, in the Treatment of Schizophrenia: A Randomized, Placebo-Controlled Trial", Neuroscience Education Institute, Poster. Nov. 2019.

Koblan et al. "SEP-363856, A Novel Psychotropic Agent With a Non-D2 Mechanism of Action, For the Treatment of Schizophrenia", Schizophrenia International Research Society, Oral Presentation. Apr. 2019.

(56) References Cited

OTHER PUBLICATIONS

Koblan, "SEP-363856, A Candidate Antipsychotic and Antidepressant Compound With a Novel Non-D2 Mechanism of Action", Schizophrenia International Research Society, Oral Presentation Apr. 2018.

Galluppi et al., "Population Pharmacokinetic Analysis of Ulotaront in Subjects with Schizophrenia", CPT Pharmacometrics Syst Pharmacol, pp. 1-10. Jul. 22, 2021.

Synan et al., "Preclinical Abuse Liability Assessment of SEP-363856, A Compound with a Non-D2 Receptor Mechanism of Action", Poster, College on Problems of Drug Dependence. 2020.

Synan et al., "SEP-363856, A Novel TAAR1 Agonist, Lacks Abuse Liability in Preclinical Models and Attenuates Cocaine Cue-Induced Relapse in Rats", Poster, The American College of Neuropsychopharmacology. 2020.

Hopkins et al., "Characterization of Specific and Distinct Patient Types in Clinical Trials of Acute Schizophrenia Using an Uncorrelated PANSS Score Matrix Transform (UPSM)", Psychiatry Research, vol. 294, 7 pages. 2020.

Hopkins et al., "The Safety Profile of the TAAR1 Agonist, SEP-363856, is Distinct From Atypical Antipsychotics", Poster, American Psychiatric Association Annual Meeting. 2021.

Isaacson et al., "Efficacy and Safety of SEP-363856, A Non-D2-Receptor-Binding Drug With Antipsychotic Activity, in Patients with Parkinson's Disease Psychosis", American Academy of Neurology, Virtual Annual Meeting, 18 pages. 2021.

Koblan, "SEP-363856, A Novel Non-D2, TAAR1 Agonist for the Treatment of Schizophrenia: Current Development Status", American Society of Clinical Psychopharmacology, Annual Meeting, 15 pages. 2020.

Hopkins et al., "Effect of TAAR1/5-HT1A Agonist SEP-363856 on REM Sleep in Humans", Translational Psychiatry, vol. 11, No. 228, 10 pages. 2021.

Koblan, "SEP-363856: A Compound with a Non-D2 Receptor Mechanism of Action for the Treatment of Schizophrenia: Update", Schizophrenia International Research Society Annual Congress, Poster. 2020.

Kokkinou et al., "Reproducing the Dopamine Pathophysiology of Schizophrenia and Approaches to Ameliorate It: A Translational Imaging Study with Ketamine", Molecular Psychiatry, 15 pages. May 7, 2020.

Milanovic et al., "Measures of Cognition and Social Functioning in Schizophrenia Patients Receiving SEP-363856", Poster, Schizophrenia International Research Society Congress. 2020.

Begni et al. "Towards Novel Treatments for Schizophrenia: Molecular and Behavioural Signatures of the Psychotropic Agent SEP-363856", International Journal of Molecular Sciences, vol. 22, No. 4119, 19 pages. 2021.

Chen et al., "No Chiral Inversion for SEP-363856 in Humans by A Novel Chiral LC-MS/MS Analysis of Human Plasma from Clinical Trials", Poster, American Society for Mass Spectrometry. 2020.

Dworak, "SEP-363856: A Compound with a Non-D2 Receptor Mechanism of Action for the Treatment of Schizophrenia: Update", Poster, American Society of Clinical Psychopharmacology Annual Meeting. 2021.

Dworak et al., "Effects of SEP-363856, A Novel TAAR1 Agonist, on Negative Symptoms in Schizophrenia: Results Across an Initial Double-Blind Acute Study, and a 6-Month, Open-Label Extension Study", Poster, The American College of Neuropsychopharmacology 59th Annual Meeting. 2020.

Che, Encyclopedia of Psychological Counseling, Science and Technology Press, p. 293 Dec. 31, 2001.

Richelson et al., "Binding of Antipsychotic Drug to Human Brain Receptors Focus on Newer Generation Compounds", Life Sciences, vol. 68, pp. 29-39. 2000.

Siafis et al., "Antipsychotic Drugs: From Receptor-Binding Profiles to Metabolic Side Effects", Current Neuropharmacology, vol. 16, pp. 1210-1223. 2018.

Variankaval et al. "From Form to Function: Crystallization of Active Pharmaceutical Ingredients", AIChE Journal, vol. 54, No. 7, pp. 1682-1688. Jul. 2008.

Nazimek et al., "A Phase 1 Functional Neuroimaging Study of SEP-363856 in Healthy Volunteers with High or Low Schizotypy", ACNP 55th Annual Meeting, 3 pages. Nov. 4, 2014.

Hilfiker et al., "Relevance of Solid-State Properties for Pharmaceutical Products", Polymorphism: in the Pharmaceutical Industry, 19 pages. 2006.

International Search Report and Written Opinion in International Application No. PCT/US2022/076747, 14 pages. Jan. 13, 2023.

Chen et al., "Comparative Bioequivalence of Table and Capsule Formulations of Ulotaront and the Effect of Food on the Pharmacokinetics of the Tablet Form in Humans", Neurol Then, submitted online https://doi.org/10.1007/s40120-023-00459-8, 18 pages 2023.

Black et al., "Trace Amine—Associated Receptor 1 Agonists as Narcolepsy Therapeutics", Biological Psychiatry, vol. 82, pp. 623-633. Nov. 1, 2017.

Goonawardena et al., "Trace amine-associated receptor 1 agonism promotes wakefulness without impairment of cognition in Cynomolgus macaques", Neuropsychopharmacology, vol. 44, pp. 1485-1493. Apr. 6, 2019.

Gursahani et al., "Preclinical Pharmacology of Solriamfetol: Potential Mechanisms for Wake Promotion", Sleep, vol. 45, supplement 1, p. A239. 2022.

Nuvigil prescribing information, 25 pages. 2017.

Revel et al., "Trace Amine-Associated Receptor 1 Partial Agonism Reveals Novel Paradigm for Neuropsychiatric Therapeutics", Biol Psychiatry, vol. 72, pp. 934-942. 2012.

Schwartz et al., "Trace Amine—Associated Receptor 1 Regulates Wakefulness and EEG Spectral Composition", Neurospychopharmacology, vol. 42, pp. 1305-1314. 2017.

Self-Care/Narcolepsy, downloaded Mar. 20, 2023 from URL: https://healthysleep.med.harvard.edu/narcolepsy/treating-narcolepsy/self-care , 3 pages. 2023.

Sunosi prescribing information, 24 pages. 2019.

Tsukada et al., "A Randomized, Single-Dose, Crossover Study of the Effects of Ulotaront on Electrocardiogram Intervals in Subjects with Schizophrenia", Clinical Transl Sci., downloaded Mar. 30, 2023 from URL: https://ascpt. onlinelibrary.wiley.com/doi/epdf/10.1111/cts.13512, 12 pages. 2023.

\* cited by examiner

FIG. 18A
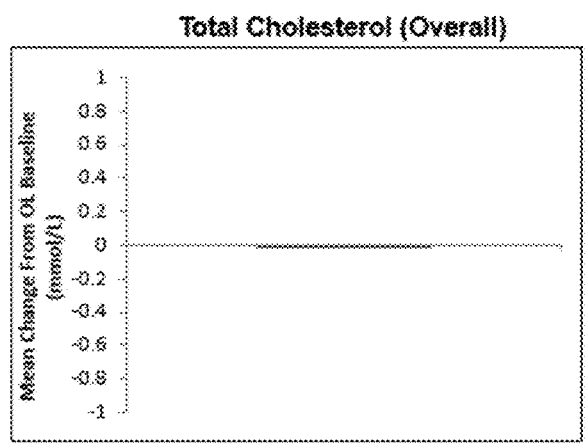
FIG. 18C
FIG. 18B
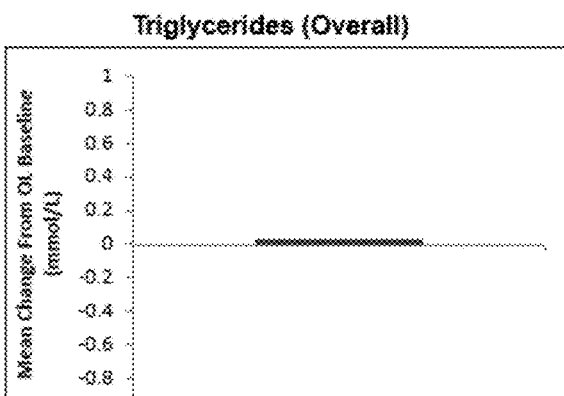
FIG. 18D

Time (Days) to Completion/Discontinuation from the First Dose in Study Example 1.2

Source: Lieberman et al., 2005 (CATIE study)

METHODS OF TREATING NEUROLOGICAL AND PSYCHIATRIC DISORDERS

CROSS REFERENCE TO RELATED APPLICATIONS

This application claims priority to U.S. Provisional Application No. 63/039,722 filed Jun. 16, 2020 and U.S. Provisional Application No. 63/009,595, filed Apr. 14, 2020, the contents of which are hereby incorporated by reference herein in their entirety.

TECHNICAL FIELD

The present disclosure relates to methods of treating neurological and psychiatric diseases and disorders.

BACKGROUND

The D2 dopamine receptor is a primary target for both typical and atypical antipsychotic agents. Wang et al. NATURE 555, 269-273 (2018). However, many drugs that target the D2 dopamine receptor cause serious or potentially life-threatening side effects. Wang et al. NATURE 555, 269-273 (2018). Despite decades of research on non-D2 mechanisms of action, developing non-D2 antipsychotic therapies that are both safe and effective has been challenging. Girgis et al., J. PSYCHIATRIC RES. (2018), https://doi.org/10.1016/j.jpsychires.2018.07.006. In particular, after performing a comprehensive review of literature relating to experimental treatments for schizophrenia, including 250 studies between 1970 to 2017 with glutamatergic, serotonergic, cholinergic, neuropeptidergic, hormone-based, dopaminergic, metabolic, vitamin/naturopathic, histaminergic, infection/inflammation-based, and otherwise miscellaneous mechanisms for treating schizophrenia, Girgis states, "Despite there being several promising [non-D2] targets, such as allosteric modulation of the NMDA and α7 nicotinic receptors, we cannot confidently state that any of the mechanistically novel experimental treatments covered in this review are definitely effective for the treatment of schizophrenia and ready for clinical use." Accordingly, there is a need for therapeutic agents having efficacy in treating neurological and psychiatric diseases and disorders (e.g., schizophrenia) with lower incidence of adverse events.

As disclosed herein, Compound 1 has received Breakthrough Therapy Designation from the United States Food and Drug Administration (FDA) as a novel agent for the treatment of people with schizophrenia. Breakthrough Therapy Designation is intended to expedite the development and review of drugs for serious or life-threatening conditions when preliminary clinical evidence indicates that the drug may demonstrate substantial improvement over available therapy on one or more clinically significant endpoints. The FDA granted Breakthrough Therapy Designation for Compound 1 based on pivotal, Phase 2 data from clinical trials disclosed herein.

SUMMARY

The present disclosure relates to methods of treating neurological and psychiatric diseases and disorders.

In some embodiments, provided is a method of treating a patient having a neurological or psychiatric disease or disorder, comprising orally administering to the patient Compound 1

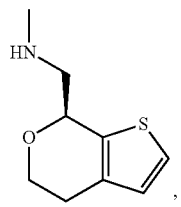

Compound 1 or a pharmaceutically acceptable salt thereof, in the evening or at night, or at about bedtime.

In some embodiments, provided is a method of treating a neurological or psychiatric disease or disorder in a patient, comprising administering to the patient a therapeutically effective amount of Compound 1

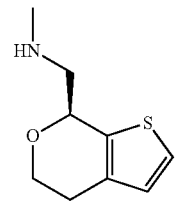

Compound 1 or a pharmaceutically acceptable salt thereof, in the evening or at night, or at about bedtime, wherein the method minimizes adverse events in the patient. In some embodiments, the method minimizes adverse events associated with antipsychotic agents with affinity to dopamine D2 receptors.

In some embodiments, provided is a method of treating a neurological or psychiatric disease or disorder in a patient, comprising administering to the patient a therapeutically effective amount of Compound 1, or a pharmaceutically acceptable salt thereof, in the evening or at night, or at about bedtime, wherein the method is substantially devoid of adverse events. In some embodiments, a risk of adverse events in the patient is about the same as or similar to placebo.

In some embodiments, provided is a method of treating a neurological or psychiatric disease or disorder in a patient, wherein the method is substantially devoid of adverse events of an antipsychotic agent having affinity to dopamine D2 receptors, comprising administering to the patient a therapeutically effective amount of an antipsychotic agent with no direct affinity to dopamine D2 receptors selected from Compound 1, or a pharmaceutically acceptable salt thereof, in the evening or at night, or at about bedtime.

In some embodiments, provided is a method of minimizing adverse events in a patient in need of treatment for a neurological or psychiatric disease or disorder, the method comprising administering to the patient a therapeutically effective amount of an antipsychotic agent with no direct affinity to dopamine D2 receptors in the evening or at night, or at about bedtime, wherein the antipsychotic agent is Compound 1, or a pharmaceutically acceptable salt thereof, and wherein the method minimizes adverse events associated with antipsychotic agents with affinity to dopamine D2 receptors.

In some embodiments, provided is a method of treating a neurological or psychiatric disease or disorder in a patient without subjecting the patient to a clinically significant risk of adverse events, the method comprising administering to the patient a therapeutically effective amount of Compound 1, or a pharmaceutically acceptable salt thereof, in the evening or at night, or at about bedtime, wherein the risk of adverse events are associated with antipsychotic agents with affinity to dopamine D2 receptors. In some embodiments, the disease or disorder is schizophrenia.

In some embodiments, provided is a method of administering an antipsychotic agent to a patient in need thereof without causing a clinically significant risk of adverse events, comprising administering to the patient a therapeutically effective amount of Compound 1, or a pharmaceutically acceptable salt thereof, in the evening or at night, or at about bedtime, wherein the patient does not experience a clinically significant adverse event.

In some embodiments, provided is a method of treating a patient having a neurological or psychiatric disease or disorder without causing a clinically significant risk of adverse events, comprising administering to the patient a therapeutically effective amount of Compound 1, or a pharmaceutically acceptable salt thereof, in the evening or at night, or at about bedtime. In some embodiments, the patient has schizophrenia.

In some embodiments, adverse events refers to one or more of the following: cardiovascular adverse events (e.g., atrial tachycardia, bradycardia, cardiovascular insufficiency, palpitations, postural tachycardia syndrome, increased blood pressure, hypertension, hypotension, hot flush, QT prolongation, orthostatic hypotension, or orthostatic tachycardia), extrapyramidal adverse events (e.g., akathisia, restlessness, joint stiffness, musculoskeletal stiffness, nuchal rigidity, postural tremor, or tremor), hyperprolactinemia, insomnia, anxiety, headaches, schizophrenia, somnolence, agitation, nausea, diarrhea, and dyspepsia.

In some embodiments, the method is efficacious for the treatment of the neurological or psychiatric disease or disorder in the patient. In some examples, the method results in improvement in one or more of Positive and Negative Symptom Scale (PANSS) total score, PANSS subscores (negative, positive, general psychopathology), Clinical Global Impressions-Severity (CGI-S) score, Brief Negative Symptom Scale (BNSS) total score, and Montgomery-Asberg Depression Rating Scale (MADRS) total score.

In some embodiments, provided is a method of treating a neurological or psychiatric disease or disorder in a patient, comprising administering to the patient a therapeutically effective amount of an antipsychotic agent with no direct affinity to dopamine D2 receptors, in the evening or at night, or at about bedtime, wherein the method is substantially devoid of adverse events in the patient, wherein the adverse events are associated with antipsychotic agents with affinity to dopamine D2.

In some embodiments, Compound 1, or a pharmaceutically acceptable salt thereof is Compound 1 hydrochloride of crystalline Form A.

BRIEF DESCRIPTION OF THE DRAWINGS

FIG. 18A, FIG. 18B, FIG. 18C, FIG. 18D show the change from open-label baseline at week 26 in lipids: FIG. 18A total cholesterol (overall), FIG. 18B triglycerides (overall), FIG. 18C HDL (overall), and FIG. 18D LDL (overall).

FIG. 19A glucose (overall), and FIG. 19B HbA1c.

FIG. 21 is the XRPD measured in transmission mode and FIG. 22 in reflection mode.

DETAILED DESCRIPTION

Figure 1:
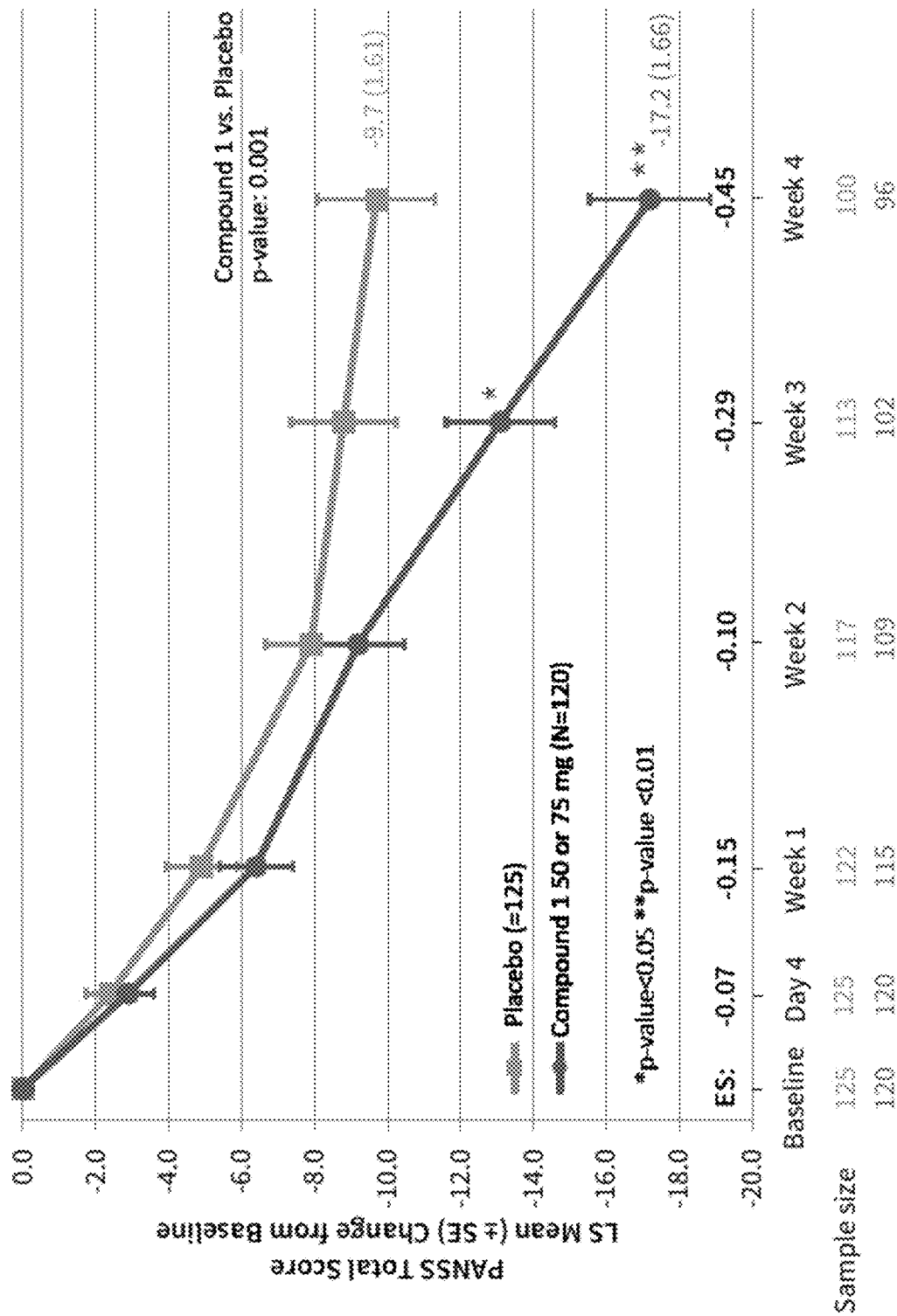
FIG. 1 shows the MMRM analysis of change from baseline in PANSS total score for the study of Example 1.1.

All published documents cited herein are hereby incorporated herein by reference in their entirety.

Unless defined otherwise, all technical and scientific terms used herein have the same meaning as commonly understood by one of ordinary skill in the art to which this disclosure belongs. Accordingly, the following terms are intended to have the following meanings:

As used herein, the singular forms "a", "an" and "the" are intended to include the plural forms as well, unless the context clearly indicates otherwise.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

As used herein, the terms "treatment," "treat," and "treating" refer to reversing, alleviating, delaying the onset of, or inhibiting the progress of a disease or disorder, or one or more symptoms thereof, including but not limited to therapeutic benefit. In some embodiments, treatment is administered after one or more symptoms have developed, for example, acute exacerbation of symptoms. In some embodiments, treatment may be administered in the absence of symptoms. For example, treatment may be administered to a subject prior to the onset of symptoms (e.g., in light of a history of symptoms and/or in light of genetic or other susceptibility factors). Treatment may also be continued after symptoms have resolved, for example to prevent or delay their recurrence.

Therapeutic benefit includes eradication and/or amelioration of the underlying disorder being treated; it also includes the eradication and/or amelioration of one or more of the symptoms associated with the underlying disorder such that an improvement is observed in the subject, notwithstanding that the subject may still be afflicted with the underlying disorder. In some embodiments, "treatment" or "treating" includes one or more of the following: (a) inhibiting the disorder (for example, decreasing one or more symptoms resulting from the disorder, and/or diminishing the extent of the disorder); (b) slowing or arresting the development of one or more symptoms associated with the disorder (for example, stabilizing the disorder and/or delaying the worsening or progression of the disorder); and/or (c) relieving the disorder (for example, causing the regression of clinical symptoms, ameliorating the disorder, delaying the progression of the disorder, and/or increasing quality of life.)

As used herein, "administering" or "administration" of Compound 1, or a pharmaceutically acceptable salt thereof, encompasses the delivery to a subject of Compound 1, or a pharmaceutically acceptable salt thereof, or a prodrug or other pharmaceutically acceptable derivative thereof, using any suitable formulation or route of administration, e.g., as described herein.

As used herein, the term "therapeutically effective amount" or "effective amount" refers to an amount that is effective to elicit the desired biological or medical response, including the amount of a compound that, when administered to a subject for treating a disorder, is sufficient to effect such treatment of the disorder. The effective amount will vary depending on the disorder, and its severity, and the age, weight, etc. of the subject to be treated. The effective amount may be in one or more doses (for example, a single dose or multiple doses may be required to achieve the desired treatment endpoint). An effective amount may be considered to be given in an effective amount if, in conjunction with one or more other agents, a desirable or beneficial result may be or is achieved. Suitable doses of any co-administered compounds may optionally be lowered due to the combined action, additive or synergistic, of the compound.

As used herein, "delaying" development of a disorder mean to defer, hinder, slow, stabilize, and/or postpone development of the disorder. Delay can be of varying lengths of time, depending on the history of the disease and/or the individual being treated.

As used herein, "prevention" or "preventing" refers to a regimen that protects against the onset of the disorder such that the clinical symptoms of the disorder do not develop. Accordingly, "prevention" relates to administration of a therapy to a subject before signs of the diseases are detectable in the subject (for example, administration of a therapy in the absence of a detectable syndrome of the disorder). The subject may be an individual at risk of developing the disorder.

As used herein, an "at risk" individual is an individual who is at risk of developing a disorder to be treated. This may be shown, for example, by one or more risk factors, which are measurable parameters that correlate with development of a disorder and are known in the art.

As used herein, "subject" or "patient" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. As used herein, "subject" and "patient" are interchangeable.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of Compound 1 include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates.

As used herein, the term "pharmaceutically acceptable excipient" includes, without limitation, any binder, filler, adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, anti-caking agent, flavor, desiccants, plasticizers, disintegrants, lubricant, polymer matrix system, polymer coating system and polishing agents, which has been approved by the United States Food and Drug Administration as being acceptable for use in humans or domestic animals.

As used herein, a "clinically significant" risk of an adverse event refers to a risk that is greater than placebo by a statistically significant margin. When the risk of adverse events or a particular adverse event is less than, the same as, or about the same as placebo, the risk is not clinically significant.

As used herein, a "clinically meaningful" risk of an adverse event refers to a risk that is less than, but not necessarily by a statistically significant margin, the risk of the same adverse event in an antipsychotic agent with affinity to dopamine D2 receptors. When the risk of adverse events or a particular adverse event is less than an antipsychotic agent with affinity to dopamine D2 receptors, the risk is not clinically meaningful. In some embodiments, the risk of a clinically meaningful adverse event can be determined by one having ordinary skill in the art of treating and/or prescribing an antipsychotic agent to a patient in need. In some embodiments, the risk of a clinically meaningful adverse event can be determined comparative calculations across a patient population.

As used herein a method that is "substantially devoid" of adverse events refers to a method with an incidence of adverse events that is less than, the same as, or about the same as placebo.

As used herein "minimizing" adverse events refers to a statistically significant reduction in the incidence of adverse events in a patient population compared to the paradigmatic incidence of adverse events in a patient population treated with antipsychotic agents that have affinity to the D2 dopamine receptor. Such antipsychotic agents (e.g., as defined herein) that have affinity to the D2 dopamine receptor would have therapeutic affinity to the D2 dopamine receptor, such that one of skill in the art could propose direct targeting of the D2 dopamine receptor as a primary (either alone or in combination with another receptor) mechanism of action. The corresponding risk of adverse events in a single patient is reduced accordingly. In some embodiments, the incidence of an adverse event refers to the frequency or percentage of a specific adverse event over a patient population. In some embodiments, the incidence of an adverse event refers to the total number of adverse events experienced by an individual subject.

As used herein, "antipsychotic agents" are a class of medication specifically used to treat, prevent, or manage psychosis, for example in schizophrenia or bipolar disorder, and more broadly for treatment of various neurological and psychiatric disorders. First generation antipsychotic agents are known as "typical antipsychotics," which include chlorpromazine, chlorprothixene, levomepromazine, mesoridazine, periciazine, promazine, thioridazine, loxapine, molindone, perphenazine, thiothixene, droperidol, flupentixol, fluphenazine, haloperidol, pimozide, prochlorperazine, thioproperazine, trifluoperazine and zuclopenthixol. Second generation antipsychotic agents are known as "atypical antipsychotics," which include aripiprazole, asenapine maleate, clozapine, iloperidone, lurasidone, olanzapine, olanzapine/fluoxetine, paliperidone, quetiapine, risperidone, and ziprasidone. Both typical and atypical antipsychotics target and have affinity to D2 dopamine receptors.

"Adverse events" are any untoward medical occurrence associated with the use of a drug in humans, whether or not considered drug related. "Adverse events," as used herein, include events associated with antipsychotic agents with affinity to dopamine D2 receptors. In some embodiments, adverse events are drug seeking behavior. In some embodiments, the drug seek behavior are abuse, misuse, addiction, physical dependence, and/or tolerance. In some embodiments, adverse events are abuse, misuse, addiction, physical dependence, and/or tolerance. In some embodiments, administration of Compound 1, or a pharmaceutically acceptable salt thereof, does not clinically significantly increase a patient's tendency for drug seeking behavior. In some embodiments, administration of Compound 1, or a pharmaceutically acceptable salt thereof, does not clinically significantly increase a patient's tendency for abuse, misuse, addiction, physical dependence, or tolerance. In some embodiments, administration of Compound 1, or a pharmaceutically acceptable salt thereof, does not clinically significantly increase a patient's tendency for abuse, misuse, addiction, or physical dependence. In some embodiments, Compound 1, or a pharmaceutically acceptable salt thereof, is not a controlled substance. As used herein, the term "abuse" means the intentional, non-therapeutic use of a drug, even once, for its desirable psychological or physiological effects. As used herein, the term "misuse" means the intentional use, for therapeutic purposes, of a drug by an individual in a way other than prescribed by a health care provider or for whom it was not prescribed. As used herein, the term "addiction" means a cluster of behavioral, cognitive, and physiological phenomena that may include a strong desire to take the drug, difficulties in controlling drug use (e.g., continuing drug use despite harmful consequences, giving a higher priority to drug use than other activities and obligations), and possible tolerance or physical dependence. Physical dependence is not synonymous with addiction; a patient may be physically dependent on a drug without having an addiction to the drug. Similarly, abuse is not synonymous with addiction. Tolerance, physical dependence, and withdrawal are all expected biological phenomena that are the consequences of chronic treatment with certain drugs. These phenomena by themselves do not indicate a state of addiction. As used herein, the term "physical dependence" means a state that develops as a result of physiological adaptation in response to repeated drug use, manifested by withdrawal signs and symptoms after abrupt discontinuation or a significant dose reduction of a drug. As used herein, the term "tolerance" means a physiological state characterized by a reduced response to a drug after repeated administration (e.g., a higher dose of a drug is required to produce the same effect that was once obtained at a lower dose). As used herein, the term "controlled substance" means a drug or other substance, or immediate precursor, included in schedule I, II, III, IV, or V of 21 USC §§ 811-814, which is incorporated by reference herein.

"Adverse events associated with antipsychotic agents with affinity to dopamine D2 receptors" are understood by a person of ordinary skill in the art as adverse events that are paradigmatic of D2 antipsychotic therapy. In some embodiments, the adverse events associated with antipsychotic agents with affinity to dopamine D2 receptors is any one or more of class effects of antipsychotics agents. In some embodiments, the adverse events associated with antipsychotic agents with affinity to dopamine D2 receptors is any one or more of class effects of typical antipsychotics. In some embodiments, the adverse events associated with antipsychotic agents with affinity to dopamine D2 receptors is any one or more of class effects of atypical antipsychotics. In some embodiments, the adverse events associated with antipsychotic agents with affinity to dopamine D2 receptors are cardiovascular adverse events or extrapyramidal adverse events. In some embodiments, the adverse events associated with antipsychotic agents with affinity to dopamine D2 receptors include cardiovascular adverse events (e.g., atrial tachycardia, bradycardia, cardiovascular insufficiency, palpitations, postural tachycardia syndrome, increased blood pressure, hypertension, hypotension, hot flush, QT prolongation, orthostatic hypotension, or orthostatic tachycardia), extrapyramidal adverse events (e.g., akathisia, restlessness, joint stiffness, musculoskeletal stiffness, nuchal rigidity, postural tremor, or tremor), hyperprolactinemia, insomnia, anxiety, headaches, schizophrenia, somnolence, agitation, nausea, diarrhea, and dyspepsia.

"About," used herein with respect to time (e.g., bedtime), refers to an indicated time±no more than three hours, e.g., the indicated time±3 hours, the indicated time±2 hours, the indicated time±1 hour, the indicated time±30 minutes or the indicated time±15 minutes.

"Bedtime," as used herein, refers to the time at which a subject typically goes to bed in order to sleep.

The present disclosure describes various embodiments. A person of ordinary skill in the art reviewing the disclosure will readily recognize that various embodiments can be combined in any variation. For example, embodiments of the disclosure include treatment of various disorders, patient populations, administrations of dosage forms, at various dosages, minimization of various adverse events, and improvements in various efficacy measures, etc. Any combinations of various embodiments are within the scope of the disclosure.

Compound 1, as referred to herein for use in the methods of the present disclosure, has the following structure:

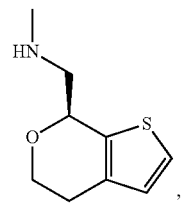

or a pharmaceutically acceptable salt thereof. Unless stated otherwise, or unless context requires otherwise, for purposes of this disclosure, the term "Compound 1" also includes pharmaceutically acceptable salts of:

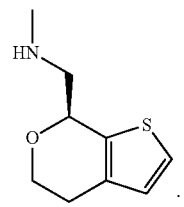

The chemical name for Compound 1 is (S)-(4,5-dihydro-7H-thieno[2,3-c]pyran-7-yl)-N-methylmethanamine (which may be abbreviated as "(S)-TPMA"), or a pharmaceutically acceptable salt thereof. One having ordinary skill in the art would appreciate the variety of nomenclature for compounds. Accordingly, Compound 1 may also be identified as (S)-1-(4,7-dihydro-5H-thieno[2,3-c]pyran-7-yl)-N-methylmethanamine, (S)-1-(5,7-dihydro-4H-thieno[2,3-c]pyran-7-yl)-N-methylmethanamine, or others, or a pharmaceutically acceptable salt thereof. For example, Compound 1, or a pharmaceutically acceptable salt thereof, has been identified as SEP-0363856 or SEP-856, and has received a Breakthrough Therapy Designation from the United States Food and Drug Administration (FDA) as a novel agent for the treatment of people with schizophrenia. Breakthrough Therapy Designation is intended to expedite the development and review of drugs for serious or life-threatening conditions when preliminary clinical evidence indicates that the drug may demonstrate substantial improvement over available therapy on one or more clinically significant endpoints. The FDA granted Breakthrough Therapy Designation for Compound 1, or a pharmaceutically acceptable salt thereof, based on pivotal, Phase 2 data from clinical trials disclosed herein. Compound 1, or a pharmaceutically acceptable salt thereof, is an antipsychotic agent with a non-direct-D2 mechanism of action, which shows broad efficacy in animal models of psychosis and depression. The molecular targets responsible for the antipsychotic and antidepressant efficacy of Compound 1, or a pharmaceutically acceptable salt thereof, are understood to be agonist activity at both trace amine associated receptor-1 (TAAR1) and $5HT_{1A}$ receptors. For example, as disclosed in Dedic et al. THE JOURNAL OF PHARMACOLOGY AND EXPERIMENTAL THERAPEUTICS 371, 1-14 (2019), Compound 1 was tested against several panels of known molecular targets (ion channels, G protein-coupled receptors (GPCRs), and enzymes, and, at 10 µM, Compound 1 showed >50% inhibition of specific binding at $\alpha_{2A}$, $\alpha_{2B}$, $D_2$, $5\text{-HT}_{1A}$, $5\text{-HT}_{1B}$, $5\text{-HT}_{1D}$, $5\text{-HT}_{2A}$, $5\text{-HT}_{2B}$, $5\text{-HT}_{2C}$, and $5\text{-HT}_7$ receptors. Further receptor panel screening and follow-up functional testing showed that Compound 1 exhibited a range of activities at several receptors. Agonism at the human TAAR1 receptor ($EC_{50}$ of 0.14±0.062

μM, maximum efficacy ($E_{max}$)=101.3%±1.3%) and the 5-HT$_{1A}$ receptor (EC$_{50}$=2.3 μM with values ranging from 0.1 to 3 μM, $E_{max}$=74.7%±19.6%). In D$_2$ receptor functional assays, Compound 1 exhibited weak partial agonism with EC$_{50}$ values of 10.44±4 μM (cAMP, $E_{max}$=23.9%±7.6%) and 8 μM (β-arrestin recruitment, $E_{max}$=27.1%). Without being bound to a particular mechanism of action, Compound 1 is theorized also to act as a pre-synaptic dopamine modulator.

Compound 1 can be used in the methods described herein as the free base or in the form of a pharmaceutically acceptable salt. In some embodiments, a hydrochloric acid (HCl) salt of Compound 1 is used in the methods described herein.

Compound 1, or a pharmaceutically acceptable salt thereof, can be obtained according to the production methods described in PCT Patent Publication No. WO2011/069063 (U.S. Pat. No. 8,710,245, issued Apr. 29, 2014) or PCT Patent Publication No. WO2019/161238, which are incorporated herein by reference in entirety and for all purposes, or a method analogous thereto.

Compound 1, or a pharmaceutically acceptable salt thereof, may be in amorphous or crystalline form. In some embodiments, a crystalline form of Compound 1, or a pharmaceutically acceptable salt thereof, is used in the methods described herein. In some embodiments, crystalline Form A of the HCl salt of Compound 1 is used in the methods described herein.

In some embodiments, crystalline Form A of the HCl salt of Compound 1 is characterized by a powder x-ray diffraction pattern comprising peaks, in terms of 2-theta, at 9.6±0.2°, 14.9±0.2°, 20.5±0.2°, and 25.1±0.2°, in some embodiments further comprising peaks at 20.2±0.2° and 20.8±0.2°, and in some embodiments further comprising peaks at 20.2±0.2° and 20.8±0.2° and a prominent peak at two or more of 17.9±0.2°, 24.8±0.2° and 27.1±0.2°. An example method of preparing crystalline Form A of the HCl salt of Compound 1 is provided in Example 4.

In some embodiments, Compound 1, or a pharmaceutically acceptable salt thereof, is substantially enantiomerically pure. In some examples, a composition comprising Compound 1, or a pharmaceutically acceptable salt thereof, comprises greater than or equal to about 90%, 95%, 97%, 99%, 99.5%, 99.7% or 99.9% of Compound 1, relative to the total amount of Compound 1 and its (R)-enantiomer in the composition. In some embodiments, a substantially enantiomerically pure crystalline Form A of the HCl salt of Compound 1 is used in the methods described herein.

Also provided herein are pharmaceutical compositions and dosage forms, comprising Compound 1, or a pharmaceutically acceptable salt thereof, and one or more pharmaceutically acceptable excipients. Compositions and dosage forms provided herein may further comprise one or more additional active ingredients. Compound 1, or a pharmaceutically acceptable salt thereof, may be administered as part of a pharmaceutical composition as described herein.

Selecting an appropriate pharmaceutical drug to treat a neurological or psychiatric disease or disorder involves finding a pharmaceutical drug which causes few or no adverse events in the patient. As disclosed herein, doctors wishing to avoid the trial and error approach to treating a neurological or psychiatric disease or disorder can select, from available antipsychotic agents, Compound 1 to treat the patient without a clinically significant risk of an adverse event. For example, for patients at risk for QT prolongation this can be important since QT prolongation is a serious adverse event which can lead to death. As disclosed herein, Compound 1, unlike some antipsychotics agents with affinity to dopamine D2 receptors, does not cause a clinically significant risk of QT prolongation, and may allow for safer dosing in patients who are at an elevated risk of QT prolongation. The risk of QT prolongation in patients who have not been previously treated with a neurological or psychiatric drug may be unknown. However, in some embodiments provided herein, Compound 1 can be administered without a clinically significant risk of QT prolongation. Other adverse events such as other cardiovascular events may take some time to manifest themselves, such as weight gain, a modification of the blood lipids or blood glucose levels. Over time, such events can cause cardiovascular issues in the patient. With the administration of Compound 1, the adverse events can be avoided or greatly reduced.

The present disclosure relates to methods of treating neurological and psychiatric diseases and disorders, such as schizophrenia.

In some embodiments, provided is a method of treating a patient having a neurological or psychiatric disease or disorder, comprising orally administering to the patient Compound 1

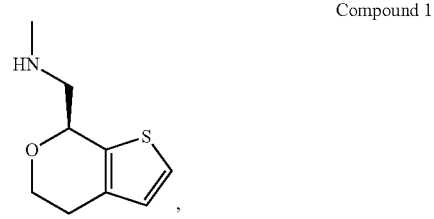

or a pharmaceutically acceptable salt thereof.

In some embodiments, provided is a method of treating a neurological or psychiatric disease or disorder in a patient, comprising administering to the patient a therapeutically effective amount of Compound 1, or a pharmaceutically acceptable salt thereof,

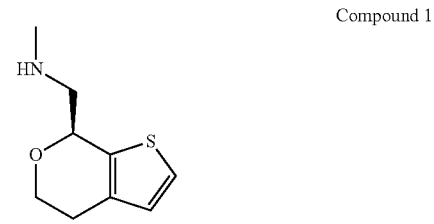

wherein the method minimizes adverse events in the patient. In some embodiments, the method minimizes adverse events associated with antipsychotic agents with affinity to dopamine D2 receptors.

In some embodiments, provided is a method of treating a neurological or psychiatric disease or disorder in a patient, comprising administering to the patient a therapeutically effective amount of Compound 1, or a pharmaceutically acceptable salt thereof, wherein the method is substantially devoid of adverse events. In some embodiments, the method produces a risk of adverse events in the patient that is about the same as or similar to placebo.

In some embodiments, provided is a method of treating a neurological or psychiatric disease or disorder in a patient, wherein the method is substantially devoid of adverse events of an antipsychotic agent having affinity to dopamine D2 receptors, comprising administering to the patient a therapeutically effective amount of an antipsychotic agent with no direct affinity to dopamine D2 receptors selected from Compound 1, or a pharmaceutically acceptable salt thereof.

In some embodiments, provided is a method of minimizing adverse events in a patient in need of treatment for a neurological or psychiatric disease or disorder, the method comprising administering to the patient a therapeutically effective amount of an antipsychotic agent with no direct affinity to dopamine D2 receptors, wherein the antipsychotic agent is Compound 1, or a pharmaceutically acceptable salt thereof, and wherein the method minimizes adverse events associated with antipsychotic agents with affinity to dopamine D2 receptors. In some embodiments, the method has reduced incidence of such adverse events compared to treatment with antipsychotic agents with affinity to dopamine D2 receptors.

In some embodiments, provided is a method of treating a neurological or psychiatric disease or disorder in a patient without subjecting the patient to a clinically significant risk of adverse events, the method comprising administering to the patient a therapeutically effective amount of Compound 1, or a pharmaceutically acceptable salt thereof, wherein the risk of adverse events are associated with antipsychotic agents with affinity to dopamine D2 receptors.

In some embodiments, provided is a method of administering an antipsychotic agent to a patient in need thereof without causing a clinically significant risk of adverse events, comprising administering to the patient a therapeutically effective amount of Compound 1, or a pharmaceutically acceptable salt thereof, wherein the patient does not experience a clinically significant adverse event. In some embodiments, the method treats a neurological or psychiatric disease or disorder (e.g., schizophrenia) in the patient.

In some embodiments, provided is a method of treating a neurological or psychiatric disease or disorder in a patient, comprising administering to the patient a therapeutically effective amount of an antipsychotic agent with no direct affinity to dopamine D2 receptors, wherein the method is substantially devoid of adverse events in the patient, wherein the adverse events are associated with antipsychotic agents with affinity to dopamine D2.

In some embodiments, provided is the use of Compound 1, or a pharmaceutically acceptable salt thereof, in the treatment of a neurological or psychiatric disease or disorder as generally described herein, e.g., with minimized adverse events. Also provided is Compound 1, or a pharmaceutically acceptable salt thereof, for use in the treatment of a neurological or psychiatric disease or disorder as generally described herein, e.g., with minimized adverse events. Also provided is use of Compound 1, or a pharmaceutically acceptable salt thereof, in the manufacture of a medicament for the treatment of a neurological or psychiatric disease or disorder as generally described herein, e.g., with minimized adverse events.

In some embodiments, Compound 1, or a pharmaceutically acceptable salt thereof, is administered daily for a 29-day treatment period. In some embodiments, Compound 1, or a pharmaceutically acceptable salt thereof, is administered daily for a 26-week or 30-week treatment period.

In some embodiments, adverse events refers to any one or more of the following: cardiovascular adverse events (atrial tachycardia, bradycardia, cardiovascular insufficiency, palpitations, postural tachycardia syndrome, increased blood pressure, hypertension, hypotension, hot flush, QT prolongation, orthostatic hypotension, orthostatic tachycardia), extrapyramidal adverse events (akathisia, restlessness, joint stiffness, musculoskeletal stiffness, nuchal rigidity, postural tremor, tremor), hyperprolactinemia, insomnia, anxiety, headaches, schizophrenia, somnolence, agitation, nausea, diarrhea, and dyspepsia.

In some embodiments, the methods of the present disclosure are efficacious for the treatment of the neurological or psychiatric disease or disorder in the patient. In some examples, the method results in improvement in one or more of Positive and Negative Symptom Scale (PANSS) total score, PANSS subscores (negative, positive, general psychopathology), Clinical Global Impressions-Severity (CGI-S) score, Brief Negative Symptom Scale (BNSS) total score, and Montgomery-Asberg Depression Rating Scale (MADRS) total score.

In some embodiments, the method results in one or more of:

a reduction from baseline in PANSS total score, e.g., a reduction from baseline in PANSS total score of at least 1, 2, 3, 4, 5, 7, 10, 15, or 17 (e.g., at least 17.2) or a reduction from baseline in PANSS total score of at least 1%, 2%, 3%, 4%, 5%, 7%, 10%, 15%, or 20% or a PANSS total score effect size of at least 0.1, 0.2, 0.3, or 0.4 (e.g., at least 0.45) or a PANSS responder rate with statistically significant improvement over placebo (e.g., at least 1%, 2%, 3%, 4%, 5%, 7%, 10%, 15% or 20% better responder rate than placebo);

a reduction from baseline in PANSS negative subscale score, e.g., a reduction from baseline in PANSS negative subscale score of at least 0.25. 0.5, 0.75, 1, 1.5, 2, 2.5 or 3 (e.g., at least 3.1) or a reduction from baseline in PANSS negative subscale score of at least 1%, 2%, 3%, 4%, 5%, 7%, 10%, 15%, or 20% or a PANSS negative subscale score effect size of at least 0.1, 0.2, 0.3 or 0.35 (e.g., at least 0.37);

a reduction from baseline in PANSS positive subscale score, e.g., a reduction from baseline in PANSS positive subscale score of at least 1, 2, 3, 4, or 5 (e.g., at least 5.5) or a reduction from baseline in PANSS positive subscale score of at least 1%, 2%, 3%, 4%, 5%, 7%, 10%, 15%, or 20% or a PANSS positive subscale score effect size of at least 0.1, 0.2 or 0.3 (e.g., at least 0.32);

a reduction from baseline in PANSS general psychopathology subscale score, e.g., a reduction from baseline in PANSS general psychopathology subscale score of at least 1, 2, 3, 4, 5, 7 or 9 (e.g., at least 9) or a reduction from baseline in PANSS general psychopathology subscale score of at least 1%, 2%, 3%, 4%, 5%, 7%, 10%, 15%, or 20% or a PANSS general psychopathology subscale score effect size of at least 0.1, 0.2, 0.3, 0.4 or 0.5 (e.g., at least 0.51);

a reduction from baseline in CGI-S score, e.g., a reduction from baseline in CGI-S score of at least 0.2, 0.4, 0.6, 0.8 or 1 (e.g., at least 1) or a reduction from baseline in CGI-S score of at least 1%, 2%, 3%, 4%, 5%, 7%, 10%, 15%, or 20% or a CGI-S score effect size of at least 0.1, 0.2, 0.3, 0.4 or 0.5 (e.g., at least 0.52);

a reduction from baseline in BNSS total score, e.g., a reduction from baseline in BNSS total score of at least 1, 2, 3, 4, 5, 6 or 7 (e.g., at least 7.1) or a reduction from baseline in BNSS total score of at least 1%, 2%, 3%, 4%, 5%, 7%, 10%, 15%, or 20% or a BNSS total score effect size of at least 0.1, 0.2, 0.3, 0.4, or 0.45 (e.g., at least 0.48); and a reduction from baseline in MADRS total score, e.g., a reduction from baseline in MADRS total score of at least 0.5, 1, 1.5, 2, 2.5 or 3 (e.g., at least 3.3) or a reduction from baseline in MADRS total score of at least 1%, 2%, 3%, 4%, 5%, 7%, 10%, 15%, or 20% or a MADRS total score effect size of at least 0.1, 0.2, or 0.3 (e.g., at least 0.32).

In some embodiments, the reduction in PANSS (total or subscore), CGI-S, BNSS, or MADRS score is measured after a 29-day treatment period.

In some embodiments, the reduction in score is measured after a 30-week treatment period. In some embodiments, the methods of the present disclosure result in (i) a reduction from baseline in PANSS total score of at least about 30 after 30 weeks of treatment; (ii) a reduction from baseline in PANSS positive subscale score of at least about 10 after 30 weeks of treatment; (iii) a reduction from baseline in PANSS negative subscale score of at least about 5 after 30 weeks of treatment; (iv) a reduction from baseline in PANSS general psychopathology subscale score of at least about 15 after 30 weeks of treatment; (v) a reduction from baseline in CGI-S score of at least about 1.5 after 30 weeks of treatment; (vi) a reduction from baseline in BNSS total score of at least about 10 after 30 weeks of treatment; and/or (vii) a reduction from baseline in MADRS total score of at least about 5 after 30 weeks of treatment.

In some embodiments, the methods of the present disclosure result in a reduced number of adverse events leading to discontinuation during a treatment period, e.g., 29 days, 26 weeks, or 30 weeks. For example, in some embodiments, the method results in less than 50%, less than 40% or less than 35% of patients discontinuing treatment due to adverse events over a 26-week or 30-week treatment period.

In some embodiments, the neurological or psychiatric disease or disorder is schizophrenia. In some embodiments, the patient has acute exacerbation of schizophrenia. In some embodiments, treating schizophrenia comprises ameliorating a symptom of schizophrenia. In some embodiments, treating schizophrenia comprises treating negative symptoms of schizophrenia.

In some embodiments, the neurological or psychiatric disease or disorder is Parkinson's disease psychosis.

In some embodiments, the neurological or psychiatric disease or disorder is schizophrenia spectrum disorder, schizophrenia negative symptoms, attenuated psychosis syndrome, prodromal schizophrenia, delusional disorder, psychosis, psychotic disorder, delirium, Tourette's syndrome, post-traumatic stress disorder, behavior disorder, affective disorder, depression, bipolar disorder, major depressive disorder, dysthymia, manic disorder, seasonal affective disorder, obsessive-compulsive disorder, narcolepsy, REM behavior disorder, substance abuse or dependency, Lesch-Nyhan disease, Wilson's disease, autism, Alzheimer's disease agitation and psychosis, or Huntington's chorea.

In some embodiments, the neurological or psychiatric disease or disorder is selected from schizophrenia, attenuated psychosis syndrome, prodromal schizophrenia, schizoid personality disorder, and schizotypal personality disorder.

In some embodiments, the neurological or psychiatric disease or disorder is Alzheimer's disease agitation and psychosis. In some embodiments, the patient has dementia. In some embodiments, the neurological or psychiatric disease or disorder is dementia-related psychosis.

In some embodiments, the psychosis is selected from organic psychosis, drug-induced psychosis, Parkinson's disease psychosis, and excitative psychosis.

In some embodiments, the neurological or psychiatric disease or disorder is a bipolar disorder selected from bipolar disorder and bipolar depression.

In some embodiments, the patient fails to respond adequately to antipsychotic agents which are at least one typical antipsychotic agent or at least one atypical antipsychotic agent. In some embodiments, the patient fails to respond adequately to antipsychotic agents wherein the antipsychotic agents are typical antipsychotics or atypical antipsychotics. In some embodiments, the patient fails to respond adequately to antipsychotic agents wherein the antipsychotic agents are typical antipsychotics (e.g., chlorpromazine, chlorprothixene, levomepromazine, mesoridazine, periciazine, promazine, thioridazine, loxapine, molindone, perphenazine, thiothixene, droperidol, flupentixol, fluphenazine, haloperidol, pimozide, prochlorperazine, thioproperazine, trifluoperazine, zuclopenthixol) or atypical antipsychotics (e.g., aripiprazole, asenapine maleate, clozapine, iloperidone, lurasidone, olanzapine, olanzapine/fluoxetine, paliperidone, quetiapine, risperidone, ziprasidone)

In some embodiments, the patient is geriatric.

In some embodiments, treating a neurological or psychiatric disease or disorder comprises ameliorating a symptom of the neurological or psychiatric disease or disorder.

In some embodiments, the patient is characterized by one or more of:
  the patient is an adult;
  the patient has been diagnosed with schizophrenia for at least 6 months;
  the patient has been experiencing acute exacerbation of psychotic symptoms for at least 2 months;
  the patient has had no more than 2 prior hospitalizations for treatment of acute exacerbation of schizophrenia;
  the patient has a baseline PANSS total score of at least 80;
  the patient has a baseline PANSS score of at least 4 on two or more of: delusions, conceptual disorganization, hallucinatory behavior, and unusual thought content; and
  the patient has a baseline CGI-S score of at least 4.

In some embodiments, adverse events refers to one or more of the following: cardiovascular adverse events (e.g., atrial tachycardia, bradycardia, cardiovascular insufficiency, palpitations, postural tachycardia syndrome, increased blood pressure, hypertension, hypotension, hot flush, QT prolongation, orthostatic hypotension, or orthostatic tachycardia), extrapyramidal adverse events (e.g., akathisia, restlessness, joint stiffness, musculoskeletal stiffness, nuchal rigidity, postural tremor, or tremor), hyperprolactinemia, insomnia, anxiety, headaches, schizophrenia, somnolence, agitation, nausea, diarrhea, and dyspepsia.

The D2 dopamine receptor is the primary target for both typical and atypical antipsychotic agents. Wang et al. NATURE 555, 269-273 (2018). Unfortunately, many drugs that target the D2 dopamine receptor cause serious and potentially life-threatening side effects due to promiscuous activities against related receptors. Wang et al. NATURE 555, 269-273 (2018). Currently available antipsychotic agents that have affinity to the D2 dopamine receptor include typical antipsychotics, such as chlorpromazine, chlorprothixene, levomepromazine, mesoridazine, periciazine, promazine, thioridazine, loxapine, molindone, perphenazine, thiothixene, droperidol, flupentixol, fluphenazine, haloperidol, pimozide, prochlorperazine, thioproperazine, trifluoperazine and zuclopenthixol and atypical antipsychotics, such as aripiprazole, asenapine maleate, clozapine, iloperidone, lurasidone, olanzapine, olanzapine/fluoxetine, paliperidone, quetiapine, risperidone, and ziprasidone. Adverse events associated with typical and atypical antipsychotics include cardiovascular adverse events (e.g., atrial tachycardia, bradycardia, cardiovascular insufficiency, palpitations, postural tachycardia syndrome, increased blood pressure, hypertension, hypotension, hot flush, QT prolongation, orthostatic hypotension, or orthostatic tachycardia), extrapyramidal adverse events (e.g., akathisia, restlessness, joint stiffness, musculoskeletal stiffness, nuchal rigidity, postural tremor, or tremor), and hyperprolactinemia, insomnia, anxiety, headaches, schizophrenia, somnolence, agitation, nausea, diarrhea, and dyspepsia.

In some embodiments, the adverse events associated with antipsychotics are any one or more of class-effect adverse events as defined by EBGM rankings using FAERS. In some embodiments, the adverse events associated with antipsychotics are any one or more of: Hyperprolactinaemia, Blood prolactin abnormal, Blood prolactin increased, Galactorrhoea, Cogwheel rigidity, Obesity, Metabolic syndrome, Akathisia, Oromandibular dystonia, Parkinsonism, Drooling, Oculogyric crisis, Obsessive-compulsive disorder, Muscle rigidity, Type 2 diabetes mellitus, Diabetes mellitus, Overweight, Parkinsonian gait, Tongue spasm, Tardive dyskinesia, Bradykinesia, Tic, Psychomotor retardation, Extrapyramidal disorder, Enuresis, Glucose tolerance impaired, Salivary hypersecretion, Dystonia, Glycosuria, Restlessness, Torticollis, Impaired fasting glucose, Dermatillomania, Body mass index increased, Hyperkinesia, Hepatitis viral, Dyskinesia, Blood triglycerides increased, Electrocardiogram QT prolonged, Dyssomnia, Orthostatic hypertension, Bruxism, Increased appetite, Excessive eye blinking, Pancreatitis chronic, Weight increased, Dyslipidaemia, Restless legs syndrome, Tongue biting, or Nuchal rigidity.

In some embodiments, Compound 1 does not cause a clinically significant increase in the risk of an adverse event of any one or more of Hyperprolactinaemia, Blood prolactin abnormal, Blood prolactin increased, Galactorrhoea, Cogwheel rigidity, Obesity, Metabolic syndrome, Akathisia, Oromandibular dystonia, Parkinsonism, Drooling, Oculogyric crisis, Obsessive-compulsive disorder, Muscle rigidity, Type 2 diabetes mellitus, Diabetes mellitus, Overweight, Parkinsonian gait, Tongue spasm, Tardive dyskinesia, Bradykinesia, Tic, Psychomotor retardation, Extrapyramidal disorder, Enuresis, Glucose tolerance impaired, Salivary hypersecretion, Dystonia, Glycosuria, Restlessness, Torticollis, Impaired fasting glucose, Dermatillomania, Body mass index increased, Hyperkinesia, Hepatitis viral, Dyskinesia, Blood triglycerides increased, Electrocardiogram QT prolonged, Dyssomnia, Orthostatic hypertension, Bruxism, Increased appetite, Excessive eye blinking, Pancreatitis chronic, Weight increased, Dyslipidaemia, Restless legs syndrome, Tongue biting, or Nuchal rigidity.

Compound 1, or a pharmaceutically acceptable salt thereof, does not have direct affinity for the D2 dopamine receptor. As described herein (e.g., in the Example below), Compound 1, or a pharmaceutically acceptable salt thereof, when administered to patients, did not cause the high incidence of adverse events and serious adverse events associated with typical or atypical antipsychotic agents that target the D2 dopamine receptor. Surprisingly, as described in the Examples herein (e.g., Example 1.1, Example 1.2), Compound 1 had robust efficacy, yet with an adverse event profile similar to placebo. In particular, the incidence of cardiovascular adverse events (including QT prolongation, orthostatic hypotension, orthostatic tachycardia), extrapyramidal adverse events, hyperprolactinemia, insomnia, anxiety, and headaches, experienced by patients was not clinically significant (i.e., less than, the same as, or about the same as or similar to placebo).

In some embodiments, the methods of the present disclosure minimize cardiovascular adverse events. In some embodiments, the method is substantially devoid of cardiovascular adverse events. In some embodiments, the risk of cardiovascular adverse events in the patient is about the same as or similar to placebo. In some embodiments, the method results in a cardiovascular event in less than or equal to 5% of patients. In some embodiments, the method results in a cardiovascular adverse event in less than or equal to 4.2% of patients. In some embodiments, the method results in a cardiovascular adverse event in less than or equal to 5% (e.g., less than or equal to 4.2%) of patients during a 29-day treatment period. In some embodiments, the method results in a cardiovascular event in less than or equal to 6% (e.g., less than or equal to 5.8%) of patients during a 26-week treatment period. In some embodiments, the method results in a cardiovascular adverse event in a percentage of patients that is no more than 1% greater than placebo.

In some embodiments, the patient has an elevated risk of a cardiovascular adverse event from administration of an antipsychotic agent that has direct affinity to dopamine D2 receptors. In some embodiments, the patient has a history of cardiovascular disease. In some embodiments, the patient has a history of a cardiovascular adverse event from a prior antipsychotic therapy. In some embodiments, the patient is susceptible to a cardiovascular adverse event from an antipsychotic agent that has direct affinity to dopamine D2 receptors.

In some embodiments, the patient is not actively monitored for cardiovascular adverse events during a treatment period. In some embodiments, the patient is not monitored by electrocardiography monitoring during a treatment period. In some embodiments, the patient is not warned about cardiovascular adverse events. In some embodiments, the patient is not concurrently treated for cardiovascular adverse events.

In some embodiments, a cardiovascular adverse event is characterized as atrial tachycardia, bradycardia, cardiovascular insufficiency, palpitations, postural tachycardia syndrome, increased blood pressure, hypertension, hypotension, or hot flush. In some embodiments, a cardiovascular adverse event is characterized as atrial tachycardia, bradycardia, cardiovascular insufficiency, palpitations, postural tachycardia syndrome, increased blood pressure, hypertension, hypotension, hot flush, QT prolongation, orthostatic hypotension, or orthostatic tachycardia.

In some embodiments, the methods of the present disclosure minimize extrapyramidal adverse events. In some embodiments, the method is substantially devoid of extrapyramidal adverse events. In some embodiments, the risk of extrapyramidal adverse events in the patient is about the same as or similar to placebo. In some embodiments, the method results in an extrapyramidal adverse event in less than or equal to 5% of patients. In some embodiments, the method results in an extrapyramidal adverse event in less than or equal to 3.3% of patients. In some embodiments, the method results in an extrapyramidal adverse event in less than or equal to 5% of patients during a 29-day treatment period. In some embodiments, the method results in an extrapyramidal adverse even in less than or equal to 5% (e.g., less than or equal to 3.2%) of patients during a 26-week treatment period. In some embodiments, the method results in an extrapyramidal adverse event in a percentage of patients that is no more than placebo.

In some embodiments, the patient has an elevated risk of an extrapyramidal adverse event from administration of an antipsychotic agent that has direct affinity to dopamine D2 receptors. In some embodiments, the patient has a history of an extrapyramidal adverse event from a prior antipsychotic therapy. In some embodiments, the patient is susceptible to an extrapyramidal adverse event from an antipsychotic agent that has direct affinity to dopamine D2 receptors.

In some embodiments, the patient is not warned about extrapyramidal adverse events.

In some embodiments, an extrapyramidal adverse event is characterized as akathisia, restlessness, joint stiffness, musculoskeletal stiffness, nuchal rigidity, postural tremor, or tremor.

In some embodiments, methods of the present disclosure minimize QT prolongation. In some embodiments, the method is substantially devoid of QT prolongation. In some embodiments, the risk of QT prolongation in the patient is about the same as or similar to placebo. In some embodiments, the method results in QT prolongation in less than or equal to 5% of patients. In some embodiments, the method results in QT prolongation in less than or equal to 1% of patients. In some embodiments, the method is substantially devoid of QT prolongation during a 29-day treatment period. In some embodiments, the method results in QT prolongation in a percentage of patients that is no more than placebo.

In some embodiments, the patient has an elevated risk of QT prolongation from administration of an antipsychotic agent. In some embodiments, the patient has a history of QT prolongation from a prior antipsychotic therapy. In some embodiments, the patient is susceptible to QT prolongation from an antipsychotic agent that has direct affinity to dopamine D2 receptors. In some embodiments, the patient has hypokalemia, Hepatitis C, HIV, T-wave abnormalities on electrocardiogram, is female, is geriatric, or is taking a second active agent known to increase risk of QT prolongation.

In some embodiments, the patient is not actively monitored for QT prolongation. In some embodiments, the patient is not warned about QT prolongation. In some embodiments, the patient is not concurrently treated for QT prolongation.

In some embodiments, QT prolongation is characterized as one or both of:
  a QTcF interval in the patient of greater than 450 msec at any time point not present at baseline; and
  an increase in QTcF interval from baseline of greater than or equal to 30 msec for at least one post-baseline measurement.

In some embodiments, QT prolongation is characterized as one or both of:
  a QTcF interval in the patient of greater than 450 msec at any time point not present at baseline if the patient is a male or greater than 470 msec at any time point not present at baseline if the patient is a female; and
  an increase in QTcF interval from baseline of greater than or equal to 30 msec for at least one post-baseline measurement.

In some embodiments, QT prolongation is characterized as one or both of:
  a QTcF interval in the patient of greater than 450 msec at any time point not present at baseline if the patient is a male or greater than 470 msec at any time point not present at baseline if the patient is a female; and
  an increase in QTcF interval from baseline of greater than or equal to 60 msec for at least one post-baseline measurement.

Prolongation of the QTc interval of the electrocardiogram (ECG) may be associated with the development of torsade de pointes, a ventricular arrhythmia that can cause syncope and may progress to ventricular fibrillation and sudden death. The average QTc interval in healthy adults is approximately 400 msec. A QTc interval of 500 msec or greater is considered to be a substantial risk factor for torsade de pointes.

In some embodiments, the methods of the present disclosure minimize hyperprolactinemia. In some embodiments, the method is substantially devoid of hyperprolactinemia. In some embodiments, the risk of hyperprolactinemia in the patient is about the same as or similar to placebo. In some embodiments, the method does not have a clinically significant risk of hyperprolactinemia. In some embodiments, the method is substantially devoid of hyperprolactinemia during a 29-day treatment period. In some embodiments, the method is substantially devoid of hyperprolactinemia during a 26-week treatment period. In some embodiments, the method results in hyperprolactinemia in a percentage of patients that is no more than placebo.

In some embodiments, the patient has an elevated risk of hyperprolactinemia from administration of an antipsychotic agent that has direct affinity to dopamine D2 receptors. In some embodiments, the patient has a history of hyperprolactinemia from a prior antipsychotic therapy. In some embodiments, the patient is susceptible to hyperprolactinemia from an antipsychotic agent that has direct affinity to dopamine D2 receptors.

In some embodiments, the patient is not actively monitored for hyperprolactinemia. In some embodiments, the patient is not warned about hyperprolactinemia. In some embodiments, the patient is not concurrently treated for hyperprolactinemia.

Hyperprolactinemia refers to significantly elevated levels of prolactin and is known to occur during administration of certain antipsychotic agents.

In some embodiments, the metabolic effects of the method are the same or similar to placebo, e.g., total cholesterol, HDL cholesterol, LDL cholesterol, triglycerides, and/or glucose levels in the patient are the same or similar to placebo. In some embodiments, the method does not result in clinically significant weight gain.

In some embodiments, the methods of the present disclosure minimize orthostatic hypotension. In some embodiments, the method is substantially devoid of orthostatic hypotension. In some embodiments, the risk of orthostatic hypotension in the patient is about the same as or similar to placebo. In some embodiments, the method results in orthostatic hypotension in less than or equal to 5% of patients. In some embodiments, the method results in orthostatic hypotension in less than or equal to 4.2% of patients. In some embodiments, the method results in orthostatic hypotension in less than or equal to 5% of patients during a 29-day treatment period. In some embodiments, the method results in orthostatic hypotension in a percentage of patients that is no more than placebo.

In some embodiments, the patient has an elevated risk of orthostatic hypotension from administration of an antipsychotic agent. In some embodiments, the patient has a history of orthostatic hypotension from a prior antipsychotic therapy. In some embodiments, the patient is susceptible to orthostatic hypotension from an antipsychotic agent that has direct affinity to dopamine D2 receptors.

In some embodiments, the patient is not actively monitored for orthostatic hypotension. In some embodiments, the patient is not warned about orthostatic hypotension. In some embodiments, the patient is not concurrently treated for orthostatic hypotension.

In some embodiments, the methods of the present disclosure minimize orthostatic tachycardia. In some embodiments, the method is substantially devoid of orthostatic tachycardia. In some embodiments, the risk of orthostatic tachycardia in the patient is about the same as or similar to placebo. In some embodiments, the method results in orthostatic tachycardia in less than or equal to 5% of patients. In some embodiments, the method results in orthostatic tachycardia in less than or equal to 4.2% of patients. In some embodiments, the method results in orthostatic tachycardia in less than or equal to 5% of patients during a 29-day treatment period. In some embodiments, the method results in orthostatic tachycardia in a percentage of patients that is no more than 2% greater than placebo.

In some embodiments, the patient has an elevated risk of orthostatic tachycardia from administration of an antipsychotic agent. In some embodiments, the patient has a history of orthostatic tachycardia from a prior antipsychotic therapy. In some embodiments, the patient is susceptible to orthostatic tachycardia from an antipsychotic agent that has direct affinity to dopamine D2 receptors.

In some embodiments, the patient is not actively monitored for orthostatic tachycardia. In some embodiments, the patient is not warned about orthostatic tachycardia. In some embodiments, the patient is not concurrently treated for orthostatic tachycardia.

Compound 1 is an antipsychotic agent with a non-D2 mechanism of action, which shows broad efficacy in animal models of psychosis and depression. As described in the Examples below, Compound 1 shows efficacy in the treatment of schizophrenia. Specifically, the efficacy measures of Positive and Negative Symptom Scale (PANSS) total score, PANSS subscores (negative, positive, general psychopathology), Clinical Global Impressions-Severity (CGI-S) score, Brief Negative Symptom Scale (BNSS) total score, and Montgomery-Asberg Depression Rating Scale (MADRS) total score each showed an improvement (e.g., compared to placebo) in patients suffering from an acute exacerbation of schizophrenia treated with Compound 1.

Accordingly, in some embodiments, the methods of the present disclosure result in one or more of:
  a reduction from baseline in PANSS total score of at least 17.2;
  an effect size in PANSS total score of at least 0.45;
  a reduction from baseline in PANSS positive subscale score of at least 5.5;
  an effect size in PANSS positive subscale score of at least 0.32;
  a reduction from baseline in PANSS negative subscale score of at least 3.1;
  an effect size in PANSS negative subscale score of at least 0.37;
  a reduction from baseline in PANSS general psychopathology subscale score of at least 9;
  an effect size in PANSS general psychopathology subscale score of at least 0.51;
  a reduction from baseline in CGI-S score of at least 1;
  an effect size in CGI-S score of at least 0.52;
  a reduction from baseline in BNSS total score of at least 7.1;
  an effect size in BNSS total score of at least 0.48;
  a reduction from baseline in MADRS total score of at least 3.3; and/or
  an effect size in MADRS total score of at least 0.32.

In some embodiments, a method described herein further comprises treating a symptom of insomnia, anxiety, or headache in the patient. In some embodiments, the risk of insomnia, anxiety, headache, or any combination thereof in the patient is less than placebo. In some embodiments, the method minimizes insomnia, anxiety, headache or any combination thereof.

In some embodiments, the symptom is insomnia. In some embodiments, the symptom is anxiety. In some embodiments, the symptom is headache. In some embodiments, a method described herein further comprises treating dizziness in the patient. In some embodiments, the risk of insomnia, anxiety, headaches, schizophrenia, somnolence, agitation, nausea, diarrhea and dyspepsia, individually and as a group, is not clinically significant (i.e., is less than, the same as, or about the same as or similar to placebo).

In some embodiments, Compound 1, or a pharmaceutically acceptable salt thereof, is administered once daily. In some embodiments, Compound 1, or a pharmaceutically acceptable salt thereof, is administered daily (e.g., once daily) for a 4-week treatment period. In some embodiments, Compound 1, or a pharmaceutically acceptable salt thereof, is administered daily (e.g., once daily) for a 29-day treatment period. In some embodiments, Compound 1, or a pharmaceutically acceptable salt thereof, is administered daily (e.g., once daily) for a period of one month or more (e.g., one, two, three, four, five, six, seven, eight, nine, ten, eleven or twelve months, or one, two, three, four or five years; chronically, on an ongoing basis). In some embodiments, Compound 1, or a pharmaceutically acceptable salt thereof, is administered orally. In some embodiments, Compound 1, or a pharmaceutically acceptable salt thereof, is administered in the evening or at night (e.g., once daily in the evening or at night). In some embodiments, Compound 1, or a pharmaceutically acceptable salt thereof, is administered at about bedtime (e.g., once daily at bedtime). In some embodiments, Compound 1, or a pharmaceutically acceptable salt thereof, is administered in the evening or at night at about bedtime (e.g., once daily in the evening or at night at bedtime). In some embodiments, Compound 1, or a pharmaceutically acceptable salt thereof, is administered at about the same time each day (e.g., about the same time each evening or each night, at about bedtime). In some embodiments, Compound 1, or a pharmaceutically acceptable salt thereof, is administered in a daily dose (e.g., daily titration dose, daily therapeutic dose) of from about 10 mg to about 250 mg, about 10 mg to about 200 mg, about 10 mg to about 150 mg, about 10 mg to about 100 mg, about 25 mg to about 100 mg, about 25 mg, about 50 mg, about 75 mg or about 100 mg.

In some embodiments, administering Compound 1, or a pharmaceutically acceptable salt thereof, comprises a titration period and a treatment period. In some examples, a first dose of Compound 1, or a pharmaceutically acceptable salt thereof, is administered during a titration period, followed by a therapeutic dose of Compound 1, or a pharmaceutically acceptable salt thereof, administered during a therapeutic period. In some examples, a second dose of Compound 1, or a pharmaceutically acceptable salt thereof, is administered after the first dose during the titration period and before the therapeutic dose, administered during the therapeutic period. The first dose can be less than the therapeutic dose. In some examples, the first dose is 50 mg per day, the second dose, if administered, is 75 mg/day, and the therapeutic dose is 50 mg per day, 75 mg per day or 100 mg per day. In some embodiments, the titration period is 3 days, followed by a therapeutic period (e.g., beginning on day 4 and continuing, e.g., through day 29, for six months or more, such as a year). In some embodiments, the titration period is 7 days, followed by a therapeutic period (e.g., beginning on day 8 and continuing, e.g., through day 29, for six months or more, such as a year). In some embodiments of a 7-day titration period, 50 mg/day of Compound 1, or a pharmaceutically acceptable salt thereof, is administered on days 1-3 and 75 mg/day of Compound 1, or a pharmaceutically acceptable salt thereof, is administered on days 4-7.

In some embodiments, the therapeutic dose can be down-titrated to a reduced dose (e.g., from a 100-mg dose to a 75-mg dose, from a 75-mg dose to a 50-mg dose, from a 50-mg dose to a 25-mg dose). In some examples, a 75-mg dose can be reduced to a 50-mg dose. In some embodiments, Compound 1, or a pharmaceutically acceptable salt thereof, is administered as a flexible dose of from about 25 mg daily to about 100 mg daily (e.g., about 25 mg daily, about 50 mg daily, about 75 mg daily or about 100 mg daily).

In some embodiments, provided is a method of treating schizophrenia in a patient, comprising administering to the patient Compound 1, or a pharmaceutically acceptable salt thereof, daily at a first dose for 1 to 3 days, followed by administering to the patient Compound 1, or a pharmaceutically acceptable salt thereof, daily at a therapeutic dose, wherein the first dose is less than the therapeutic dose. In some embodiments, Compound 1, or a pharmaceutically acceptable salt thereof, is administered daily at the first dose on days 1-3, and Compound 1, or a pharmaceutically acceptable salt thereof, is administered daily after day 3 at the therapeutic dose (e.g., on days 4-29). In some embodiments, the first dose is 50 mg and the therapeutic dose is 75 mg. In some embodiments, Compound 1, or a pharmaceutically acceptable salt thereof, is administered once daily. In some embodiments, Compound 1, or a pharmaceutically acceptable salt thereof, is administered orally (e.g., once daily). In some embodiments, Compound 1, or a pharmaceutically acceptable salt thereof, is administered in the evening or at night, (e.g., once daily in the evening or at night). In some embodiments, Compound 1, or a pharmaceutically acceptable salt thereof, is administered at about bedtime (e.g., once daily at bedtime). In some embodiments, Compound 1, or a pharmaceutically acceptable salt thereof, is administered in the evening or at night at about bedtime (e.g., once daily in the evening or at night at bedtime). In some embodiments, Compound 1, or a pharmaceutically acceptable salt thereof, is administered at about the same time each day (e.g., about the same time each evening or night at about bedtime).

In some embodiments, provided is a method of treating schizophrenia in a patient, comprising administering to the patient 50 mg daily of Compound 1, or a pharmaceutically acceptable salt thereof. In some embodiments, Compound 1, or a pharmaceutically acceptable salt thereof, is administered once daily. In some embodiments, Compound 1, or a pharmaceutically acceptable salt thereof, is administered daily for a 29-day treatment period. In some embodiments, Compound 1, or a pharmaceutically acceptable salt thereof, is administered daily for a period of six months or more (e.g., seven, eight, nine, ten, eleven or twelve months, or one, two, three, four or five years). In some embodiments, Compound 1, or a pharmaceutically acceptable salt thereof, is administered orally. In some embodiments, Compound 1, or a pharmaceutically acceptable salt thereof, is administered in the evening or at night (e.g., once daily in the evening or at night). In some embodiments, Compound 1, or a pharmaceutically acceptable salt thereof, is administered at about bedtime (e.g., once daily at bedtime). In some embodiments, Compound 1, or a pharmaceutically acceptable salt thereof, is administered in the evening or at night at about bedtime (e.g., once daily in the evening or at night at bedtime). In some embodiments, Compound 1, or a pharmaceutically acceptable salt thereof, is administered at about the same time each day (e.g., about the same time each evening or each night, at about bedtime).

In some embodiments, provided is a method of treating schizophrenia in a patient, comprising:
  orally administering or having administered to the patient 75 mg daily of Compound 1, or a pharmaceutically acceptable salt thereof, during a treatment period;
  determining or having determined if the patient has experienced an adverse event during the treatment period; and
  reducing or having reduced administration to 50 mg daily of Compound 1, or a pharmaceutically acceptable salt thereof, if the patient experiences an adverse event during the treatment period.

In some embodiments, the method further comprises monitoring the patient for an adverse event during the treatment period.

In some embodiments, provided is a method of treating schizophrenia in a patient, comprising orally administering to the patient a therapeutically effective amount of Compound 1, or a pharmaceutically acceptable salt thereof, to achieve a maximum plasma concentration of Compound 1, or a pharmaceutically acceptable salt thereof, in the patient at 1-4 hours after a single dose and at 2-4 hours after multiple doses, wherein the therapeutically effective amount is 50 mg or 75 mg daily.

In some embodiments, provided is a method of treating schizophrenia in a patient, comprising orally administering to the patient a therapeutically effective amount of Compound 1, or a pharmaceutically acceptable salt thereof, to achieve a steady-state plasma concentration of Compound 1, or a pharmaceutically acceptable salt thereof, in a patient within 7 days, wherein the therapeutically effective amount is 50 mg or 75 mg daily.

In some embodiments, provided is a method of treating a symptom of insomnia, anxiety, or headache, in a patient having schizophrenia, comprising administering to the patient a therapeutically effective amount of Compound 1, or a pharmaceutically acceptable salt thereof. In some embodiments, the symptom is insomnia. In some embodiments, the symptom is anxiety. In some embodiments, the symptom is headache.

In some embodiments, provided is a method of treating insomnia, anxiety, or headache, associated with schizophrenia in a patient, comprising administering to the patient a therapeutically effective amount of Compound 1, or a pharmaceutically acceptable salt thereof.

In some embodiments, provided is a method of treating schizophrenia in a patient, comprising administering to the patient a therapeutically effective amount of Compound 1, or a pharmaceutically acceptable salt thereof, wherein the incidence of insomnia, anxiety, or headache, or any combination thereof in patients is less than placebo.

In some embodiments, provided is a method of reducing PANSS total score in a patient suffering from schizophrenia, comprising administering to the patient a therapeutically effective amount of Compound 1, or a pharmaceutically acceptable salt thereof, wherein the method results in (i) a reduction from baseline in PANSS total score of at least 17.2 or (ii) an effect size in PANSS total score of at least 0.45.

In some embodiments, provided is a method of reducing CGI-S score in a patient suffering from schizophrenia, comprising administering to the patient a therapeutically effective amount of Compound 1, or a pharmaceutically acceptable salt thereof, which produces (i) a reduction from baseline in CGI-S score of at least 1 or (ii) an effect size in CGI-S score of at least 0.52.

In some embodiments, provided is a method of reducing BNSS total score in a patient suffering from schizophrenia, comprising administering to the patient a therapeutically effective amount of Compound 1, or a pharmaceutically acceptable salt thereof, which produces (i) a reduction from baseline in BNSS total score of at least 7.1 or (ii) an effect size in BNSS total score of at least 0.48.

In some embodiments, provided is a method of reducing MADRS total score in a patient suffering from schizophrenia, comprising administering to the patient a therapeutically effective amount of Compound 1, or a pharmaceutically acceptable salt thereof, which produces (i) a reduction from baseline in MADRS total score of at least 3.3 or (ii) an effect size in MADRS total score of at least 0.32.

In some embodiments, Compound 1, or a pharmaceutically acceptable salt thereof, may be administered as part of a pharmaceutical composition. Pharmaceutical compositions of the present disclosure may be administered orally, parenterally, by inhalation, topically, rectally, nasally, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In some embodiments, the compositions are administered orally, intraperitoneally or intravenously. Sterile injectable forms of the compositions of the present disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, such as, for example, as a solution in 1,3-butanediol.

In some embodiments, pharmaceutically acceptable compositions of this disclosure may be orally administered in any orally acceptable dosage form including capsules, tablets, aqueous suspensions or solutions.

In some embodiments, the pharmaceutical compositions of the present disclosure comprise one or more pharmaceutically acceptable excipients, including one or more binders, bulking agents, buffers, stabilizing agents, surfactants, wetting agents, lubricating agents, diluents, disintegrants, viscosity enhancing or reducing agents, emulsifiers, suspending agents, preservatives, antioxidants, opaquing agents, glidants, processing aids, colorants, sweeteners, taste-masking agents, perfuming agents, flavoring agents, diluents, polishing agents, polymer matrix systems, plasticizers and other known additives to provide an elegant presentation of the drug or aid in the manufacturing of a medicament or pharmaceutical product comprising a composition of the present disclosure. Examples of carriers and excipients well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005.

In some embodiments, non-limiting examples of excipients include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), hydroxypropyl cellulose, titanium dioxide, talc, calcium carbonate (e.g., granules or powder), microcrystalline cellulose, powdered cellulose, dextrates, kaolin, silicic acid, sorbitol, starch, pre-gelatinized starch, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), colorants and mixtures thereof.

In some embodiments, pharmaceutical compositions are formulated with one or more pharmaceutically acceptable excipients in accordance with known and established practice. Thus, in some embodiments the compositions are formulated as, for example, a liquid, powder, elixir, injectable solution, or suspension.

In some embodiments, formulations for oral use may be provided as tablets, caplets, or capsules, wherein the pharmacologically active ingredients are mixed with an inert solid diluent.

In some embodiments, the oral dosage form is a solid oral dosage form. In some embodiments the solid oral dosage form comprises a tablet, and in some embodiments the solid oral dosage form comprises a capsule. Tablets may also include granulating and disintegrating agents, and may be coated or uncoated.

In some embodiments, formulations for topical use may be provided, for example as topical solutions, lotions, creams, ointments, gels, foams, patches, powders, solids, sponges, tapes, vapors, pastes or tinctures.

In some embodiments, a suitable daily dose of Compound 1, or a pharmaceutically acceptable salt thereof, will be that amount of the compound which is the lowest dose effective to produce a therapeutic effect. Such an effective dose will generally depend upon the factors described herein, or as understood by one having ordinary skill in the art. Generally, oral, intravenous and subcutaneous doses of Compound 1, or a pharmaceutically acceptable salt thereof, for a patient will range from about 0.005 mg per kilogram to about 5 mg per kilogram of body weight per day. In some embodiments, the oral dose of Compound 1, or a pharmaceutically acceptable salt thereof, will range from about 0.125 mg per kilogram of body weight to about 2.5 mg per kilogram of body weight per day. In some embodiments, the oral dose of Compound 1, or a pharmaceutically acceptable salt thereof, will range from about 0.25 mg per kilogram of body weight to about 2.5 mg per kilogram of body weight per day. In some embodiments, the oral dose of Compound 1, or a pharmaceutically acceptable salt thereof, will range from about 0.125 mg per kilogram of body weight to about 1.125 mg per kilogram of body weight per day. In some embodiments, the oral dose of Compound 1, or a pharmaceutically acceptable salt thereof, will range from about 10 mg to about 300 mg per day. In another embodiment, the oral dose of Compound 1, or a pharmaceutically acceptable salt thereof, will range from about 20 mg to about 250 mg per day. In another embodiment, the oral dose of Compound 1, or a pharmaceutically acceptable salt thereof, will range from about 100 mg to about 300 mg per day. In another embodiment, the oral dose of Compound 1, or a pharmaceutically acceptable salt thereof, will range from about 10 mg to about 100 mg per day. In another embodiment, the oral dose of Compound 1, or a pharmaceutically acceptable salt thereof, will range from about 50 mg to about 75 mg per day. In another embodiment, the oral dose of Compound 1, or a pharmaceutically acceptable salt thereof, will range from about 50 mg to about 200 mg per day. Each of the above-recited dosage ranges may be formulated as a single or multiple unit dosage formulations.

In some embodiments, Compound 1, or a pharmaceutically acceptable salt thereof, is administered orally. In some embodiments, Compound 1, or a pharmaceutically acceptable salt thereof, is administered daily. In some embodiments, Compound 1, or a pharmaceutically acceptable salt thereof, is administered at about 50 mg or about 75 mg per day.

In some embodiments, the method achieves a maximum plasma concentration of Compound 1, or a pharmaceutically acceptable salt thereof, in the patient at 1-4 hours after a single oral dose and at 2-4 hours after multiple oral doses. In some embodiments, the method achieves a maximum plasma concentration of Compound 1, or a pharmaceutically acceptable salt thereof, in the patient at 1-4 hours after a single oral dose. In some embodiments, the method achieves a maximum plasma concentration of Compound 1, or a pharmaceutically acceptable salt thereof, in the patient at 2-4 hours after multiple oral doses.

In some embodiments, the method achieves a steady-state plasma concentration of Compound 1, or a pharmaceutically acceptable salt thereof, in the patient within 7 days.

In some embodiments, Compound 1, or a pharmaceutically acceptable salt thereof, is administered daily during a 29-day treatment period.

In some embodiments, Compound 1, or a pharmaceutically acceptable salt thereof, may be used in combination with one or more second active agents to treat, prevent, and/or manage diseases and disorders described herein.

Some embodiments of the disclosure include methods of treating neurological and psychiatric diseases and disorders comprising administering to a patient a therapeutically effective amount of Compound 1, or a pharmaceutically acceptable salt thereof. Some embodiments include methods of preventing or managing neurological and psychiatric diseases and disorders comprising administering to a patient a therapeutically effective amount of Compound 1, or a pharmaceutically acceptable salt thereof, to prevent or manage the disease.

The Diagnostic and Statistical Manual of Mental Disorders, Fifth Ed., hereinafter, the "DSM-5"), published by the American Psychiatric Association in 2013, and as subsequently amended, provides a standard diagnostic system upon which persons of skill rely for diagnosis of various diseases and disorders.

The term "mood disorder" as used herein includes depression, major depression, major depressive disorder, mild depression, severe depression without psychosis, severe depression with psychosis, melancholia (formerly endogenous depression), atypical depression, dysthymic disorder, manic depression, bipolar disorder, bipolar depression, bipolar I disorder, bipolar II disorder, bipolar III disorder, cyclothymic disorder, and chronic hypomania.

Psychiatric disorders are pathological conditions of the brain characterized by identifiable symptoms that result in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity. Mood disorders are a type of psychiatric disorder often defined as a group of heterogeneous, typically recurrent illnesses including unipolar (depressive) and bipolar (manic-depressive) disorders characterized by pervasive mood disturbances, psychomotor dysfunction, and vegetative symptoms. Suicide, the most serious complication in patients with mood disorders, is the cause of death in 15 to 25% of untreated patients with mood disorders; unrecognized or inadequately treated depression contributes to 50 to 70% of all completed suicides.

In some embodiments, the neurological disorder is: depression (e.g., major depressive disorder or dysthymia); bipolar disorder, seasonal affective disorder; cognitive deficit; fibromyalgia; pain (e.g., neuropathic pain); sleep related disorder (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; post-traumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic disorder; dysthymic disorder; cyclothymic disorder; obesity; and substance abuse or dependency (e.g., cocaine addiction, nicotine addiction). In another embodiment, Compound 1, or a pharmaceutically acceptable salt thereof, is useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, epilepsy, disturbances of consciousness, coma, lowering of attention, speech disorder, Lennox syndrome, autism, and hyperkinetic syndrome.

In some embodiments, the disease or disorder which the methods of the present disclosure treat comprises one of more of a mood disorder, bipolar disorder (BPD), bipolar depression, sleep disorders, REM behavior disorder, psychosis disorders, Alzheimer's disease with agitation and/or psychosis, Parkinson's disease psychosis, schizophrenia, attenuated psychosis syndrome, prodromal schizophrenia, and schizoaffective disorder.

In some embodiments, the neurological or psychiatric disease or disorder is one or more of a mood disorder, bipolar disorder (BPD), bipolar depression, sleep disorders, REM behavior disorder, psychosis disorders, Alzheimer's disease with agitation and/or psychosis, Parkinson's disease psychosis, schizophrenia, attenuated psychosis syndrome, prodromal schizophrenia, and schizoaffective disorder.

In some embodiments, the neurological or psychiatric disease or disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychoaffective disorder, aggression, delirium, Parkinson's psychosis, excitative psychosis, psychotic disorder due to a general medical condition, substance-induced or drug-induced (e.g., phencyclidine, ketamine and other dissociative anesthetics, amphetamine and other psychostimulants and cocaine) psychosis disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); and Alzheimer's disease with agitation and/or psychosis.

In some embodiments, the neurological or psychiatric disease or disorder is selected from a depressive disorder including, but not limited to, unipolar depression, seasonal depression, post-partum depression, atypical depression, catatonic depression, elderly depression, endogenous depression, melancholic depression, perinatal depression, situational depression, chronic depression, bipolar depression, major depressive disorder (MDD), major depressive disorder with mixed features (MDD-MF), treatment resistant depression (TRD), and dysthymia, and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders.

In some embodiments, the neurological or psychiatric disease or disorder is selected from a bipolar disorder including, but not limited to, bipolar depression, bipolar I disorder, bipolar II disorder, cyclothymic disorder, substance/medication-induced bipolar and related disorders, bipolar and related disorder due to another medical condition, other specified bipolar and related disorder, and unspecified bipolar and related disorders.

In some embodiments, the neurological or psychiatric disease or disorder is selected from an eating disorder including, but not limited to, eating disorders such as obesity, bulimia nervosa, pica and compulsive eating disorders.

In some embodiments, the neurological or psychiatric disease or disorder is selected from a sleep disorder including, but not limited to, insomnia, disturbed sleep, jet lag, hypersomnia, cataplexy, sleep apnea, obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

In some embodiments, the neurological or psychiatric disease or disorder is a bipolar disorder. Bipolar disorders (including both bipolar I and bipolar II) are serious psychiatric disorders that have a prevalence of approximately 2% of the population and affect both genders alike. They are relapsing-remitting conditions characterized by cycling between elevated (i.e., manic) and depressed moods, which distinguishes them from other disorders such as major depressive disorder and schizophrenia.

Bipolar I is defined by the occurrence of a full manic episode, although most individuals experience significant depression. Symptoms of mania include elevated or irritable mood, hyperactivity, grandiosity, decreased need for sleep, racing thoughts, and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although patients spend considerably more time in the depressive state. Other related conditions include cyclothymic disorder.

In bipolar II disorder, depressive episodes alternate with hypomanias (relatively mild, nonpsychotic periods of usually <1 week). During the hypomanic period, mood brightens, the need for sleep decreases, and psychomotor activity accelerates beyond the patient's usual level. Often, the switch is induced by circadian factors (e.g., going to bed depressed and waking early in the morning in a hypomanic state). Hypersomnia and overeating are characteristic and may recur seasonally (e.g., in autumn or winter); insomnia and poor appetite occur during the depressive phase. For some persons, hypomanic periods are adaptive because they are associated with high energy, confidence, and supernormal social functioning. Many patients who experience pleasant elevation of mood, usually at the end of a depression, do not report it unless specifically questioned.

Patients with major depressive episodes and a family history of bipolar disorders (unofficially called bipolar III) often exhibit subtle hypomanic tendencies; their temperament is termed hyperthymic (i.e., driven, ambitious, and achievement-oriented).

In cyclothymic disorder, less severe hypomanic and mini-depressive periods follow an irregular course, with each period lasting a few days. Cyclothymic disorder is commonly a precursor of bipolar II disorder. But it can also occur as extreme moodiness without being complicated by major mood disorders. In such cases, brief cycles of retarded depression accompanied by low self-confidence and increased sleep alternate with elation or increased enthusiasm and shortened sleep. In another form, low-grade depressive features predominate; the bipolar tendency is shown primarily by how easily elation or irritability is induced by antidepressants. In chronic hypomania, a form rarely seen clinically, elated periods predominate, with habitual reduction of sleep to <6 hours. Persons with this form are constantly overcheerful, self-assured, overenergetic, full of plans, improvident, overinvolved, and meddlesome; they rush off with restless impulses and accost people.

Accordingly, in some embodiments, the neurological or psychiatric disease or disorder is one or more of bipolar I disorder, bipolar II disorder, cyclothymic disorder, other specified bipolar and related disorder, or unspecified bipolar and related disorder, and bipolar I disorder or bipolar II disorder with the specifiers of anxious distress, with mixed features, with rapid cycling, with melancholic features, with atypical features, with mood-congruent psychotic features, with mood incongruent psychotic features, with catatonia, with peripartum onset, and/or with seasonal pattern. A recent article by Hu et al [*Prim Care Companion CNS Disord.* 2014; 16(2): PCC.13r01599] highlights that bipolar disorder, while commonly encountered in the primary care setting, is often misdiagnosed or undiagnosed. The DSM-5 attempts to capture the large proportion of patients with subsyndromal mixed symptoms with the inclusion of the mixed specifier.

In some embodiments, the neurological or psychiatric disease or disorder is a depressive disorder. Depressive disorders include, but are not limited to, unipolar depression, seasonal depression, post-partum depression, atypical depression, catatonic depression, elderly depression, endogenous depression, melancholic depression, perinatal depression, situational depression, chronic depression, bipolar depression, major depressive disorder (MDD), major depressive disorder with mixed features (MDD-MF), treatment resistant depression (TRD), and dysthymia, and are associated with depressed mood (sadness), poor concentration, insomnia, fatigue, appetite disturbances, excessive guilt and thoughts of suicide, premenstrual syndrome (PMS) and premenstrual dysphoric disorder (PDD), mood disorders due to a general medical condition, and substance-induced mood disorders.

Depression is an affective disorder, the pathogenesis of which cannot be explained by any single cause or theory. Unfortunately, treatment options for depressed patients who have suboptimal clinical responses to therapy with an antidepressant are limited. Approximately thirty percent (30%) of patients initiating antidepressant therapy show suboptimal or delayed clinical responses to the first-line antidepressant agents that are commonly used to treat depression.

Typically, if a patient exhibits suboptimal or delayed clinical response after several weeks of therapy with an antidepressant, the clinician's initial approach is to increase the dose of the antidepressant. If the patient's response remains unsatisfactory after increasing the dose, the most common approaches that many clinicians will pursue are: a) switching to another antidepressant; or b) adding a second antidepressant; or c) attempting an augmentation therapy by administering agents such as lithium carbonate, thyroid hormone (triiodothyronine), psychostimulants, modafinil, atypical antipsychotics, buspirone, or pindolol.

In its full syndromal expression, clinical depression manifests as major depressive disorder, with episodic course and varying degrees of residual manifestations between episodes. The mood is typically depressed, irritable, and/or anxious. The patient may appear miserable, with furrowed brows, downturned corners of the mouth, slumped posture, poor eye contact, and monosyllabic (or absent) speech. The morbid mood may be accompanied by preoccupation with guilt, self-denigrating ideas, decreased ability to concentrate, indecisiveness, diminished interest in usual activities, social withdrawal, helplessness, hopelessness, and recurrent thoughts of death and suicide. Sleep disorders are common. In some, the morbid mood is so deep that tears dry up; the patient complains of an inability to experience usual emotions—including grief, joy, and pleasure—and of a feeling that the world has become colorless, lifeless, and dead.

Melancholia (formerly endogenous depression) is characterized by marked psychomotor slowing (of thinking and activity) or agitation (e.g., restlessness, wringing of the hands, pressure of speech), weight loss, irrational guilt, and loss of the capacity to experience pleasure. Mood and activity vary diurnally, with a nadir in the morning. Most melancholic patients complain of difficulty falling asleep, multiple arousals, and insomnia in the middle of the night or early morning. Sexual desire is often diminished or lost. Amenorrhea can occur. Anorexia and weight loss may lead to emaciation and secondary disturbances in electrolyte balance.

In atypical depression, reverse vegetative features dominate the clinical presentation; they include anxious-phobic symptoms, evening worsening, initial insomnia, hypersomnia that often extends into the day, and hyperphagia with weight gain. Unlike patients with melancholia, those with atypical depression show mood brightening to potentially positive events but often crash into a paralyzing depression with the slightest adversity. Atypical depressive and bipolar II disorders overlap considerably.

In dysthymic disorder, depressive symptoms typically begin insidiously in childhood or adolescence and pursue an intermittent or low-grade course over many years or decades; major depressive episodes may complicate it (double depression). In pure dysthymia, depressive manifestations occur at a subthreshold level and overlap considerably with those of a depressive temperament: habitually gloomy, pessimistic, humorless, or incapable of fun; passive and lethargic; introverted; skeptical, hypercritical, or complaining; self-critical, self-reproaching, and self-derogatory; and preoccupied with inadequacy, failure, and negative events.

Thorough evaluation of many persons with depression reveals bipolar traits, and as many as one in five patients with a depressive disorder also develops frank hypomania or mania. Most switches from unipolar to bipolar disorder occur within 5 years of the onset of depressive manifestations. Predictors of a switch include early onset of depression (<25 years old), postpartum depression, frequent episodes of depression, quick brightening of mood with somatic treatments (e.g., antidepressants, phototherapy, sleep deprivation, electroconvulsive therapy), and a family history of mood disorders for three consecutive generations.

Between episodes, patients with bipolar disorder exhibit depressive moodiness and sometimes high-energy activity; disruption in developmental and social functioning in bipolar depression is more common than in unipolar disorder. In bipolar disorder, depression episodes are shorter (3 to 6 months), age of onset is younger, onset of episodes is more abrupt, and cycles (time from onset of one episode to that of the next) are shorter than in unipolar disorder. Cyclicity is particularly accentuated in rapid-cycling forms of bipolar disorder (usually defined as >=4 episodes/year). In addition depressive episodes in bipolar disorder are a difficult component of BPD to treat. For example, psychiatrists indicate that about 25% of patients across all bipolar disorders are refractory during a manic episode, while about 70% are refractory during a depressive episode.

Accordingly, in some embodiments, the neurological or psychiatric disease or disorder is one or more of bipolar depression, major depressive disorder (MDD), persistent depressive disorder (Dysthymia), premenstrual dysphoric disorder (PMDD), major depressive disorder with mixed features (MDD-MF), depressive disorder due to another medical condition, other specified depressive disorder, unspecified depressive disorder, or treatment resistant depression (TRD), and MDD with the specifiers of anxious distress, with mixed features, with melancholic features, with atypical features, with mood-congruent psychotic features, with mood-incongruent psychotic features, with catatonia, with peripartum onset, and/or with seasonal pattern, and seasonal affective disorder.

It is to be understood that TRD is a term used in clinical psychiatry to describe cases of major depressive disorder (MDD) that do not respond adequately to appropriate courses of at least two antidepressants.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, the compositions and methods of the present disclosure do not increase the risk of suicidal thinking and/or behavior in children, adolescents and/or young adults with a depressive disorder, e.g., with MDD. In some embodiments, the present disclosure provides medicaments for and provides methods of treating one or more symptoms of a depressive disorder (e.g., MDD) in children, adolescents and/or young adults without increasing the risk of suicidal thinking and/or behavior.

In some embodiments, the neurological or psychiatric disease or disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making.

Accordingly, in some embodiments, the neurological or psychiatric disease or disorder is one or more of schizotypal (personality) disorder, delusional disorder, brief psychotic disorder, schizophreniform disorder, schizophrenia, schizoaffective disorder, substance/medication-induced psychotic disorder, psychotic disorder due to another medical condition, other specified schizophrenia spectrum and other psychotic disorder, unspecified schizophrenia spectrum, and other psychotic disorder.

It is to be understood that schizoaffective disorder includes a condition that includes aspects of both schizophrenia and a mood disorder, such as, for example, a major depressive disorder, a bipolar disorder, etc.

In some embodiments, the neurological or psychiatric disease or disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; and stressor-related disorders, including reactive attachment disorder, disinhibited social engagement disorder, posttraumatic stress disorder (PTSD), acute stress disorder, and adjustment disorders.

In some embodiments, the neurological or psychiatric disease or disorder is a sleep disorder including those sleep disorders which are produced by psychiatric conditions, including, but not limited to, insomnia, disturbed sleep, jet lag, hypersomnia, cataplexy, sleep related disorder (e.g., sleep apnea, insomnia, narcolepsy, cataplexy), obstructive sleep apnea, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

In some embodiments, the neurological or psychiatric disease or disorder is a social function disorder. In some embodiments, the social function disorder is a neurodevelopmental disorder, an obsessive-compulsive disorder or a disruptive, impulse-control and conduct disorder. In some embodiments, the social function disorder is a language disorder, a speech sound disorder, a childhood-onset fluency disorder (stuttering), a social communication disorder, a developmental coordination disorder, a stereotypical movement disorder, a tic disorder, Tourette's disorder, a persistent (chronic) motor or vocal tic disorder, a provisional tic disorder, another specified tic disorder, an unspecified tic disorder, an obsessive-compulsive disorder, or an impulse-control disorder. In some embodiments, the social function disorder is a language disorder, a speech sound disorder, a childhood-onset fluency disorder (stuttering), a social communication disorder, a developmental coordination disorder, a stereotypical movement disorder, a tic disorder, Tourette's disorder, a persistent (chronic) motor or vocal tic disorder, a provisional tic disorder, another specified tic disorder, or an unspecified tic disorder. In some embodiments, the social function disorder is a language disorder, a speech sound disorder, a childhood-onset fluency disorder (stuttering), or a social communication disorder. In some embodiments, the social function disorder is a language disorder, childhood-onset fluency disorder (stuttering), social communication disorder, developmental coordination disorder, stereotypical movement disorder, persistent (chronic) motor or vocal tic disorder, provisional tic disorder, other specified tic disorder, or unspecified tic disorder.

Combination Therapy

In some embodiments, compounds disclosed herein provide a method of treating a neurological and/or psychiatric disease or disorder described herein, comprising administering a compound disclosed herein in conjunction with one or more pharmaceutical agents. Suitable pharmaceutical agents that may be used in combination with the compounds of the present invention include anti-Parkinson's drugs, anti-Alzheimer's drugs, anti-depressants, anti-psychotics, anti-ischemics, CNS depressants, anti-cholinergics, nootropics, epilepsy medication, attention (e.g., ADD/ADHD) medications, sleep-promoting medications, wakefulness-promoting medications, and pain medications.

Suitable anti-Parkinson's drugs include dopamine replacement therapy (e.g. L-DOPA, carbidopa, COMT inhibitors such as entacapone or tolcapone), dopamine agonists (e.g. D1 agonists, D2 agonists, mixed D1/D2 agonists, bromocriptine, pergolide, cabergoline, ropinirole, pramipexole, piribedil, or apomorphine in combination with domperidone), histamine H2 antagonists, monoamine oxidase inhibitors (such as selegiline, rasagiline, safinamide and tranylcypromine), certain atypical antipsychotics such as pimavanserin (a non-dopaminergic atypical antipsychotic and inverse agonist of the serotonin 5-$HT_{2A}$ receptor), and amantadine.

In some embodiments, compounds of the invention can be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone or tolcapone, MAO A/B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, cholinesterase inhibitors such as donepezil, galantamine or rivastigmine, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine, duloxetine; aprepitant; bupropion, vilazodone, mirtazapine, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, reboxetine, vortioxetine, clorazepate, and ketamine and pharmaceutically acceptable salts thereof. In some embodiments, suitable anti-depressant and anti-anxiety agents are tianeptine, or pharmaceutically acceptable salts thereof.

Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, perphenazine, thioridazine, trifluoperazine, aripiprazole, asenapine, clozapine, olanzapine, paliperidone, brexpiprazole, paliperidone, cariprazine, pimavanserin, iloperidone, lumateperone, MIN-101, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid, iloperidone, thiothixene, gabapentin, tiagabine and pharmaceutically acceptable salts thereof.

Suitable epilepsy medications include levetiracetam, oxcarbazepine, clobazam, retigabine, zonisamide, felbamate, esclicarbazepine acetate, lacosamide, carbamazepine, tiagabine, methsuximide, progabide, valproic acid, lamotrigine, brivaracetam, rufinamide, topiramate and perampanel.

Suitable attention medications include methyl phenidate, atomoxetine, guanfacine, D-amphetamine, lisdexamphetamine, methylamphetamine, and clonidine.

Suitable sleep-promoting medications include ramelteon, triazolam, zopiclone, eszopiclone, zolpidem, temazepam, and trazodone.

Suitable wakefulness-promoting medications include Modafinil, D-Amphetamine, caffeine, and armodafinil.

Suitable pain medications include dextromethorphan, tapentadol, buprenorphine, codeine, fentanyl, hydrocodone, hydromorphone, morphine, naloxegol, oxycodone, tramadol, gabapentil, difluprednate, pregabalin, acetyl salicyclic acid, bromfenac, diclofenac, diflunisal, indomethacin, ketorolac, meoxican, and naproxen.

In some embodiments, compounds and compositions disclosed herein may be used in combination with other therapies. Suitable therapies include psychotherapy, cognitive behavioral therapy, electroconvulsive therapy, transcranial magnetic stimulation, vagus nerve stimulation, and deep-brain stimulation.

EXAMPLES

Example 1.1: 4—Week Clinical Study

Compound 1 was evaluated in acutely psychotic adult subjects with schizophrenia to study its efficacy and safety in a 4-week, randomized, double-blind, parallel-group, placebo-controlled, flexibly-dosed, multicenter trial. Hospitalized patients (male and female) aged 18 to 40 years of age (inclusive) were eligible for enrollment if they met the inclusion criteria. Inclusion criteria included:
1. Subject met DSM-5 criteria for schizophrenia, as established by clinical interview (using the DSM-5 as a reference and confirmed using the SCID-CT), with a duration of illness of greater than or equal to six months, whether treated or untreated,
2. Subject had CGI-S score ≥4 (moderate or greater) at screening and baseline (Day 1),
3. Subject had PANSS total score ≥80 and a PANSS item score ≥4 on 2 or more of the following PANSS items: delusions, conceptual disorganization, hallucinations and unusual thought content at screening and baseline (Day 1),
4. Subject was experiencing an acute exacerbation of psychotic symptoms (with a duration of no longer than two months), as evidenced by (i) marked deterioration of functioning in one or more areas, such as occupational, social, or personal care or hygiene; and (ii) requiring hospitalization for an acute psychotic exacerbation at the time of screening or has been hospitalized for the purpose of treating an acute psychotic exacerbation for no more than two consecutive weeks immediately before screening,
5. Subject had no more than two prior hospitalizations for the treatment of an acute exacerbation of schizophrenia (not including the current hospitalization),
6. At baseline, subject had a total score <5 on the SAS.

Patients were excluded from the study if they met any of the following exclusion criteria:
1. Subject answered "yes" to suicidal ideation Item 4 (active suicidal ideation with some intent to act, without specific plan) or Item 5 (suicidal ideation with specific plan and intent) on the C-SSRS assessment or at or during the screening period (e.g., in the past one month) and/or at baseline,
2. Subject previously received Compound 1,
3. Subject had a lifelong history or presence of symptoms consistent with a major psychiatric disorder other than schizophrenia as defined by DSM-5, including, but not limited to, alcohol use disorder (within the past 12 months), substance (other than nicotine or caffeine) use disorder within past 12 months, major depressive disorder, bipolar depression, mania, schizoaffective disorder, obsessive compulsive disorder, posstraumatic stress disorder,
4. Subject was at significant risk of harming self, others, or objects based on investigator's judgment,
5. Subject had attempted suicide within three months prior to screening,
6. Subject was involuntarily hospitalized,
7. Subject was receiving a total dose of antipsychotic medication equivalent to ≥12.0 mg/day of haloperidol at screening, except subject may be eligible if such treatment is less than two weeks in duration,
8. Subject had received electroconvulsive therapy (ECT) within the six months prior to screening or is expected to require ECT during the study,
9. Subject was judged to be resistant to antipsychotic treatment by the investigator, based on failure to respond to two or more marketed antipsychotic agents, given at adequate dose for at least four weeks within a one-year period prior to screening,
10. Subject had a history of treatment with clozapine for refractory psychosis and/or subject has been treated with clozapine (for any reason) within four months of screening,
11. Subject was currently participating, or had participated in, a study with an investigational or marketed compound or device within six months prior to signing the informed consent, or had participated in two or more studies within 24 months prior to signing informed consent,
12. Subject had received depot antipsychotics unless the last injection was at least one treatment cycle or at least 30 days (whichever was longer), prior to the screening phase.

To qualify for randomization, patients met the following randomization criteria:
1. Subject had a PANSS total score ≥80 at baseline (Day 1),
2. Subject had a PANSS item score ≥4 on two or more of the following PANSS items: delusions, conceptual disorganization, hallucinations and unusual thought content at baseline,
3. Subject had not demonstrated a decrease (improvement) of ≥20% in the PANSS total score between screening and baseline visits, or PANSS total score had not fallen below 80 at baseline,
4. Subject had a CGI-S score ≥4 at baseline,
5. Subject had a total <5 on the SAS at baseline,
6. Subject did not answer "yes" to suicidal ideation Item 4 (active suicidal ideation with some intent to act, without specific plan) or Item 5 (suicidal ideation with specific plan and intent) on the C-SSRS assessment at baseline (since last visit),
7. Subject met all of the other inclusion criteria and none of the exclusion criteria at baseline.

Compound 1 treatment was size 0, Swedish-orange capsules (50 mg or 75 mg) administered orally once daily. Compound 1 was taken each evening before bedtime, with or without food. Patients received 50 mg/day Compound 1 on days 1 through 3. On day 4, patients were permitted (but not required) to titrate up to a dose of 75 mg/day. Thereafter, if a dose increase was necessary to optimize efficacy, it occurred at regular scheduled visits/weekly intervals starting from visit 4 (week 1) based on investigator judgment. A dose reduction for tolerability purposes was permitted to occur more frequently than at weekly intervals. Patients were flexibly dosed up until visit 6 (week 3), with no dose adjustments allowed thereafter. The duration of treatment was four weeks.

Matching placebo treatment was size 0, Swedish-orange capsules administered orally once daily. Placebo treatment was taken at the same time each evening before bedtime, with or without food. Subjects randomized to placebo received placebo throughout the study.

Both Compound 1 and placebo were provided in blister packs that were identical in packaging, labeling, weight, appearance and schedule of administration.

Treatment with anticholinergic agents or propranolol was permitted for akathisia and movement disorders. Lorazepam, temazepam, and eszopiclone (or their equivalents) were permitted as needed for anxiety or insomnia, but not within 8 hours before any trial assessment. The primary efficacy endpoint was change from baseline to week 4 in the Positive and Negative Symptom Scale (PANSS) total score. Prespecified secondary efficacy endpoints included change from baseline to week 4 in the Clinical Global Impressions-Severity (CGI-S) score, PANSS subscale scores, the Brief Negative Symptom Scale (BNSS) total score and the Montgomery-Asberg Depression Rating Scale (MADRS) total score; a PANSS response (defined as an improvement of ≥20% in the total score on the PANSS); and the change from baseline in the uncorrelated PANSS score matrix (UPSM)-transformed PANSS factor severity scores. The UPSM-transformed PANSS factors measure drug effects on clinical symptom domains of schizophrenia with greater specificity by correcting for correlated improvements among the individual PANSS items. Change from baseline in primary and secondary efficacy measures were analyzed using a mixed model for repeated measurement (M MRM) analysis.

Study design: The study consisted of three periods: (1) screening/washout (up to 14 days), (2) treatment (four weeks in-patient), and (3) a follow-up visit (seven days after last study drug dose for subjects who discontinued prior to visit 7 (week 4) or who complete the study but do not elect to enroll in the open-label extension study (described in Example 1.2)). During the screening/washout period, patients were evaluated for eligibility for a period of up to 14 days, during which they were tapered off all psychotropic medications in a manner consistent with labeling recommendations and conventional medical practices. Subjects remained hospitalized for the duration of the screening/washout period.

During the double-blind phase, patients were in-patient through week 4, at which point they were eligible for hospital discharge. At baseline (Day 1), subject who successfully completed the washout of prior medication and met the randomization criteria were randomly assigned in a 1:1 ratio to one of two treatment arms: Compound 1 (to receive a flexible dose of 50 mg/day or 75 mg/day for four weeks) or placebo (for four weeks). Study drug dosing was initiated the evening of the baseline visit. Treatment continued once-daily at night for the remainder of the study, as described above.

Subjects who completed the double-blind treatment phase were eligible to participate in a separated, open-label, 26-week extension study. Subjects who discontinued early from the study or completed the study, but did not enter the 6-month extension study were required to complete a follow-up visit seven days (±two days) post last dose of study drug or placebo.

Safety: Safety assessments included monitoring for adverse events and serious adverse events, evaluation of vital signs and weight, laboratory tests (including fasting lipid and glucose levels), and 12-lead electrocardiography. Extrapyramidal symptoms were assessed with the use of the Simpson-Angus Rating Scale (SAS; scores range from 0 to 40, with higher scores indicating more extrapyramidal signs in 10 domains, each scored from 0 to 4), the Barnes Rating Scale for drug-Induced Akathisia (BARS; global clinical assessment scores range from 0 to 5, with higher scores indicating greater akathisia), and the Abnormal Involuntary Movement Scale (AIMS; scores range from 0 to 44, with higher scores indicating more frequent and severe abnormal involuntary movements). Suicidality was assessed with the use of the Columbia-Suicide Severity Rating Scale (C-SSRS). Sleep quality was assessed with the use of the Pittsburgh Sleep Quality Index (PSQI; global scores range from 0 to 21, with higher scores indicating worse sleep quality).

Statistical analysis method: Analyses of efficacy were performed in the modified intention-to-treat population, which included all patients who underwent randomization, received at least one dose of Compound 1 or placebo, and had a baseline measurement and at least one post-baseline measurement of efficacy based on the PANSS or CGI-S scale. However, all the patients fulfilled these criteria, and the modified intention-to-treat population was the same as the intention-to-treat population. The safety population included all patients who underwent randomization and received at least one dose of Compound 1 or placebo. No interim analyses or unblinded data monitoring were performed in this trial.

The primary efficacy end point was evaluated with the use of a mixed model for repeated measures; effect sizes were calculated as the absolute value of the difference between the Compound 1 group and the placebo group in the change in score from baseline at week 4, divided by the pooled standard deviation of the between-group difference in the change in score. In order to assess the robustness of the mixed model for repeated-measures analysis of the primary end point and the potential effect of missing data due to early withdrawals, a tipping-point analysis and pattern-mixture modeling with placebo-based multiple imputation were performed as sensitivity analyses.

The secondary efficacy end points were also evaluated with the use of a mixed model for repeated measures, with the exception of the UPSM-transformed PANSS factors, which were evaluated with the use of a prespecified analysis of covariance model to assess domain-specific change in patients who completed the 4-week trial. Because no adjustment for multiple comparisons was performed, no inferences can be drawn regarding the secondary efficacy end points; these results are presented as point estimates with unadjusted 95% confidence intervals only. PANSS response was evaluated with the use of a logistic-regression model with total score on the PANSS at baseline as a covariate.

Descriptive statistics were used to analyze safety data, including adverse events, laboratory values, findings from clinical evaluations, and C-SSRS scores. Changes from baseline in scores on the SAS, BARS, and AIMS were evaluated with the use of a mixed model for repeated measures. Only one postbaseline PSQI assessment was performed, and thus these data were evaluated with the use of analysis of covariance.

Results: In this randomized, placebo-controlled, 4-week study, Compound 1, in flexible doses of 50 or 75 mg/day, demonstrated statistically significant and clinically meaningful symptom improvement in patients with schizophrenia experiencing an acute exacerbation. Compound 1 exhibited robust, broad-spectrum activity across a range of positive, negative, depressive, and general psychopathology symptoms. Improvement in negative symptoms was especially notable, with an effect size of 0.48 on the Brief Negative Symptom Scale. The tolerability and safety profile of Compound 1 appeared to be similar to placebo in this 4-week trial.

Patients: A total of 295 patients were screened, of whom 245 underwent randomization, received at least one dose of Compound 1 or placebo, and had at least one postbaseline efficacy evaluation. The 4-week trial was completed by 78.3% of the patients in the Compound 1 group and by 79.2% of those in the placebo group. Reasons for discontinuation in the Compound 1 group included: 26 patients discontinued treatment, 5 had lack of efficacy, 10 had adverse events, 9 withdrew consent and 2 had other reasons. Reasons for discontinuation in the placebo group included: 26 discontinued treatment, 4 had lack of efficacy, 8 had adverse event and 14 withdrew consent. The percentages of patients in the Compound 1 group who were receiving the 75-mg-per-day dose were 67.2% at week 1, 70.0% at week 2, and 72.5% at week 3; the Compound 1 dose was reduced from 75 mg to 50 mg per day in 4 patients. The mean (±SD) duration of exposure to Compound 1 or placebo was 24.3±7.6 days in the Compound 1 group and 25.4±6.4 days in the placebo group. The use of concomitant medications included anticholinergic agents (1 patient in the placebo group), antipsychotic agents (1 patient in the placebo group), anxiolytics (32 patients in the Compound 1 group, and 30 patients in the placebo group), and hypnotics and sedative agents (10 patients in the Compound 1 group, and 15 patients in the placebo group). Clinical and demographic characteristics among the patients at baseline were similar in the two trial groups; the mean age was 30.3 years, 81.6% were white, 63.7% were male, and the mean time since the onset of schizophrenia was 5 years. The mean total scores on the PANSS at baseline were 101.4 in the Compound 1 group and 99.7 in the placebo group Baseline characteristics: Baseline subject characteristics are shown in Table 1.

TABLE 1

Baseline subject characteristics

| Characteristic | Statistic | Placebo (N = 125) | Compound 1 (N = 120) | Total (N = 245) |
|---|---|---|---|---|
| Age - yr | | 30.6 ± 6.1 | 30.0 ± 5.8 | |
| Male sex - no. (%) | | 77 (64.2) | 79 (63.2) | |
| Race - no. (%) | | | | |
| White | | 104 (83.2) | 96 (80.0) | |
| Black | | 20 (16.0) | 19 (15.8) | |
| Other | | 1 (0.8) | 5 (4.2) | |
| Hispanic ethnic group - no. (%) | | 6 (4.8) | 5 (4.2) | |
| Body Mass Index | | 24.7 ± 3.7 | 25.0 ± 4.3 | |
| Years since initial onset of schizophrenia | | 5.5 ± 4.8 | 5.3 ± 4.8 | |
| No. of prior psychiatric hospitalizations | | 1.2 ± 0.7 | 1.3 ± 0.7 | |
| PANSS Total Score | Mean ± SD | 99.7 (7.76) | 101.4 (8.40) | 100.5 (8.11) |
| | Median | 100.0 | 102.0 | 101.0 |
| | Min, Max | 80, 122 | 82, 122 | 80, 122 |
| PANSS Positive Subscale Score | Mean ± SD | 25.4 (3.05) | 25.8 (3.30) | 25.6 (3.17) |
| | Median | 25.0 | 25.5 | 25.0 |
| | Min, Max | 17, 33 | 18, 33 | 17, 33 |
| PANSS Negative Subscale Score | Mean ± SD | 24.9 (3.97) | 24.7 (3.93) | 24.8 (3.94) |
| | Median | 25.0 | 25.0 | 25.0 |
| | Min, Max | 10, 36 | 15, 33 | 10, 36 |
| PANSS Positive vs. Negative Subscale Score | | | | |
| Positive < Negative | n (%) | 57 (45.6%) | 49 (40.8%) | 106 (43.3%) |
| Positive >= Negative | n (%) | 68 (54.4%) | 71 (59.2%) | 139 (56.7%) |
| CGI-S Score | Mean (SD) | 4.9 (0.48) | 5.0 (0.44) | 5.0 (0.46) |
| 4-5 | n (%) | 114 (91.2%) | 107 (89.2%) | 221 (90.2%) |
| >5 | n (%) | 11 (8.8%) | 13 (10.8%) | 24 (9.8%) |
| BNSS Total Score | | 37.4 ± 12.0 | 37.2 ± 11.5 | |
| MADRS Total Score | | 12.6 ± 7.1 | 13.1 ± 7.2 | |
| Country - no. (%) | | | | |
| United States | | 25 (20.0) | 27 (22.5) | |
| Hungary | | 6 (4.8) | 6 (5.0) | |
| Romania | | 5 (4.0) | 5 (4.2) | |
| Russia | | 52 (41.6) | 46 (38.3) | |
| Ukraine | | 37 (29.6) | 36 (30.0) | |

Efficacy: The least-squares mean change from baseline in the total score on the PANSS at week 4 was −17.2 points in the Compound 1 group and −9.7 points in the placebo group (least-squares mean difference, −7.5 points; 95% confidence interval [CI], −11.9 to −3.0; P=0.001). The between-group least-squares mean differences in the changes from baseline in the CGI-S scale score and the PANSS positive, negative, and general psychopathology subscale scores at week 4 were −0.5 points (95% CI, −0.7 to −0.2), −1.7 points (95% CI, −3.1 to −0.3), −1.5 points (95% CI, −2.6 to −0.4), and −4.3 points (95% CI, −6.6 to −2.0), respectively. The between-group least-squares mean differences in the changes from baseline in the total scores on the BNSS and MADRS at week 4 were −4.3 points (95% CI, −6.8 to −1.8) and −1.8 points (95% CI, −3.2 to −0.3), respectively. A PANSS response at week 4 was observed in 64.6% of the patients in the Compound 1 group and in 44.0% of those in the placebo group (odds ratio, 2.6; 95% CI, 1.4 to 4.9). Because of the lack of a prespecified plan for adjustment for multiple comparisons of secondary end points, the confidence intervals are not adjusted for multiple comparisons and no inferences can be drawn from any secondary end-point data. The results of planned sensitivity analyses were in the same direction as the results of the primary efficacy analysis. A trial-group-by-country analysis showed no significant interaction effect at week 4.

Safety: Adverse events in the patients were monitored. Adverse events are untoward medical occurrences that started at the same time of or after the first dose of study medication. The incidence of adverse events in the treatment group was very low. Across all types of adverse events the incidence for the treatment group was similar to placebo. For certain adverse events, the incidence in the treatment group was less than placebo. The incidence of adverse events compares favorably to commercially available antipsychotic agents, including the atypical antipsychotics that have affinity to D2 dopamine receptors.

Adverse events are summarized in Tables 2-6. Severe adverse events occurred in seven patients (5.8%) in the Compound 1 group and in two patients (1.6%) in the placebo group. The incidence of insomnia was 3.3% in the Compound 1 group and 10.4% in the placebo group, and concomitant hypnotics were used by 8.3% and 12.0% of the patients, respectively. Treatment with Compound 1, as compared with placebo, was associated with an improvement in sleep quality, with a least squares mean (±SE) change from baseline in the PSQI global score at week 4 of −2.5±0.4 points in the Compound 1 group and −1.7±0.4 points in the placebo group.

The incidence of extrapyramidal symptoms (akathisia, restlessness, musculoskeletal or joint stiffness, tremor, and nuchal rigidity) was 3.3% in the Compound 1 group and 3.2% in the placebo group. At week 4, the least-squares mean changes from baseline in the scores on the SAS, the BARS, and the AIMS, which were used to determine the effects on movement disorders, were −0.01±0.01 points, 0.0±0.06 points, and 0.0±0.01 points, respectively, in the Compound 1 group and 0.01±0.01 points, 0.1±0.05 points, and 0.0±0.01 points, respectively, in the placebo group. A concomitant medication to treat extrapyramidal symptoms was prescribed to one patient in the Compound 1 group (lorazepam for restlessness) and one patient in the placebo group (trihexyphenidyl for hand tremor and restlessness).

The two serious adverse events that occurred in the Compound 1 group were worsening of schizophrenia and acute cardiovascular insufficiency in a 37-year-old woman that resulted in sudden death 7 days after she had taken the first 50-mg dose of Compound 1. The patient had a history of essential hypertension and was found on autopsy to have coronary artery disease and pulmonary embolism. There were four serious events in the placebo group (three patients had worsening of schizophrenia and one patient attempted suicide). According to the scores on the C-SSRS, no suicidal ideation or behavior was present among the patients in the Compound 1 group, and there were two instances of suicidality among those in the placebo group.

Differences in vital signs (including orthostatic hypotension or tachycardia), weight, body-mass index, and laboratory values (including prolactin and fasting metabolic measures) between the Compound 1 group and the placebo group were also tracked. There were no clinically significant electrocardiographic abnormalities after baseline, and no patient in the Compound 1 group or the placebo group had a prolongation of the corrected QT interval, calculated with the use of Fridericia's formula (QTcF), of more than 450 msec or an increase in the QTcF interval of more than 60 msec. In the placebo group, the observed change from baseline in body weight at week 4 was 0.1±2.3 kg, and the observed change from baseline in body-mass index at week 4 was 0.0±0.8. In the Compound 1 group, the observed change from baseline in body weight at week 4 was 0.3±1.9 kg, and the observed change from baseline in body-mass index at week 4 was 0.1±0.6. In the placebo group, the median change from baseline in prolactin level at week 4 (male/female) was −0.036/−0.101 nmol/liter. In the Compound 1 group, the median change from baseline in prolactin level at week 4 (male/female) was −0.037/−0.175 nmol/liter.

FIG. 1 shows the change from baseline in PANSS total score of patients during the 4-week study. The treatment group had a least squares mean change from baseline at week 4 of −17.2 compared to −9.7 for placebo, which corresponds to an effect size of 0.45.

Figure 2:
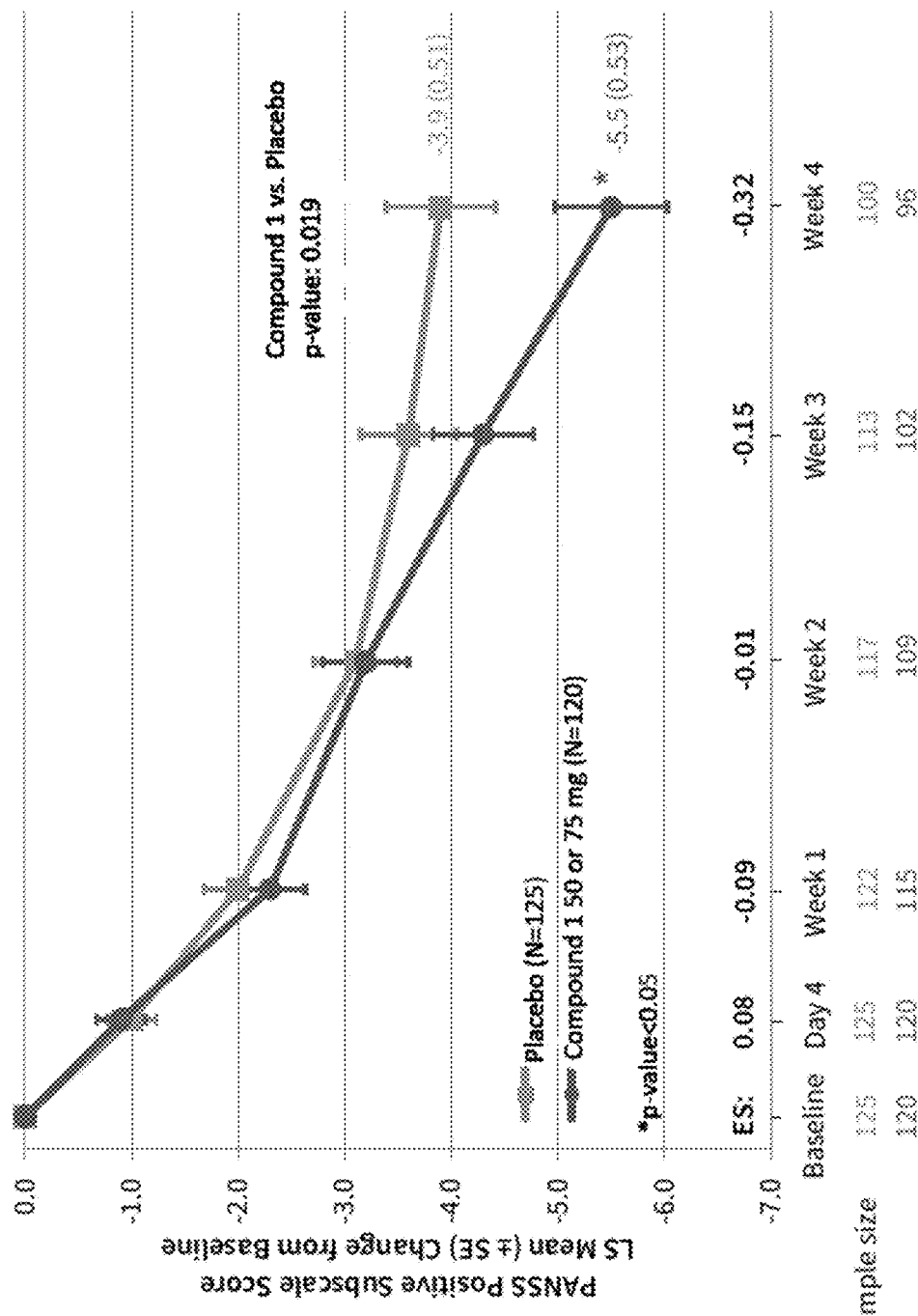
FIG. 2 shows the MMRM analysis of change from baseline in PANSS positive subscale score for the study of Example 1.1.

FIG. 2 shows the change from baseline in PANSS positive subscale score of patients during the 4-week study. The treatment group had a least squares mean change from baseline at week 4 of −5.5 compared to −3.9 for placebo, which corresponds to an effect size of 0.32.

Figure 3:
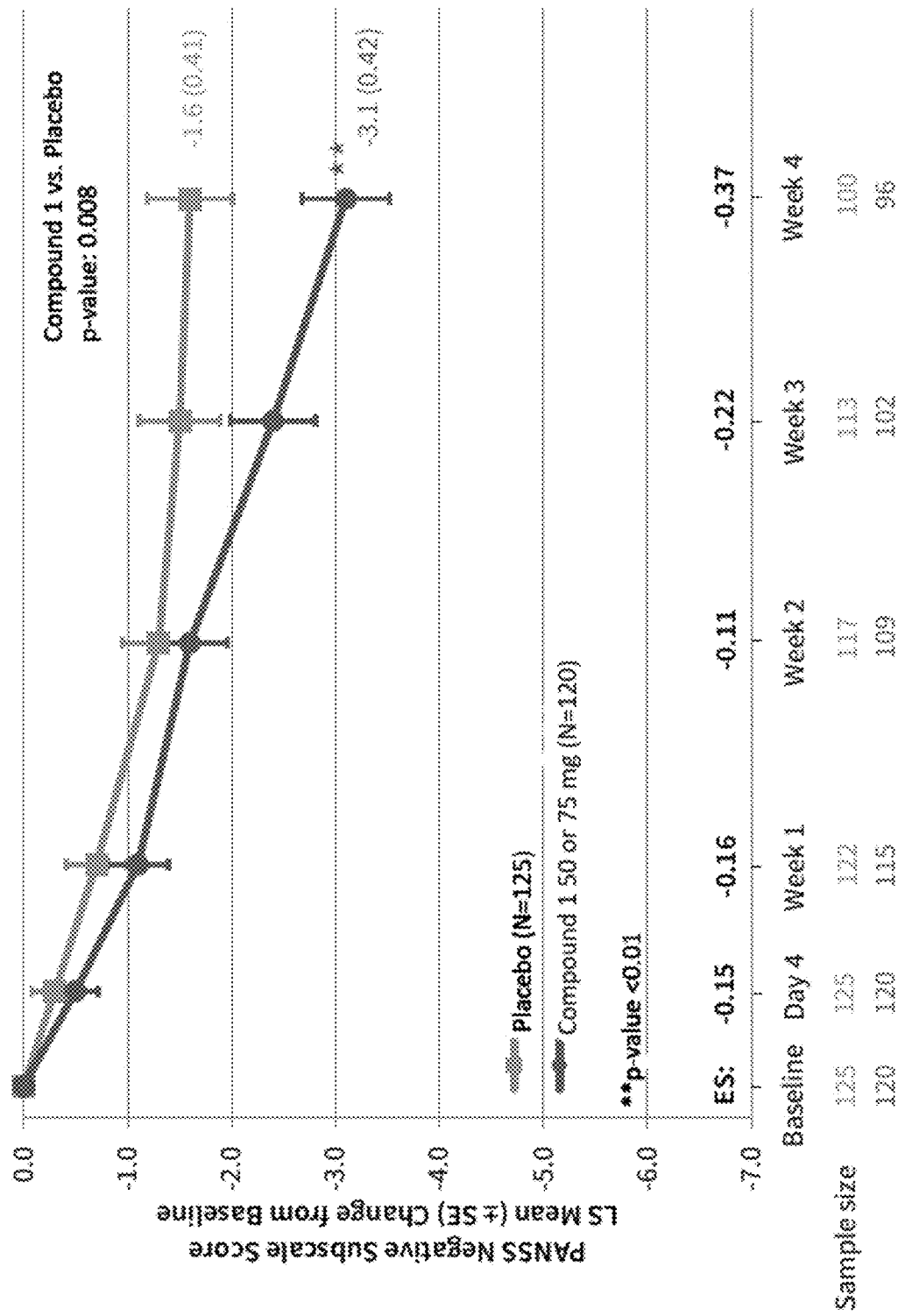
FIG. 3 shows the MMRM analysis of change from baseline in PANSS negative subscale score for the study of Example 1.1.

FIG. 3 shows the change from baseline in PANSS negative subscale score of patients during the 4-week study. The treatment group had a least squares mean change from baseline at week 4 of −3.1 compared to −1.6 for placebo, which corresponds to an effect size of 0.37.

Figure 4:
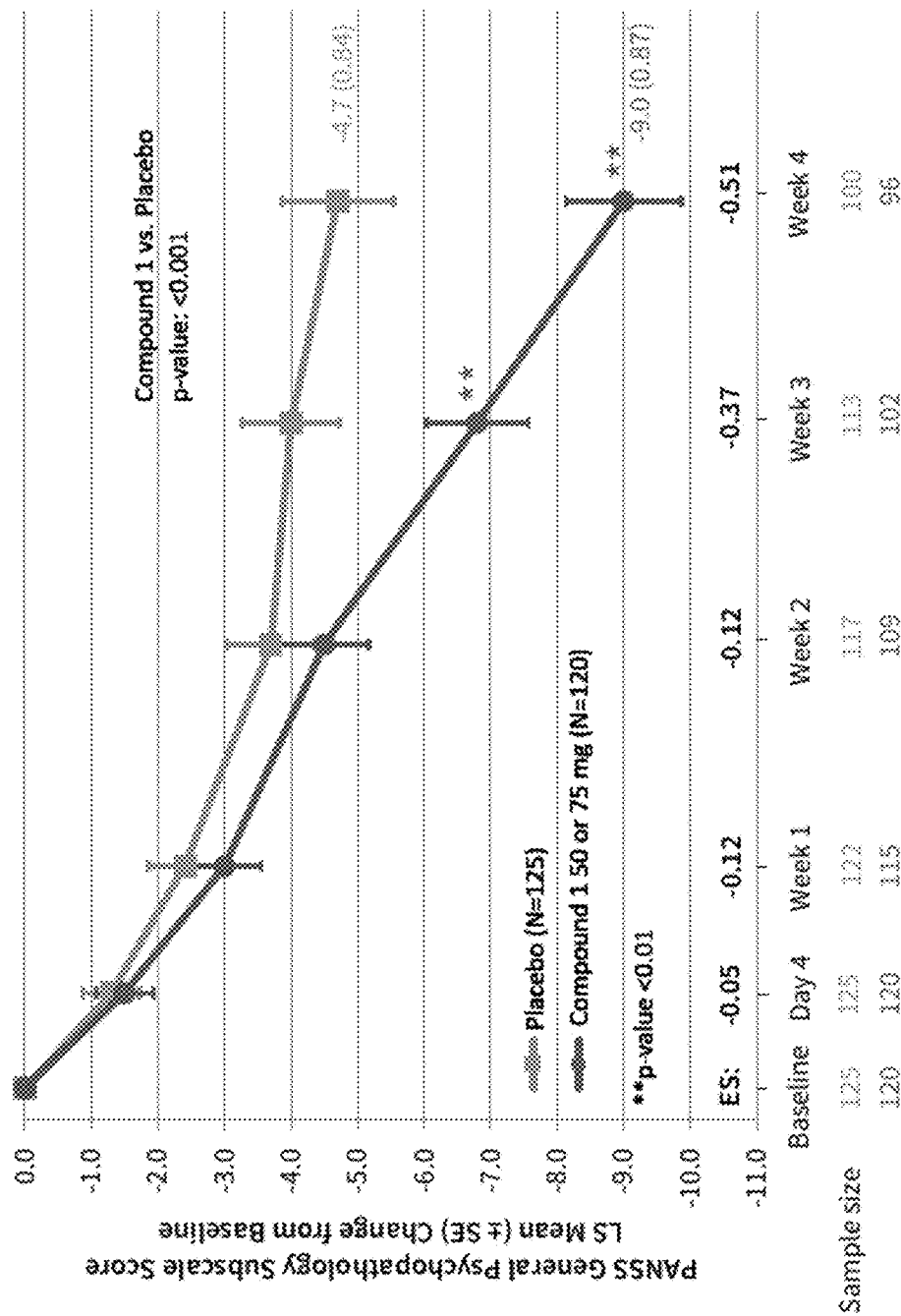
FIG. 4 shows the MMRM analysis of change from baseline in PANSS general psychopathology subscale score for the study of Example 1.1.

FIG. 4 shows the change from baseline in PANSS general psychopathology subscale score of patients during the 4-week study. The treatment group had a least squares mean change from baseline at week 4 of −9.0 compared to −4.7 for placebo, which corresponds to an effect size of 0.51.

Figure 5:
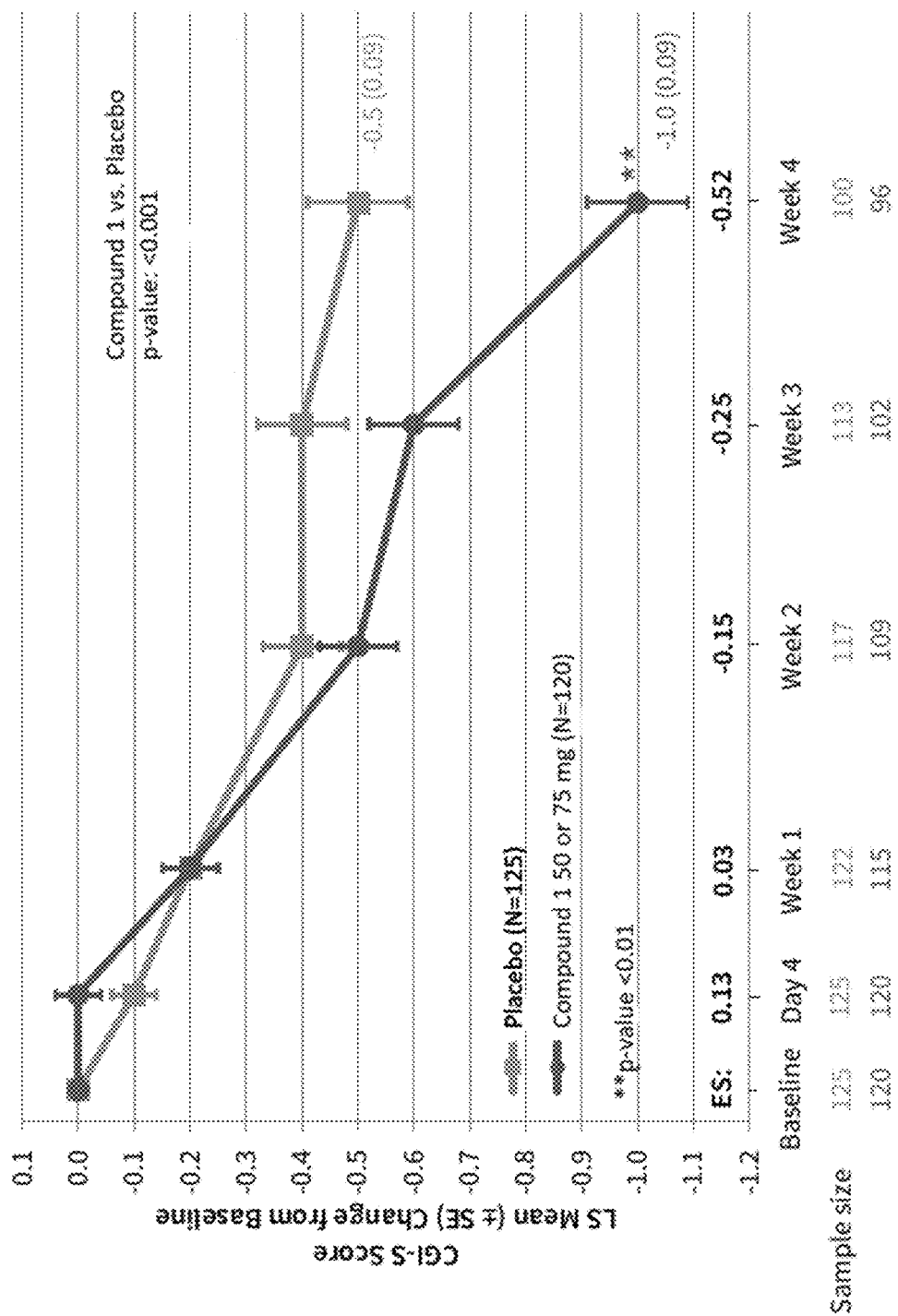
FIG. 5 shows the MMRM analysis of change from baseline in CGI-S score for the study of Example 1.1.

FIG. 5 shows the change from baseline in CGI-S score of patients during the 4-week study. The treatment group had a least squares mean change from baseline at week 4 of −1.0 compared to −0.5 for placebo, which corresponds to an effect size of 0.52.

Figure 6:
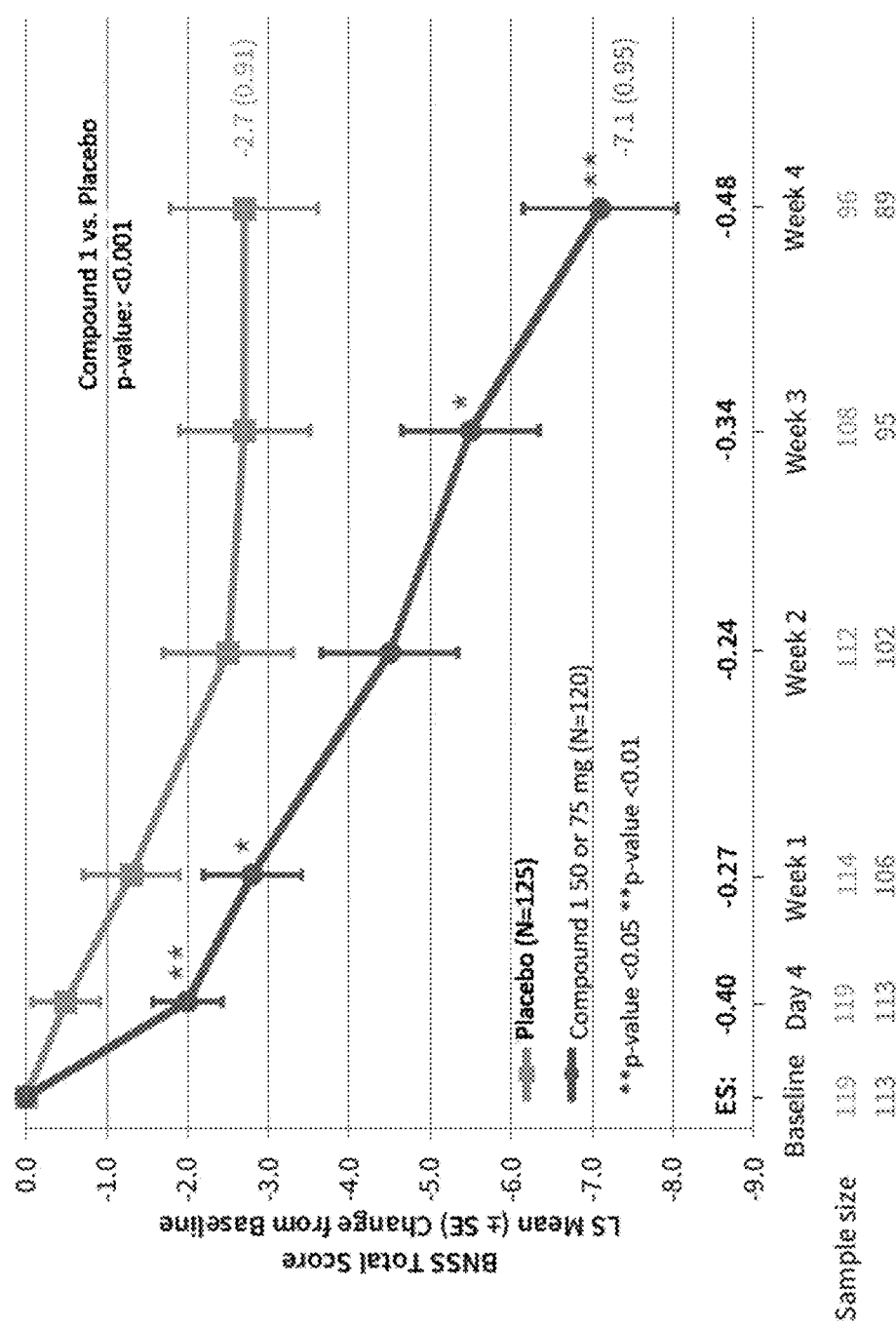
FIG. 6 shows the MMRM analysis of change from baseline in BNSS total score for the study of Example 1.1.

FIG. 6 shows the change from baseline in BNSS total score of patients during the 4-week study. The treatment group had a least squares mean change from baseline at week 4 of −7.1 compared to −2.7 for placebo, which corresponds to an effect size of 0.48.

Figure 7:
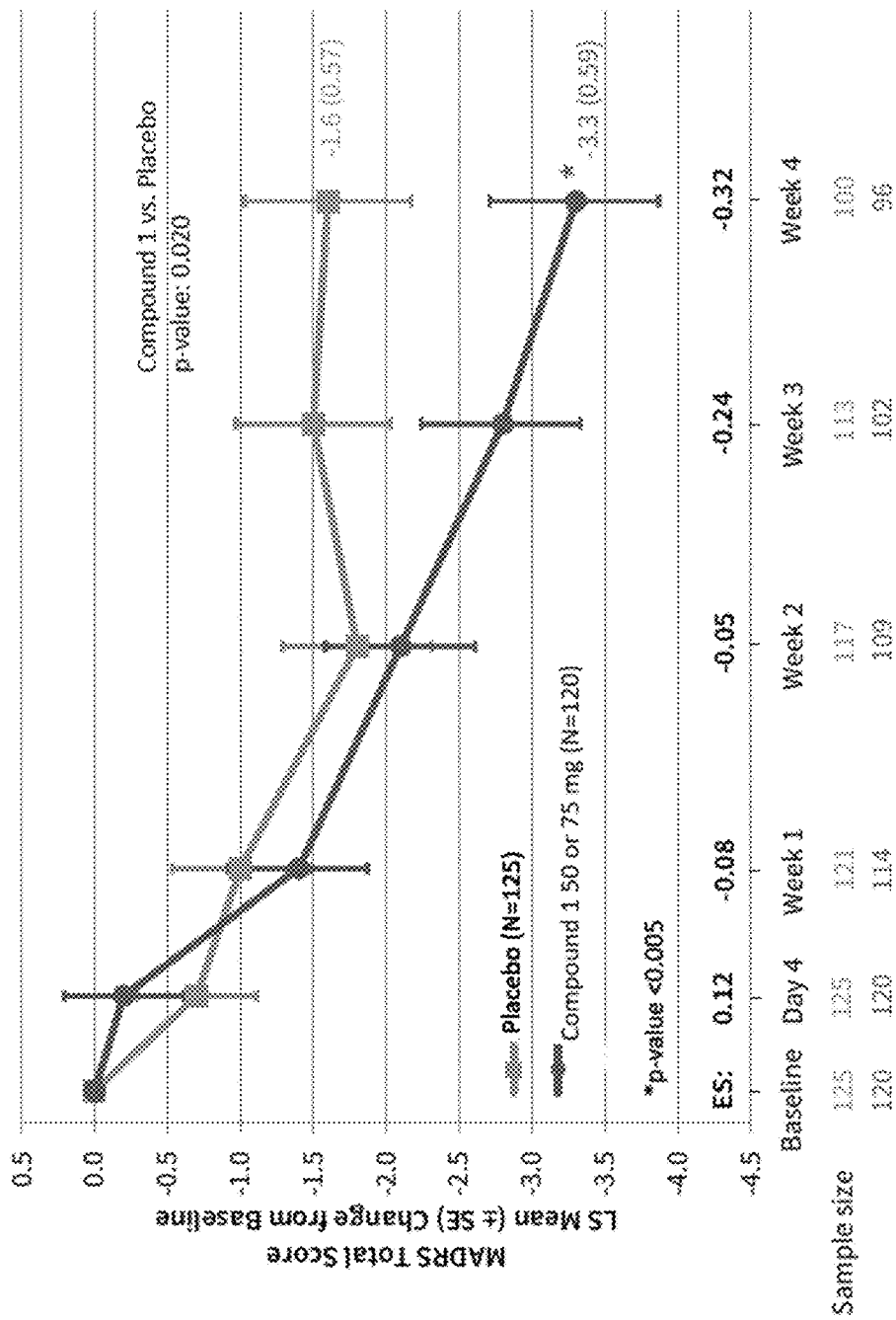
FIG. 7 shows the MMRM analysis of change from baseline in MADRS total score for the study of Example 1.1.

FIG. 7 shows the change from baseline in MADRS total score of patients during the 4-week study. The treatment group had a least squares mean change from baseline at week 4 of −3.3 compared to −1.6 for placebo, which corresponds to an effect size of 0.32.

Table 2 summarizes the incidence of general adverse events occurring in ≥2% of patients in either the treatment group or placebo. The incidence of each of headache, insomnia, acute exacerbation of schizophrenia and anxiety was lower in the treatment group than in the placebo group.

TABLE 2

General adverse events

| Preferred Term | Placebo (N = 125) n (%) | Compound 1 (N = 120) n (%) |
|---|---|---|
| Subjects with AE* | 63 (50.4%) | 55 (45.8%) |
| Headache | 15 (12.0%) | 11 (9.2%) |
| Schizophrenia | 10 (8.0%) | 8 (6.7%) |
| Somnolence | 6 (4.8%) | 8 (6.7%) |
| Agitation | 6 (4.8%) | 6 (5.0%) |
| Nausea | 4 (3.2%) | 6 (5.0%) |
| Insomnia | 13 (10.4%) | 4 (3.3%) |
| Diarrhea | 1 (0.8%) | 3 (2.5%) |
| Dyspepsia | 0 | 3 (2.5%) |
| Anxiety | 9 (7.2%) | 2 (1.7%) |

*Subjects with multiple AEs are counted only once.

Table 3 summarizes the incidence of extrapyramidal adverse events. Incidence of extrapyramidal adverse events in the treatment group was about the same as placebo.

TABLE 3

Extrapyramidal adverse events

| Preferred Term | Placebo (N = 125) n (%) | Compound 1 (N = 120) n (%) |
|---|---|---|
| Any subject experiencing an extrapyramidal symptom AE* | 4 (3.2%) | 4 (3.3%) |
| Akathisia | 1 (0.8%) | 2 (1.7%) |
| Restlessness | 1 (0.8%) | 0 |
| Joint Stiffness | 1 (0.8%) | 0 |
| Musculoskeletal stiffness | 2 (1.6%) | 1 (0.8%) |
| Nuchal rigidity | 1 (0.8%) | 0 |
| Postural tremor | 0 | 1 (0.8%) |
| Tremor | 2 (1.6%) | 0 |

*Subjects with multiple AEs are counted only once.

Table 4 summarizes the incidence of cardiovascular adverse events. Incidence of cardiovascular adverse events in the treatment group were similar to placebo. Total of cardiovascular adverse events incidence in the treatment group was 4.20% compared to 4.00% for placebo.

TABLE 4

Cardiovascular adverse events

| SOC/Preferred Term | Placebo (N = 125) n (%) | Compound 1 (N = 120) n (%) |
|---|---|---|
| Cardiac Disorders | 2 (1.6%) | 3 (2.5%) |
| Atrial tachycardia | 0 | 1 (0.8%) |
| Bradycardia | 0 | 1 (0.8%) |
| Cardiovascular insufficiency* | 0 | 1 (0.8%) |
| Palpitations | 1 (0.8%) | 0 |
| Postural tachycardia syndrome | 1 (0.8%) | 0 |
| Vascular Disorders | 1 (0.8%) | 2 (1.7%) |
| Blood pressure increased | 0 | 1 (0.8%) |
| Hypertension | 0 | 1 (0.8%) |
| Hypotension | 0 | 1 (0.8%) |
| Hot flush | 1 (0.8%) | 0 |
| Dizziness | 2 (1.6%) | 0 |

*Cardiovascular insufficiency resulted in death.

Table 5 summarizes the incidence of serious adverse events. The incidence of serious adverse events in the treatment group was less than placebo.

TABLE 5

Serious adverse events

| | Placebo (N = 125) | | Compound 1 (N = 120) | |
|---|---|---|---|---|
| Preferred Term | n (%) | # Events | n (%) | # Events |
| Subjects with any SAE* | 3 (2.4%) | 4 | 2 (1.7%) | 2 |
| Worsening of Schizophrenia | 3 (2.4%) | 3 | 1 (0.8%) | 1 |
| Cardiovascular insufficiency** | 0 | 0 | 1 (0.8%) | 1 |
| Suicide attempt | 1 (0.8%) | 1 | 0 | 0 |

*Subjects with multiple AEs are counted only once.
**Cardiovascular insufficiency resulted in death.

Table 6 summarizes the incidence of adverse events leading to discontinuation from study. The incidence of such adverse events was similar between treatment group and placebo.

TABLE 6

Adverse events leading to discontinuation

| | Placebo (N = 125) | | Compound 1 (N = 120) | |
|---|---|---|---|---|
| Preferred Term | n (%) | # Events | n (%) | # Events |
| Any AE leading to discontinuation from study* | 8 (6.4%) | 8 | 11 (9.2%) | 11 |
| Schizophrenia | 6 (4.8%) | 6 | 8 (6.7%) | 8 |
| Psychotic disorder | 0 | 0 | 1 (0.8%) | 1 |
| Insomnia | 0 | 0 | 1 (0.8%) | 1 |
| Cardiovascular insufficiency** | 0 | 0 | 1 (0.8%) | 1 |
| Suicide attempt | 1 (0.8%) | 1 | 0 | 0 |
| Palpitations | 1 (0.8%) | 1 | 0 | 0 |

*Subjects with multiple AEs are counted only once. **Cardiovascular insufficiency resulted in death.

Figure 8:
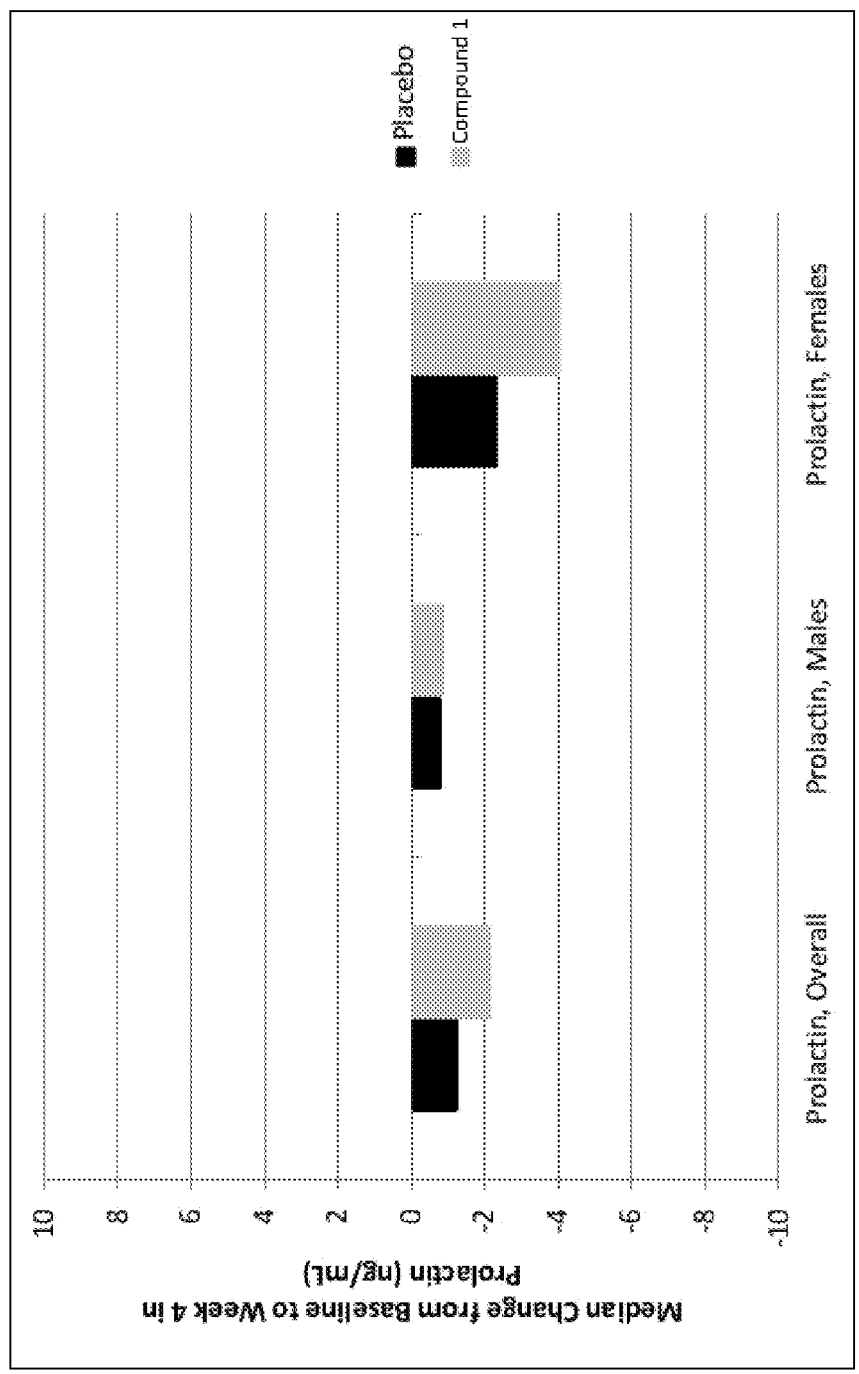
FIG. 8 shows the median change from baseline to week 4 in prolactin levels for the study of Example 1.1.

FIG. 8 shows the median change from baseline in prolactin levels at week 4. The treatment group on average experienced a decrease in prolactin. Table 7 summarizes the prolactin shifts from baseline at week 4. There was no clinically significant impact of Compound 1 on prolactin.

TABLE 7

Prolactin level change from baseline

| Prolactin | Placebo (N = 125) | Compound 1 (N = 120) |
|---|---|---|
| Overall, n | 113 | 114 |
| Low to normal | 2 (1.8%) | 5 (4.4%) |
| Low to high | 0 | 0 |
| Normal to high | 9 (8.0%) | 19 (16.7%)* |
| Males, n (normal range: 2.64-13.13 ng/mL) | 71 | 74 |
| Low to normal | 2 (2.8%) | 5 (6.8%) |
| Low to high | 0 | 0 |
| Normal to high | 9 (12.7%) | 16 (21.6%) |
| Females, n (normal range: 2.74-26.72 ng/mL) | 42 | 40 |

TABLE 7-continued

Prolactin level change from baseline

| Prolactin | Placebo (N = 125) | Compound 1 (N = 120) |
|---|---|---|
| Low to normal | 0 | 0 |
| Low to high | 0 | 0 |
| Normal to high | 0 | 3 (7.5%) |

*Six of the subjects in the Compound 1 group who went from normal to high prolactin levels received another antipsychotic prior to final visit.

Table 8 summarizes the incidence of orthostatic hypotension and orthostatic tachycardia. Orthostatic hypotension is defined as a decrease of ≥20 mmHg in systolic blood pressure or ≥10 mmHg in diastolic blood pressure after the subject had been standing for at least 2 to 4 minutes, compared to the systolic blood pressure and diastolic pressure measured in the supine position, respectively. Orthostatic tachycardia is defined as a heart rate increase of ≥20 beats per minute (bpm) and a heart rate of >100 bpm after the subject was standing for at least 2 to 4 minutes, compared to the heart rate measured in the supine position. The incidence of orthostatic hypotension and orthostatic tachycardia in the treatment group was similar to placebo, with the incidence of orthostatic hypotension in the treatment group being less than placebo.

TABLE 8

Orthostatic hypotension and orthostatic tachycardia

| | Placebo (N = 125) | Compound 1 (N = 120) |
|---|---|---|
| Orthostatic hypotension | 9 (7.2%) | 5 (4.2%) |
| ≥20 mmHg decrease in SBP from supine to standing | 7 (5.6%) | 2 (1.7%) |
| ≥10 mmHg decrease in DBP from supine to standing | 6 (4.8%) | 3 (2.5%) |
| Orthostatic tachycardia (≥20 bpm increase from supine to standing in heart rate and >100 bpm after standing) | 3 (2.4%) | 5 (4.2%) |

Table 9 summarizes the incidence of QT prolongation as measured by the QTcF interval. Patient data was collected via electrocardiogram (ECG). The number and percentage of subjects with QTc values in the following categories were identified. The same criteria apply to both QTcF and QTcB.

>450 msec at any post-baseline time point (including unscheduled visits) not present at baseline >480 msec at any post-baseline time point (including unscheduled visits) not present at baseline >500 msec at any post-baseline time point (including unscheduled visits) not present at baseline ≥30 msec increase from baseline for at least one post-baseline measurement (including unscheduled visits) and <60 msec increase from baseline for all post-baseline measurements (including unscheduled visits)

≥60 msec increase from baseline for at least one post-baseline measurement (including unscheduled visits)

For both the treatment group and placebo group, there were no incidences of QT prolongation.

TABLE 9

QTcF interval

| | Placebo (N = 125) | Compound 1 (N = 120) |
|---|---|---|
| QTcF Interval, n | 113 | 113 |
| >450 msec at any post-baseline time point not present at baseline | 0 | 0 |
| >480 msec at any post-baseline time point not present at baseline | 0 | 0 |
| >500 msec at any post-baseline time point not present at baseline | 0 | 0 |
| ≥30 msec increase from baseline for at least one post-baseline measurement and <60 msec increase from baseline for all post-baseline measurements | 0 | 0 |
| ≥60 msec increase from baseline for at least one post-baseline measurement | 0 | 0 |

Table 10 summarizes the extrapyramidal symptoms as measured by the Barnes Akathisia Rating Scale (BARS), the Abnormal Involuntary Movement Scale (AIMS), and the Simpson-Angus Scale (SAS).

TABLE 10

AIMS, BARS, and SAS scores.

| | Placebo (N = 125) | Compound 1 (N = 120) |
|---|---|---|
| AIMS Total Score Classification - Shift from Baseline (Overall Post-Baseline), n | 125 | 120 |
| Normal to Abnormal | 0 | 2 (1.7%) |
| AIMS Global Severity Score - Categorical Summary of Change from Baseline (LOCF Endpoint), n | 125 | 120 |
| Worsened | 1 (0.8%) | 2 (1.7%) |
| Unchanged | 124 (99.2%) | 117 (97.5%) |
| Improved | 0 | 0 |
| BARS Global Clinical Assessment - Categorical Summary of Change from Baseline (LOCF Endpoint), n | 125 | 120 |
| Worsened | 5 (4.0%) | 1 (0.8%) |
| Unchanged | 116 (92.8%) | 107 (89.2%) |
| Improved | 4 (3.2%) | 12 (10.0%) |
| SAS Mean Score Classification Shift (Overall Post-Baseline) | 125 | 120 |
| Normal to Abnormal | 3 (2.4%) | 2 (1.7%) |

Accordingly, various methods of the present disclosure result in low incidence of adverse events, for example, adverse events less than, the same as, or about the same as or similar to placebo. This is in contrast to many typical and atypical antipsychotics, which have affinity to dopamine D2 receptors, and which produce higher incidence of adverse events.

Discussion: In this 4-week, flexible-dose trial involving patients with an acute exacerbation of schizophrenia, Compound 1, a drug that does not bind to the dopamine D2 receptor, resulted in a greater reduction from baseline in the PANSS total score at week 4 (the primary efficacy end point) than placebo. Treatment with Compound 1 was associated with changes in the severity scores on the secondary efficacy measures (including the CGI-S scale and the PANSS positive, negative, and general psychopathology subscales) at week 4 that were in the same direction as the scores in the primary efficacy analysis. Treatment with Compound 1 was also associated with changes in severity scores of negative symptoms of schizophrenia at week 4 (as measured by both the BNSS total score and the UPSM-transformed PANSS negative symptom factor scores) that were in the same direction as the scores in the primary efficacy analysis. Changes in the UPSM-transformed PANSS negative symptom factor scores (apathy or avolition and deficit of expression) were shown previously to have minimal correlations with change in the UPSM-transformed PANSS positive symptom factor score, a finding that suggests that specific effects on negative symptoms are measured by the UPSM negative symptom factors. A reduction in the total score on the PANSS was observed during the additional 26-week extension study of open-label treatment with Compound 1 (see Example 1.2).

The percentage of patients who discontinued Compound 1 or placebo was similar in the two groups (21.7% versus 20.8%, respectively), and was similar to or lower than the percentage of patients who had dropped out of previous short-term trials of first- and second-generation antipsychotics; however, the design of the previous trials does not allow direct comparison with our trial. The incidence of adverse events was generally similar in the Compound 1 group and the placebo group, with a difference of 2.5% or less for each event. The Compound 1 and placebo groups were similar with respect to the percentage of patients who reported extrapyramidal symptoms (3.3% vs. 3.2%), the percentage who used medications to treat extrapyramidal symptoms, and the findings on movement disorder scales. In addition, minimal effects on prolactin were observed in the Compound 1 group. These findings are consistent with the absence of D2-receptor binding for Compound 1. Short-term treatment with Compound 1 was associated with a mean increase in body weight of 0.3 kg, reductions in total and LDL cholesterol levels, and no change in other metabolic laboratory values. No clinically significant electrocardiographic abnormalities, including prolongation in the QTcF interval, were present after baseline.

In conclusion, in this 4-week trial involving patients with an acute exacerbation of schizophrenia, Compound 1, a drug with a non-D2-receptor-binding mechanism of action but with agonist activity at TAAR1 and 5-HT$_{1A}$ receptors, led to a greater reduction in the total score on the PANSS than placebo.

Example 1.2: 26-Week Extension Study

A 26-week open-label safety and tolerability extension study was performed for subjects with schizophrenia who completed the treatment phase from Example 1.1. Patients who met the entry criteria transitioned immediately from the Example 1.1 study to the extension study (Example 1.1, visit 7 (day 29) assessments served as the baseline assessments for this study). Subjects were hospitalized for the first week of the study, if deemed appropriate by the investigator. During the treatment period, patients were seen weekly for the first four weeks, then every four weeks thereafter up to week 26. Telephone calls were made by a member of the clinical research staff to the patients between schedules study visits (between weeks 1 and 2, and at weeks 5, 7, 9, 11, 13, 15, 17, 19, 21, 23 and 25) to monitor clinical symptoms and adverse events. Subjects who discontinued early from the study or completed the study were required to complete a follow-up visit seven days (±two days) post last dose of study drug.

A total of 156 patients (80.8% of those who completed the 4-week trial) were enrolled and received treatment with Compound 1 in the 26-week, open-label extension study. Among 77 patients who had initially been randomly assigned to receive Compound 1 in the double-blind, Example 1.1 trial and then continued to receive treatment in the open-label extension, the mean (±SD) change from the extension-study baseline in the PANSS total score at week 26 was −17.1±12.4 points. Among 79 patients who had initially been randomly assigned to receive placebo and then switched to open-label Compound 1, the mean change from the extension-study baseline in the PANSS total score at week 26 was −27.9±16.4 points. The adverse events related to extrapyramidal symptoms that occurred among the 156 patients included parkinsonism (2 patients), dyskinesia (1 patient), tremor (1 patient), and restlessness (1 patient).

Patients were dosed orally once daily with Compound 1 (referred to in the Tables as "Compound 1") at 50 mg/day for Days 1-3 of the extension study. Beginning on day 4, flexible dosing ranging from 25 to 75 mg/day was permitted, if deemed clinically necessary (for reasons of safety, tolerability or efficacy) by the investigator. On day 4, subjects were permitted (but not required) to titrate up to 75 mg/day for reasons of efficacy. Thereafter, if a dose increase was necessary to optimize efficacy, it occurred at regular, scheduled study visits based on investigator judgment. Day 4 dosing changes occurred at an unscheduled visit. Thereafter, an increase in dose occurred at weekly intervals in increments of one dose level at a time to a maximum dose of 75 mg/day. Dose reduction for tolerability purposes was allowed at any time during the study. Doses of 25, 50 and 75 mg/day were allowed during weeks 2-26 of the study.

Compound 1 treatment was size 0, Swedish-orange capsules (25, 50 or 75 mg/day) administered orally once daily. Study drug was taken with or without food at approximately the same time each evening before bedtime.

Safety and tolerability were monitored throughout the study by collection of physical examination results, ECGs, vital signs, AEs, clinical laboratory parameters, C-SSRS, body weight and BMI. Effectiveness was evaluated using the PANSS total and subscale scores, as well as CGI-S, BNSS, and MADRS scores. Subjects provided information on subjective drug effects via a questionnaire.

To qualify for participation, patients met all of the following inclusion criteria:
1. Subject had completed Example 1.1 study through Week 4.
2. Subject had not taken any medication other than the study drug for the purpose of controlling schizophrenia symptoms during Example 1.1 study.

Patients did not meet any of the following exclusion criteria:
1. Subject answered "yes" to "suicidal ideation" Item 4 (active suicidal ideation with some intent to act, without specific plan) or Item 5 (active suicidal ideation with specific plan and intent) on the C-SSRS assessment at visit 7 of the Example 1.1 study.
2. Subject had a clinically significant abnormality including physical examination, vital signs, ECG, or laboratory test at visit 7 of the Example 1.1 study that the investigator in consultation with the medical monitor considered to be inappropriate to allow participation in the study.
3. Subject had a positive urine drug screen (UDS) or breath alcohol test at visit 7 of the Example 1.1 study.
4. Subject was pregnant or lactating.
5. Subject was at high risk of non-compliance in the investigator's opinion.
6. Subject was, in the opinion of the investigator, unsuitable in any other way to participate in this study.

The primary endpoints of the study were the incidence of overall AEs, SAEs, and AEs leading to discontinuation. Secondary endpoints included:

Absolute values and changes from double-blind (DB) Baseline of Example 1.1 in clinical laboratory tests (hematology, serum chemistry, urinalysis, glucose and lipid panel, prolactin, glycosylated hemoglobin (HbA1c));

Absolute values and changes from DB Baseline of Example 1.1 in clinical evaluations (vital signs body weight, BMI, blood pressure [supine and standing], heart rate [supine and standing], 12 lead ECGs);

Frequency and severity of suicidal ideation and suicidal behavior using the C-SSRS;

Rate of relapse and time to relapse during the 26-week open label period for subjects who demonstrated a clinical response to four weeks of treatment in Example 1.1. Relapse was defined as the onset of any of the following:

An increase in PANSS total score ≥30% from the PANSS total score at clinical response and a CGI-S score ≥3;

Re-hospitalization for worsening of psychosis;

Emergence of suicidal ideation, homicidal ideation and/or risk of harm to self or others;

Changes from DB Baseline of Example 1.1 (see Table 1) in PANSS total score, PANSS subscale scores (positive, negative, and general psychopathology), CGI-S score, BNSS total score, and MADRS total score; and Proportion of patients who achieved a response, defined as a 20% or greater improvement in PANSS total score from the baseline, and calculated using (1) the DB Baseline of Example 1.1 study for subjects assigned to double-blind Compound 1, and (2) the OL Baseline of this study for subjects assigned to double-blind placebo in the Example 1.1 study.

Results:

105 subjects (66.9%) completed the 26-week study; 52 subjects (33.1%) discontinued due to adverse event (18; 11.5%), withdrawal by subject (16; 10.2%), other (9; 5.7%), lack of efficacy (8; 5.1%) or noncompliance (1; 0.6%).

Efficacy measures were recorded over the course of the 26-week extension study.

Figure 9:
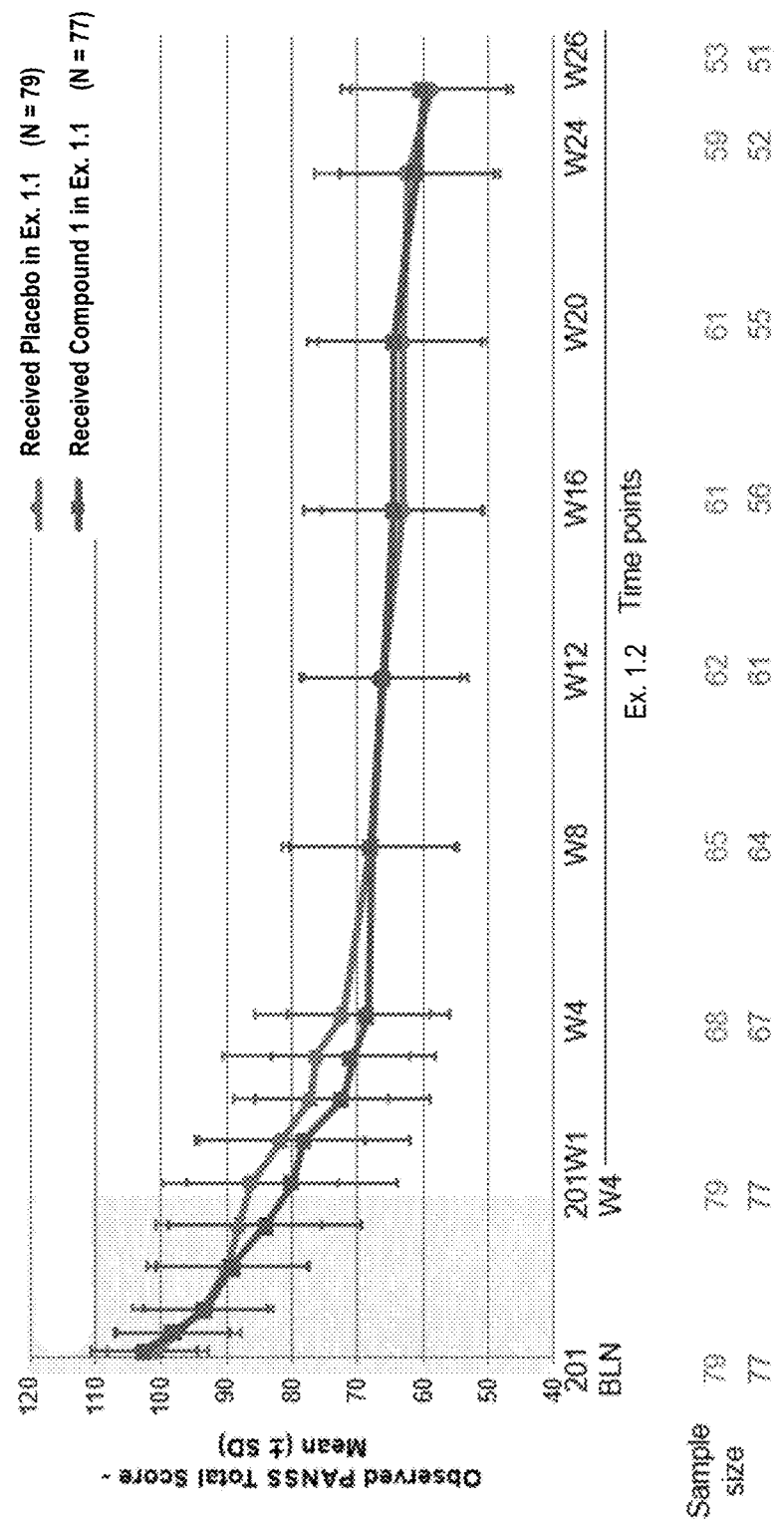
FIG. 9 shows the observed PANSS total score during double-blind treatment (Example 1.1) and open-label extension study (Example 1.2).

FIG. 9 shows the PANSS total score during the extension study with the PANSS total score data from the Example 1.1 study shown for reference.

Figure 10:
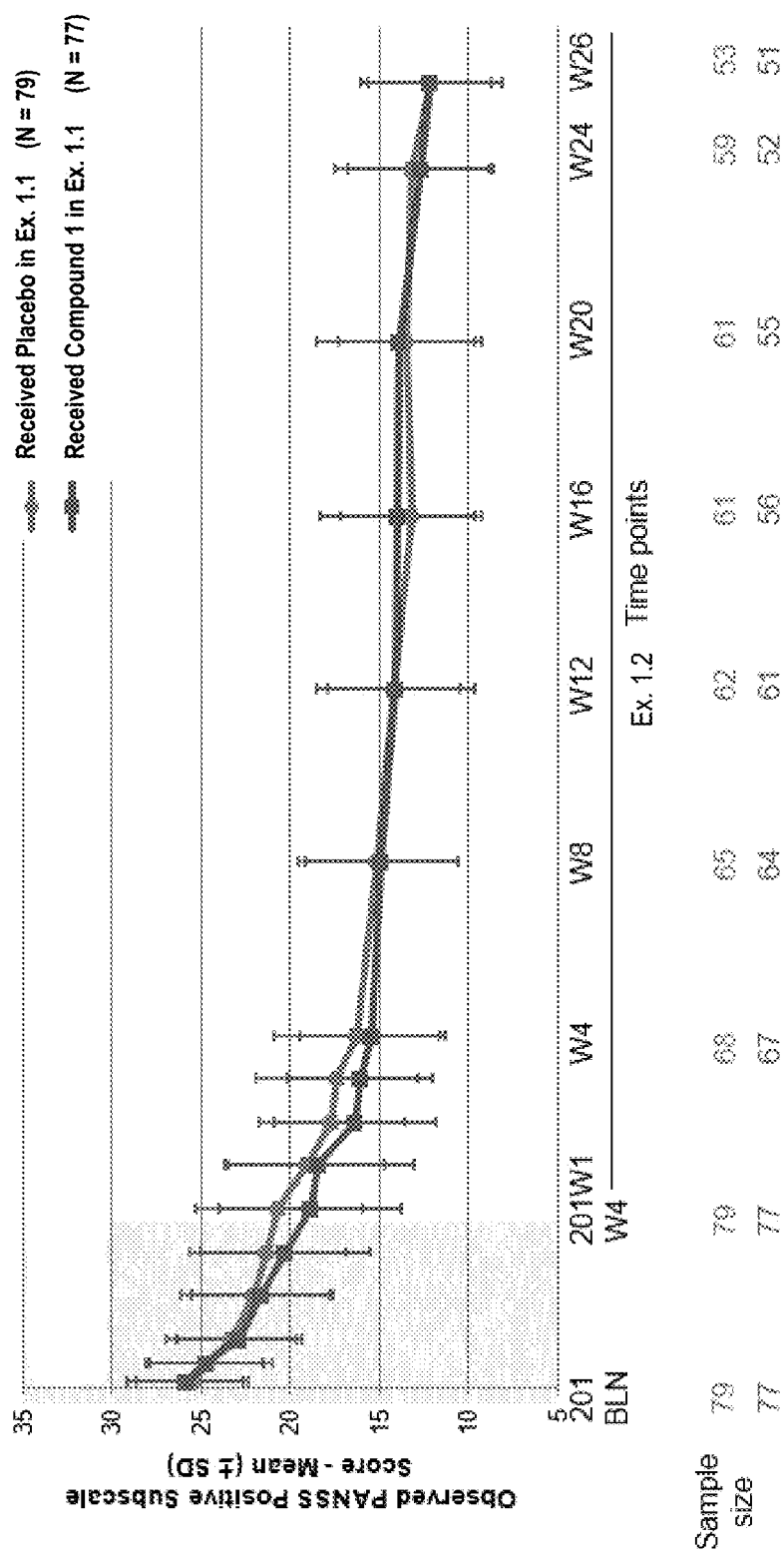
FIG. 10 shows the observed PANSS positive subscore during double-blind treatment (Example 1.1) and open-label extension study (Example 1.2).

FIG. 10 shows the PANSS positive subscale score during the extension study with the PANSS positive subscale score data from the Example 1.1 study shown for reference.

Figure 11:
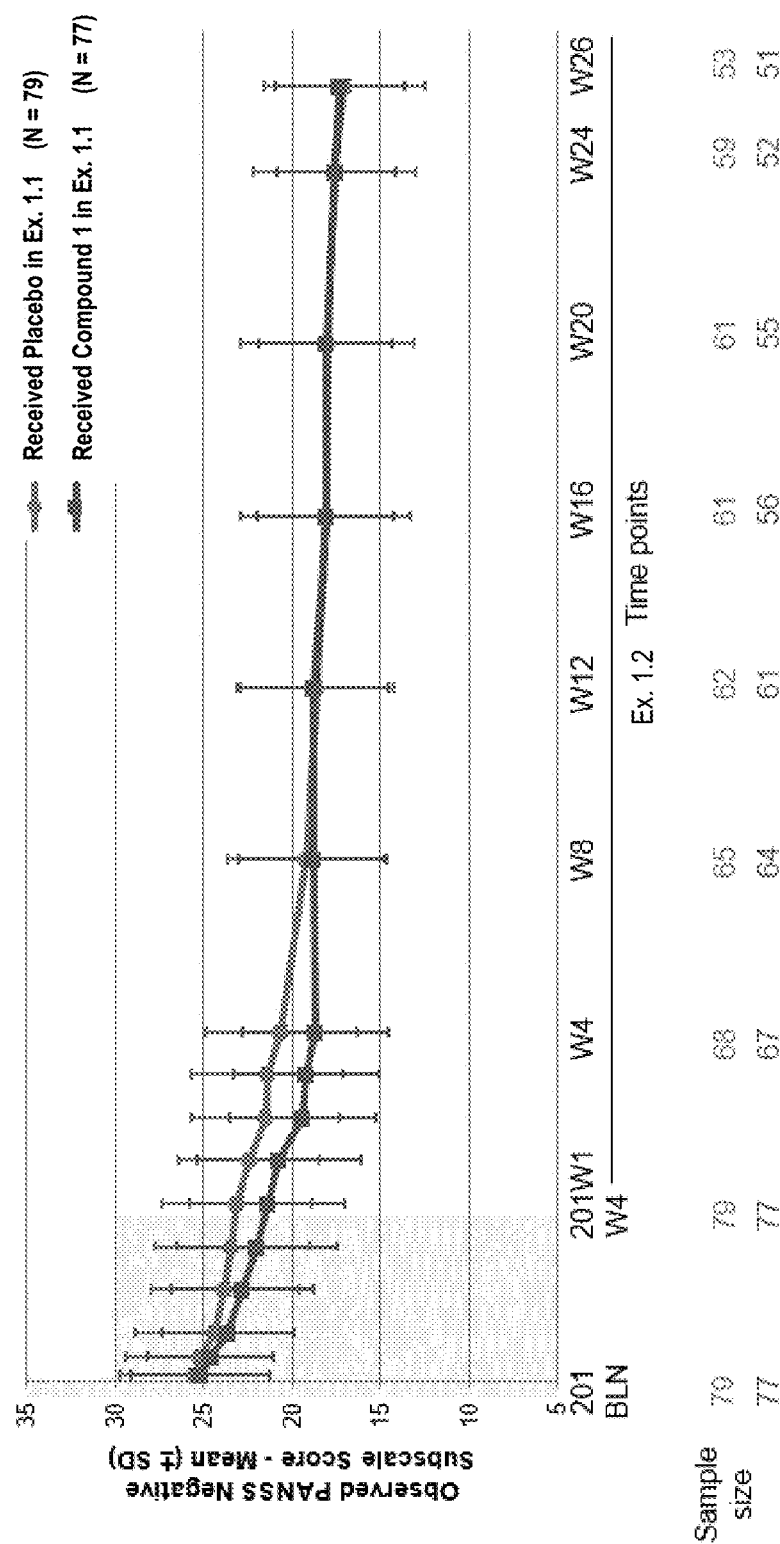
FIG. 11 shows the observed PANSS negative subscore during double-blind treatment (Example 1.1) and open-label extension study (Example 1.2).

FIG. 11 shows the PANSS negative subscale score during the extension study with the PANSS negative subscale score data from the Example 1.1 study shown for reference.

Figure 12:
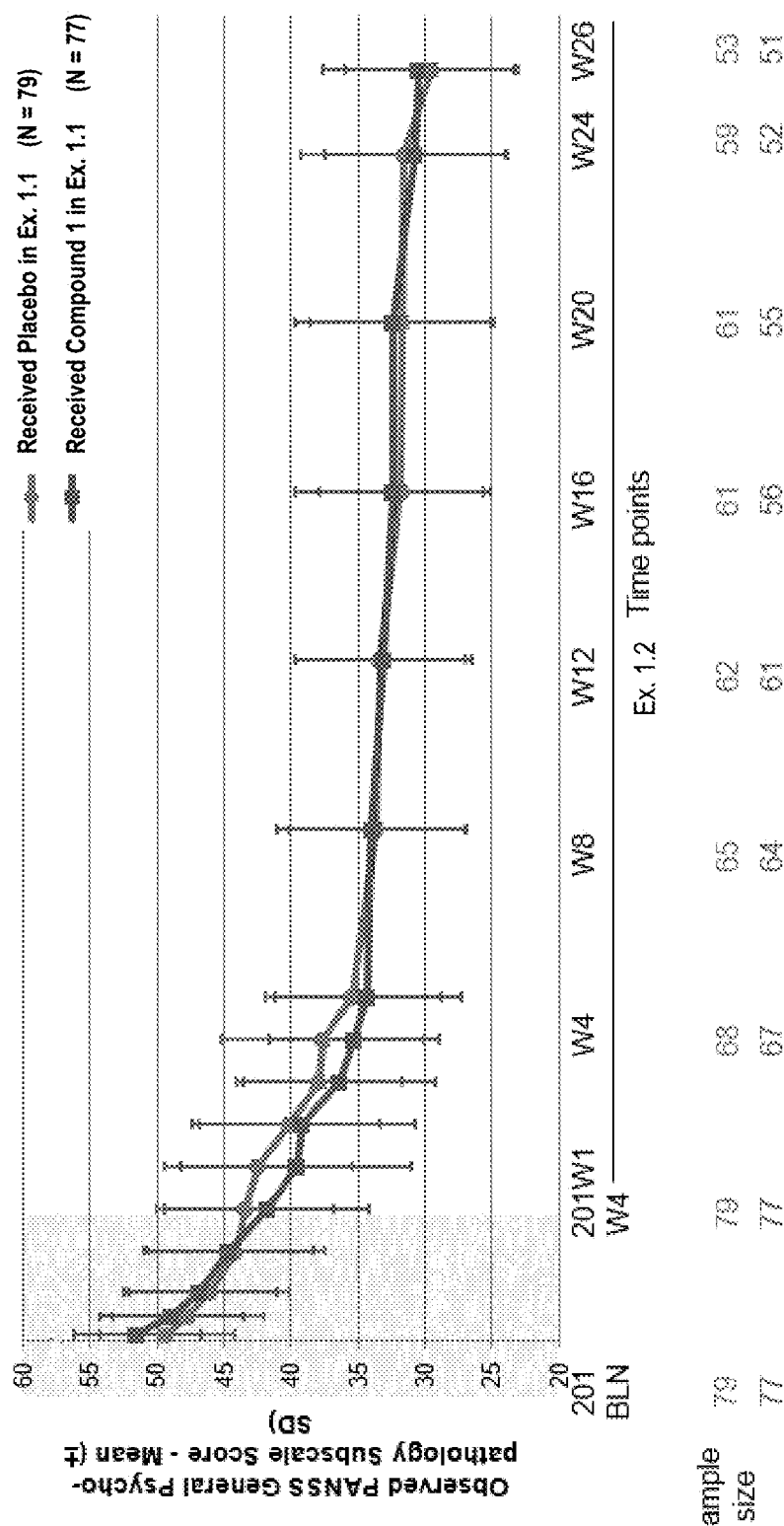
FIG. 12 shows the observed PANSS general psychopathology subscore during double-blind treatment (Example 1.1) and open-label extension study (Example 1.2).

FIG. 12 shows the PANSS general psychopathology subscale score during the extension study with the PANSS general psychopathology subscale score data from the Example 1.1 study shown for reference.

Figure 13:
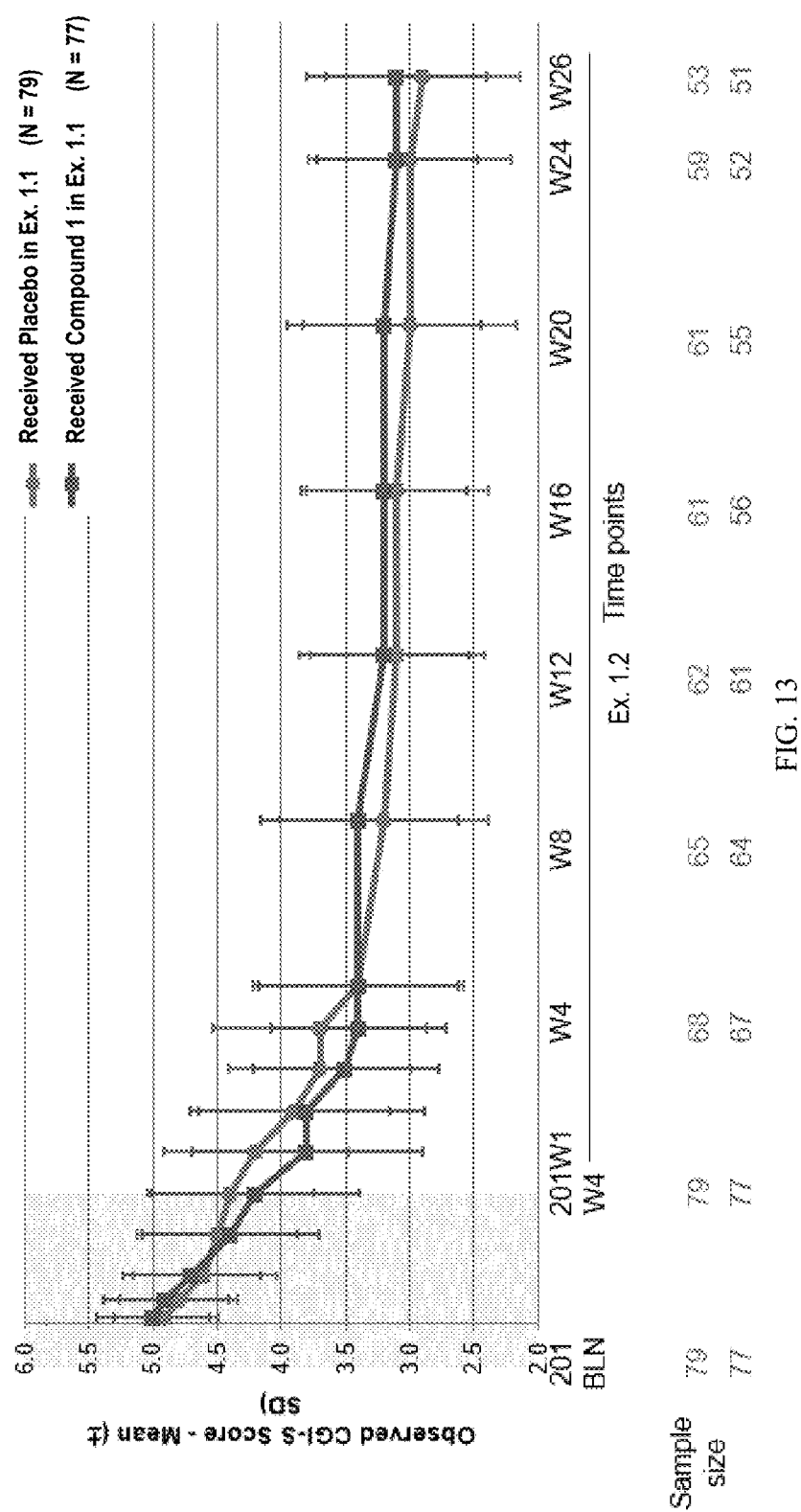
FIG. 13 shows the observed CGI-S score during double-blind treatment (Example 1.1) and open-label extension study (Example 1.2).

FIG. 13 shows the CGI-S score during the extension study with the CGI-S score data from the Example 1.1 study shown for reference.

Figure 14:
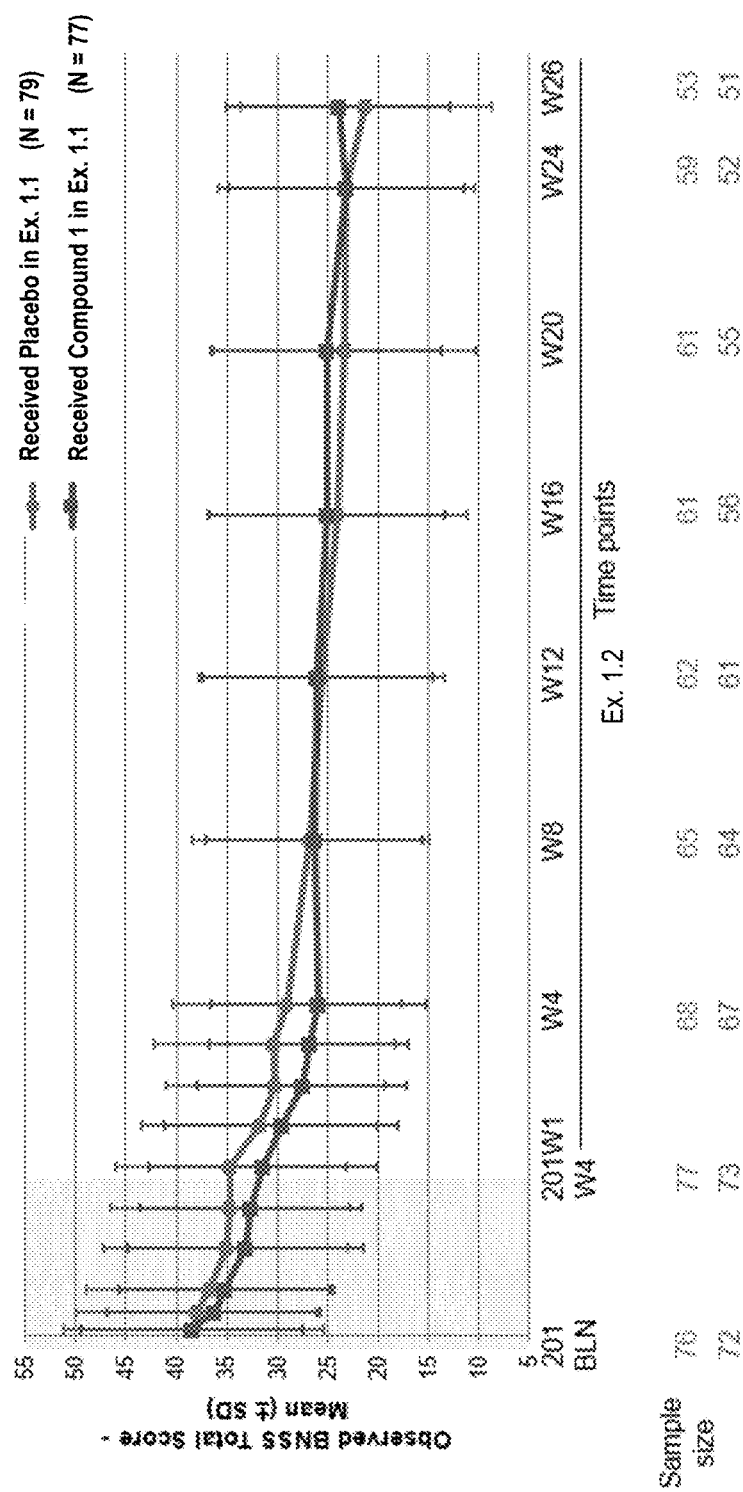
FIG. 14 shows the observed BNSS total score during double-blind treatment (Example 1.1) and open-label extension study (Example 1.2).

FIG. 14 shows the BNSS total score during the extension study with the BNSS total score data from the Example 1.1 study shown for reference.

Figure 15:
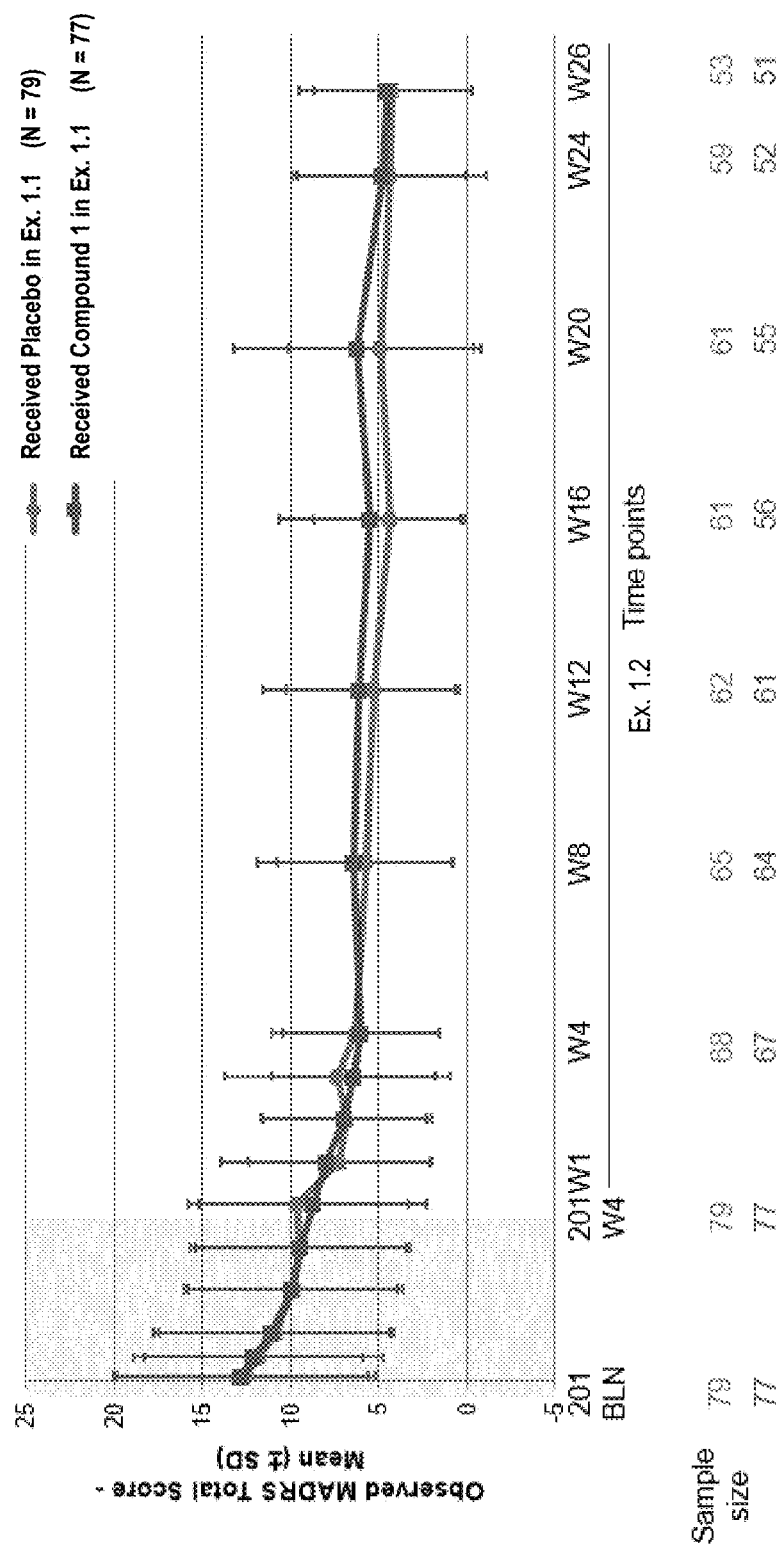
FIG. 15 shows the observed MADRS total score during double-blind treatment (Example 1.1) and open-label extension study (Example 1.2).

FIG. 15 shows the MADRS total score during the extension study with the MADRS total score data from the Example 1.1 study shown for reference.

Adverse events were monitored and recorded during the extension study. The incidence of adverse events remained low in both (i) the subjects who previously received placebo and received active treatment for the first time during the extension study, and (ii) the subjects who continued to receive active treatment from the Example 1.1 study into the extension study. Tables 11-16 show the adverse events experienced during the extension study.

TABLE 11

General Adverse Events

| Preferred Term | Placebo to Compound 1 (N = 79) n (%) | Compound 1 to Compound 1 (N = 77) n (%) | Total (N = 156) n (%) |
| --- | --- | --- | --- |
| Subjects with an AE* | 46 (58.2%) | 42 (54.5%) | 88 (56.4%) |
| Schizophrenia | 11 (13.9%) | 8 (10.4%) | 19 (12.2%) |
| Headache | 11 (13.9%) | 7 (9.1%) | 18 (11.5%) |
| Insomnia | 7 (8.9%) | 6 (7.8%) | 13 (8.3%) |
| Anxiety | 4 (5.1%) | 4 (5.2%) | 8 (5.1%) |
| Nasopharyngitis | 3 (3.8%) | 4 (5.2%) | 7 (4.5%) |
| Somnolence | 5 (6.3%) | 2 (2.6%) | 7 (4.5%) |
| Nausea | 4 (5.1%) | 2 (2.6%) | 6 (3.8%) |
| Influenza | 3 (3.8%) | 2 (2.6%) | 5 (3.2%) |
| Irritability | 2 (2.5%) | 3 (3.9%) | 5 (3.2%) |
| Weight decreased | 3 (3.8%) | 2 (2.6%) | 5 (3.2%) |
| Blood prolactin increased | 1 (1.3%) | 3 (3.9%) | 4 (2.6%) |

*Subjects with multiple AEs are counted only once.

TABLE 12

Extrapyramidal Symptoms

| Preferred Term | Placebo to Compound 1 (N = 79) n (%) | Compound 1 to Compound 1 (N = 77) n (%) | Total (N = 156) n (%) |
| --- | --- | --- | --- |
| Any subject experiencing an extrapyramidal symptom AE* | 1 (1.3%) | 4 (5.2%) | 5 (3.2%) |
| Parkinsonism | 1 (1.3%) | 1 (1.3%) | 2 (1.3%) |
| Dyskinesia | 0 | 1 (1.3%) | 1 (0.6%) |
| Tremor | 0 | 1 (1.3%) | 1 (0.6%) |
| Restlessness | 0 | 1 (1.3%) | 1 (0.6%) |

*Subjects with multiple EPS AEs are counted only once.

TABLE 13

Prolactin-related Adverse Events

| Preferred Term | Placebo to Compound 1 (N = 79) n (%) | Compound 1 to Compound 1 (N = 77) n (%) | Total (N = 156) n (%) |
| --- | --- | --- | --- |
| Any subject experiencing a prolactin-related AE* | 2 (2.5%) | 4 (5.2%) | 6 (3.8%) |
| Hyperprolactinemia | 1 (1.3%) | 0 | 1 (0.6%) |
| Blood prolactin increased | 1 (1.3%) | 3 (3.9%) | 4 (2.6%) |
| Menstruation delayed | 0 | 1 (1.3%) | 1 (0.6%) |

*Subjects with multiple prolactin-related AEs are counted only once.

Figure 16:
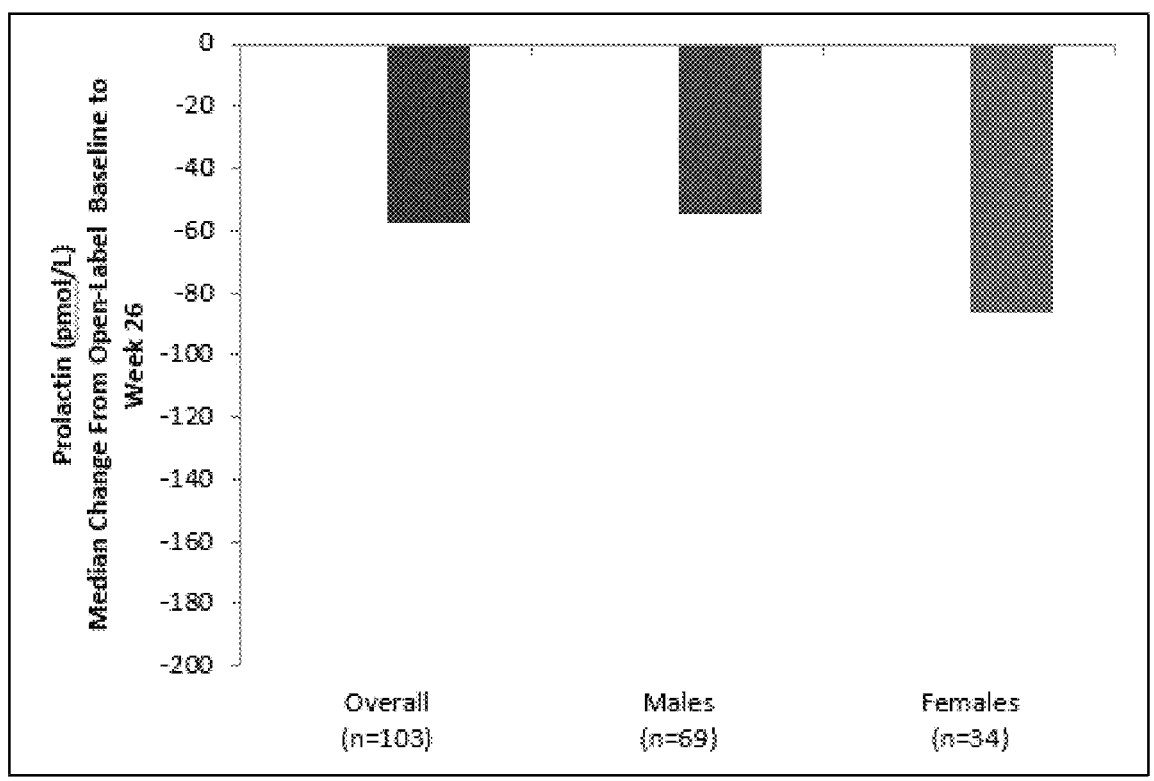
FIG. 16 shows the change from open-label baseline at week 26 in prolactin levels.

The change in prolactin levels from baseline at week 26 are shown in FIG. 16.

TABLE 14

Cardiovascular Adverse Events

| SOC/Preferred Term | Placebo to Compound 1 (N = 79) n (%) | Compound 1 to Compound 1 (N = 77) n (%) | Total (N = 156) n (%) |
|---|---|---|---|
| Cardiac Disorder | 5 (6.3%) | 2 (2.6%) | 7 (4.5%) |
| Sinus tachycardia | 2 (2.5%) | 1 (1.3%) | 3 (1.9%) |
| Atrioventricular block first degree | 0 | 1 (1.3%) | 1 (0.6%) |
| Angina pectoris | 1 (1.3%) | 0 | 1 (0.6%) |
| Sinus arrhythmia | 1 (1.3%) | 0 | 1 (0.6%) |
| Tachycardia | 1 (1.3%) | 0 | 1 (0.6%) |
| Vascular Disorders | 2 (2.5%) | 0 | 2 (1.3%) |
| Hypotension | 2 (2.5%) | 0 | 2 (1.3%) |
| Investigations | | | |
| Heart rate increased | 1 (1.3%) | 0 | 1 (0.6%) |
| Blood pressure increased | 1 (1.3%) | 0 | 1 (0.6%) |
| Nervous System Disorders | | | |
| Dizziness | 1 (1.3%) | 1 (1.3%) | 2 (1.3%) |

*Subjects with multiple AEs are counted only once.

TABLE 15

Serious Adverse Events

| | Placebo to Compound 1 (N = 79) | | Compound 1 to Compound 1 (N = 77) | | Total (N = 156) | |
|---|---|---|---|---|---|---|
| SOC/Preferred Term | n (%) | # Events | n (%) | # Events | n (%) | # Events |
| Subjects with Any SAE* | 9 (11.4%) | 10 | 6 (7.8%) | 6 | 15 (9.6%) | 16 |
| Psychiatric Disorders | 9 (11.4%) | 10 | 5 (6.5%) | 5 | 14 (9.0%) | 15 |
| Schizophrenia | 7 (8.9%) | 7 | 4 (5.2%) | 4 | 11 (7.1%) | 11 |
| Acute psychosis | 1 (1.3%) | 1 | 0 | 0 | 1 (0.6%) | 1 |
| Depression | 1 (1.3%) | 1 | 0 | 0 | 1 (0.6%) | 1 |
| Psychotic disorder | 0 | 0 | 1 (1.3%) | 1 | 1 (0.6%) | 1 |
| Suicidal ideation | 1 (1.3%) | 1 | 0 | 0 | 1 (0.6%) | 1 |
| Reproductive System and Breast Disorders | 0 | 0 | 1 (1.3%) | 1 | 1 (0.6%) | 1 |
| Uterine Hemorrhage | 0 | 0 | 1 (1.3%) | 1 | 1 (0.6%) | 1 |

*Subjects with multiple SAEs are counted only once.

TABLE 16

Adverse Events Leading to Discontinuation

| | Placebo to Compound 1 (N = 79) | | Compound 1 to Compound 1 (N = 77) | | Total (N = 156) | |
|---|---|---|---|---|---|---|
| Preferred Term | n (%) | # Events | n (%) | # Events | n (%) | # Events |
| Any AE leading to discontinuation from study* | 9 (11.4%) | 9 | 9 (11.7%) | 9 | 18 (11.5%) | 18 |
| Schizophrenia | 7 (8.9%) | 7 | 7 (9.1%) | 7 | 14 (9.0%) | 14 |
| Acute Psychosis | 1 (1.3%) | 1 | 0 | 0 | 1 (0.6%) | 1 |
| Anxiety | 0 | 0 | 1 (1.3%) | 1 | 1 (0.6%) | 1 |
| Depression | 1 (1.3%) | 1 | 0 | 0 | 1 (0.6%) | 1 |
| Psychotic disorder | 0 | 0 | 1 (1.3%) | 1 | 1 (0.6%) | 1 |

*Subjects with multiple AEs are counted only once.

Figure 20A:
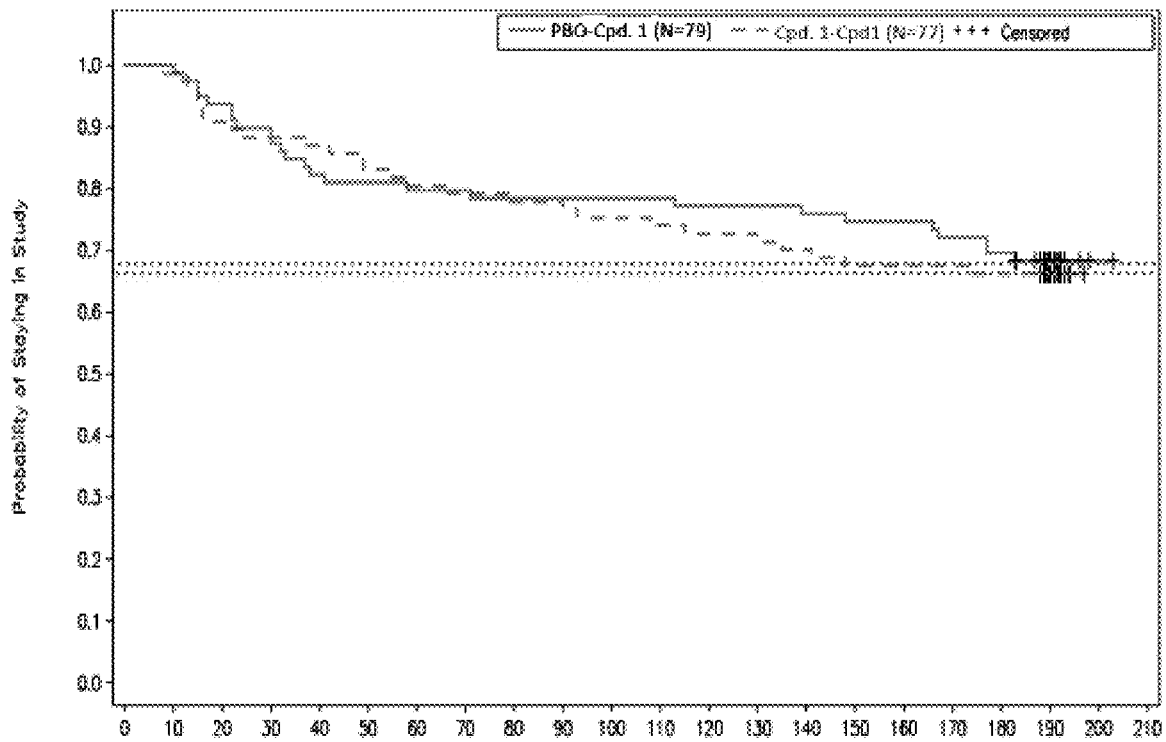
FIG. 20A and FIG. 20B show FIG. 20A the time to all causes of discontinuation in the study of Example 1.2 and FIG. 20B comparative data for other drugs.
Figure 20B:
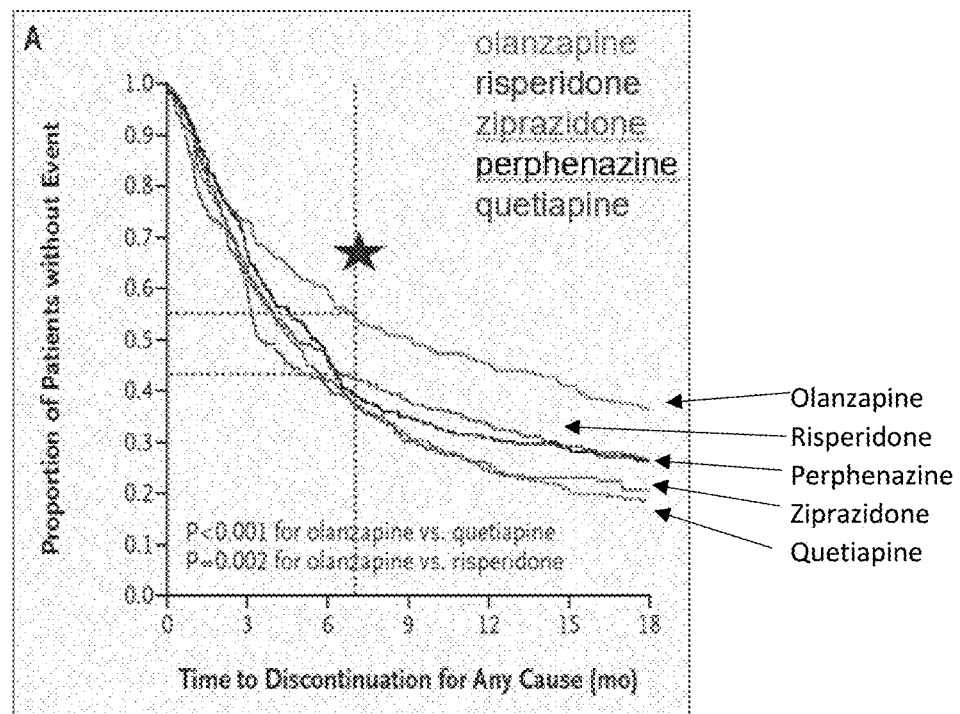

FIG. 20A shows the time to all causes of discontinuation in the extension study. FIG. 20B shows the time to discontinuation for several other drugs: olanzapine, risperidone, ziprazidone, perphenazine, and quetiapine.

Figure 17A:
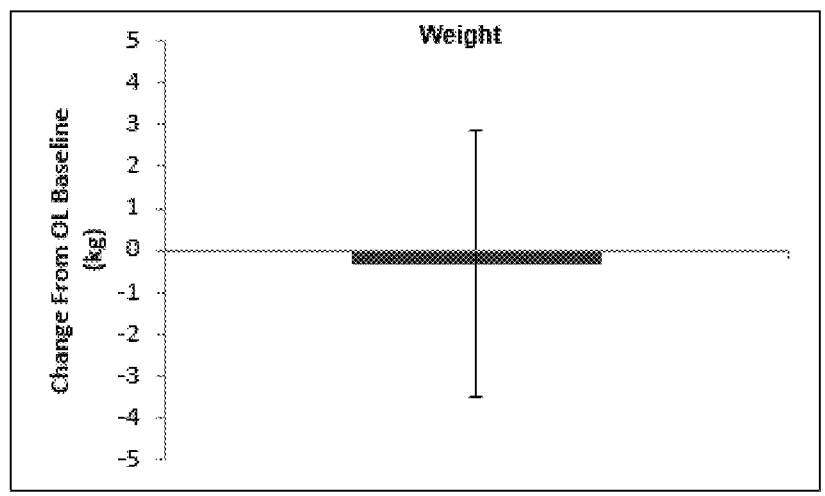
FIG. 17A and FIG. 17B show the change from open-label baseline at week 26 in FIG. 17A weight and FIG. 17B body mass index (BMI).
Figure 17B:
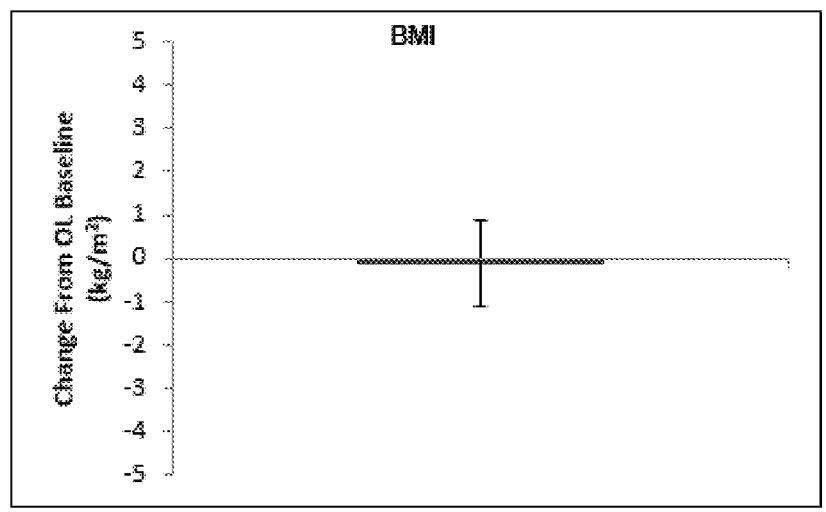
Figure 19A:
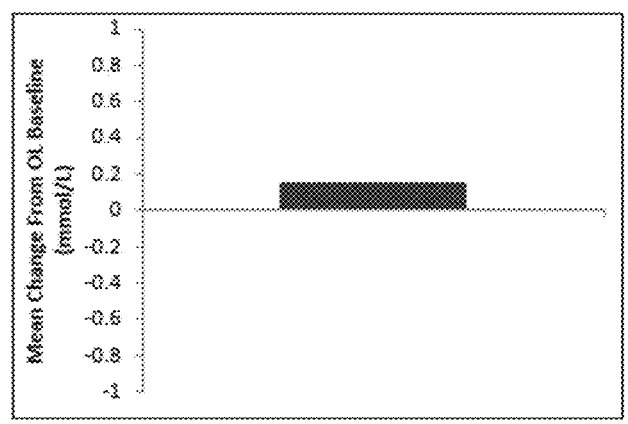
FIG. 19A and FIG. 19B show the change from open-label baseline at week 26 in glycemic measures.
Figure 19B:
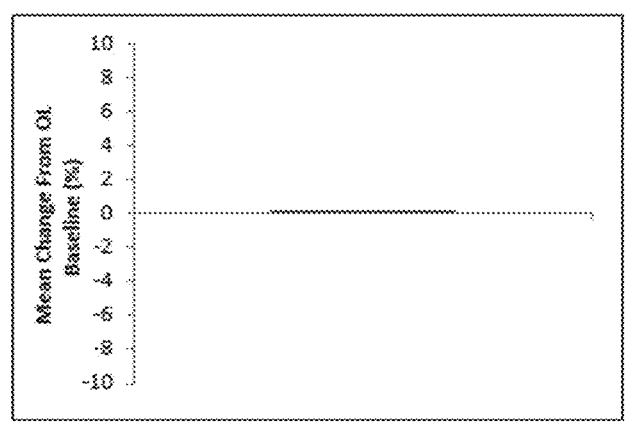

Additional clinical measurements were taken during the study. The change in weight and BMI from open-label baseline (i.e., at start of extension study) at week 26 are shown in FIGS. 17 A and B. The change in lipid measurements (total cholesterol, triglycerides, HDL, LDL) from open-label baseline are shown in FIG. 18 A-D. The change in glycemic measures (glucose, HbA1c) from open-label baseline are shown in FIGS. 19 A and B.

Functional improvement was also measured by UPSA-B score, a performance-based skills assessment. Compound 1 improved UPSA-B total score in the subjects from an average of about 76 to an average of about 84 (effect size of 0.66) during the 26-week period.

Overall, the extension study demonstrated a high completion rate; continued improvement in symptoms of schizophrenia (i.e., improved efficacy scores); very low incidence of EPS-related, prolactin-related, and cardiovascular-related adverse events; and minimal changes in weight, lipids and glycemic measures.

Example 1.3: 6-Week Clinical Trial (Parkinson's Disease Psychosis)

Compound 1 was evaluated in adults ≥55 years of age with a clinical diagnosis of Parkinson's disease psychosis to study the efficacy, safety and tolerability of Compound 1 in subjects with Parkinson's disease psychosis in a multicenter, randomized, parallel-group, placebo-controlled study. Eligible patients met established National Institutes of Neurological Disorders and Stroke/National Institutes of Mental Health (NINDS/NVIH) diagnostic criteria for Parkinson's disease psychosis, including idiopathic Parkinson's disease consistent with UK Brain Bank criteria lasting ≥1 year, had psychotic symptoms that developed after Parkinson's disease diagnosis present for ≥1 month, occurred at least weekly in the month before screening, and were severe enough to warrant treatment with antipsychotics. Patients had to have clinically significant Parkinson's disease psychosis with a combined score of ≥6 or an individual score of ≥4 on the Neuropsychiatric Inventory (NPI) Item A (delusions) and/or Item B (hallucinations) at screening (Visit 1) and baseline (Visit 3). Patients were on stable doses of dopaminergic and other therapies for Parkinson's disease motor symptoms for ≥1 month prior to screening and during the trial. Patients had to have mini-mental status examination (MMSE) score of ≥16 points out of 30, and a caregiver was required at study visits.

According to the diagnostic criteria, patients were excluded if their psychosis was atypical or secondary to medication or other neurodegenerative disorders, had dementia diagnosed concurrent or prior to PD or with other toxic or metabolic disorders, if motor symptoms began <1 year prior to onset of dementia or symptoms were consistent with Lewy Body Dementia. Patients who had experienced lack of efficacy in response to adequate doses of ≥2 antipsychotic drugs within 1 year of screening were excluded. Other exclusion criteria included stroke or other uncontrolled neurological illness <6 months prior to baseline, suicidal ideations at screening or baseline, or any clinically significant medical condition or chronic disease that would limit the patient's ability to participate in the study. Patients were excluded if they underwent surgical treatment for PD.

Standard Protocol Approvals and Patient Consents

In compliance with the Declaration of Helsinki, patients provided written informed consent. Participating centers received institutional review board approval. Caregivers also provided consent for the patient to participate in the study as well as consent for collection of caregiver data as related to the assessment of the patient's neuropsychiatric status (measured by the NPI).

Study Design

This study evaluated the efficacy, safety, and tolerability of double-blind Compound 1 flexibly dosed at 25, 50, or 75 mg/day. The study consisted of a screening/washout period (up to 14 days prior to double-blind treatment) and a double-blind treatment period (6 weeks). During screening, any antipsychotic or centrally acting anticholinergic medications were tapered and stopped. Prior treatment with antipsychotic agents was discontinued ≥5 half-lives prior to performing the NPI and MMSE screening assessments.

The study included an addition of a 12-week open-label period after completion of the double-blind period to provide long-term safety and tolerability information.

At baseline (Day 1), patients who had successfully completed the screening/washout period were randomly assigned in a 2:1 ratio to Compound 1 or placebo. Double-blind study drug was taken in-clinic at baseline and on visit days when the patient up-titrated. Subsequent doses starting the following day, were to be taken at bedtime. Patients randomized to Compound 1 received 25 mg/day for 1 week (Days 1 to 7). If there were no safety or tolerability issues, they were up-titrated to 50 mg/day at Week 2 and 75 mg/day at Week 3. Patients still receiving 25 mg/day were to have their dose up-titrated to 50 mg/day at Week 3 unless there were safety and tolerability concerns. Up-titration was not allowed after Week 5. Dose reductions to 50 mg/day or 25 mg/day were allowed by 1 dose level at any time for reasons of safety and tolerability. Patients who completed the double-blind treatment period could continue into the open-label extension.

Assessments were done at screening, baseline, and weekly study visits (see Table 1.3.1 for score ranges of assessment scales).

TABLE 1.3.1

| Patient Demographics and Clinical Characteristics (mITT population) | | | | |
|---|---|---|---|---|
| | Statistic | Placebo (n = 14) | Compound 1 (n = 24) | Total (N = 38) |
| Age (Years) | Mean (SD) | 71.8 (7.12) | 70.0 (7.24) | 70.7 (7.15) |
| ≥55 to <65 | n (%) | 2 (14.3%) | 5 (20.8%) | 7 (18.4%) |
| ≥65 to <75 | n (%) | 7 (50.0%) | 12 (50.0%) | 19 (50.0%) |
| ≥75 | n (%) | 5 (35.7%) | 7 (29.2%) | 12 (31.6%) |
| Gender (Male) | n (%) | 13 (92.9%) | 20 (83.3%) | 33 (86.8%) |

TABLE 1.3.1-continued

Patient Demographics and Clinical Characteristics (mITT population)

|  | Statistic | Placebo (n = 14) | Compound 1 (n = 24) | Total (N = 38) |
|---|---|---|---|---|
| Race |  |  |  |  |
| Asian | n (%) | 0 | 1 (4.2%) | 1 (2.6%) |
| Native Hawaiian/Pacific Islander | n (%) | 1 (7.1%) | 0 | 1 (2.6%) |
| White | n (%) | 12 (85.7%) | 23 (95.8%) | 35 (92.1%) |
| Other | n (%) | 1 (7.1%) | 0 | 1 (2.6%) |
| Time Since Onset of PD (Years) | Mean (SD) | 2.3 (2.36) | 2.4 (2.50) | 2.4 (2.41) |
| <5 years | n (%) | 13 (92.9%) | 22 (91.7%) | 35 (92.1%) |
| 5 to <10 years | n (%) | 1 (7.1%) | 1 (4.2%) | 2 (5.3%) |
| 10 to <20 years | n (%) | 0 | 1 (4.2%) | 1 (2.6%) |
| SAPS-PD Total Score (Range 0-45) | Mean (SD) | 14.7 (8.71) | 13.1 (6.04) | 13.6 (7.02) |
| <13 median | n (%) | 6 (46.2%) | 12 (50.0%) | 18 (48.6%) |
| ≥13 median | n (%) | 7 (53.8%) | 12 (50.0%) | 19 (51.4%) |
| SAPS-PD Hallucinations Subscale Score (Range 0-25)[a] | Mean (SD) | 12.0 (6.60) | 10.5 (4.50) | 11.0 (5.29) |
| <10 median | n (%) | 6 (46.2%) | 8 (33.3%) | 14 (37.8%) |
| ≥10 median | n (%) | 7 (53.8%) | 16 (66.7%) | 23 (62.2%) |
| SAPS-PD Delusions Subscale Score (Range 0-20)[b] | Mean (SD) | 2.7 (3.95) | 2.6 (3.71) | 2.6 (3.74) |
| <0.5 median | n (%) | 7 (53.8%) | 12 (50.0%) | 19 (51.4%) |
| ≥0.5 median | n (%) | 6 (46.2%) | 12 (50.0%) | 18 (48.6%) |
| CGI-S Score (Range 0-7) | Mean (SD) | 4.1 (1.27) | 4.1 (1.05) | 4.1 (1.13) |
| <4 | n (%) | 5 (35.7%) | 6 (30.0%) | 11 (32.4%) |
| ≥4 | n (%) | 9 (64.3%) | 14 (70.0%) | 23 (67.6%) |
| NPI (H + D) Score (Range 0-24) | n | 14 | 24 | 38 |
|  | Mean (SD) | 8.6 (4.03) | 10.8 (5.34) | 10.0 (4.96) |
| <6 | n (%) | 3 (21.4%) | 4 (16.7%) | 7 (18.4%) |
| ≥6 to <12 | n (%) | 7 (50.0%) | 10 (41.7%) | 17 (44.7%) |
| ≥12 | n (%) | 4 (28.6%) | 10 (41.7%) | 14 (36.8%) |
| NPI Hallucinations Subscale Score (Range 0-12) | Mean (SD) | 5.1 (2.46) | 7.0 (3.26) | 6.3 (3.10) |
| NPI Delusions Subscale Score (Range 0-12) | Mean (SD) | 3.5 (3.18) | 3.8 (4.05) | 3.7 (3.71) |
| MMSE Score (Range 0-30) | Mean (SD) | 24.7 (3.20) | 25.1 (4.07) | 25.0 (3.73) |
| ≤24 | n (%) | 7 (50.0%) | 7 (29.2%) | 14 (36.8%) |
| ≤24 | Mean (SD) | 22.0 (1.15) | 19.7 (3.15) | 20.9 (2.57) |
| >24 | n (%) | 7 (50.0%) | 17 (70.8%) | 24 (63.2%) |
| >24 | Mean (SD) | 27.4 (1.90) | 27.3 (1.53) | 27.3 (1.61) |

[a]The SAPS-PD subscale for hallucinations was defined as the sum of the 4 items for hallucinations and the global hallucination item.
[b]The SAPS-PD subscale for delusions was defined as the sum of the 3 items for delusions and the global delusion item.
CGI-S, Clinical Global Impression-Severity Scale; mITT, modified intent-to-treat; MMSE, mini-mental state examination; NPI (H + D), Neuropsychiatric Inventory (Hallucination + Delusion); PDP, Parkinson's disease psychosis; SAPS-PD, Scale for Assessment of Positive Symptoms-Parkinson's Disease; SD, standard deviation.

The primary outcome was change in total Scale for Assessment of Positive Symptoms-Parkinson's Disease (SAPS-PD) score from baseline to week 6 (Day 43). The SAPS-PD includes 9 items, 7 assessing individual symptoms, a global hallucinations item, and a global delusions item. SAPS-PD was evaluated by centralized blinded raters who had been trained and calibrated. Other secondary efficacy endpoints at week 6 included the proportion of patients who achieved a reduction on the total SAPS-PD score by ≥30%, ≥50% and ≥100%, change from baseline in SAPS-PD Hallucination and Delusion subscale scores, change from baseline in the Clinical Global Impressions-Severity (CGI-S) score, NPI hallucinations+delusions score, the Scales for Outcomes in Parkinson's Disease Sleep Scale-Daytime Sleepiness (SCOPA-DS) and nighttime sleep (SCOPA-NS), the MMSE score. To assess the impact of treatment with Compound 1 on motor symptoms of Parkinson's disease, change from baseline to week 6 on the Unified Parkinson's Disease Rating Scale (UPDRS) Part III motor score was included. Safety assessments included adverse events (AEs), serious AEs, AEs resulting in discontinuation, electrocardiogram (ECG), vital signs, laboratory assessments, and suicidal ideations as measured by the Columbia-Suicide Severity Rating Scale (C-SSRS). Patients were assessed for orthostatic hypotension based on prespecified criteria: orthostatic hypotension was defined as a decrease of ≥20 mmHg in systolic blood pressure or ≥10 mmHg in diastolic blood pressure.

Statistical Analysis

Sample size was determined for the purposes of exploring the efficacy, safety, and tolerability of flexible dosing with Compound 1 (25, 50, or 75 mg/day) for 6 weeks. A sample size of 36 patients was determined to detect treatment effect sizes of approximately 0.5 in change from baseline in SAPS-PD total score at Week 6 for Compound 1 versus placebo. It was estimated by using a 2 independent sample t-test method with a 2-sided significance level of 0.05. Approximately 36 patients were to be randomized 2:1 to Compound 1 and placebo. The safety population included all patients who were randomized and received ≥1 dose of study drug during the double-blind treatment period. The modified intent-to-treat (mITT) population was defined as all patients who were randomized, received ≥1 dose of study drug, and had a baseline and ≥1 postbaseline total score in SAPS-PD, NPI, or CGI-S during the double-blind treatment period. The mITT population was the primary population for efficacy analyses. For selected efficacy measures, such as the primary and secondary endpoints, change from baseline was assessed with the mixed model for repeated measures (MMRM) method that included factors for treatment, visit (as a categorical variable), and treatment-by-visit interaction, and included baseline score as a covariate.

Results

Patients

Eighty patients were screened with 25 randomly assigned to receive Compound 1 and 14 assigned to receive placebo. Of randomized patients, 60.0% on Compound 1 and 78.6% on placebo completed double-blind treatment. The most common reason for discontinuation was AEs (5/10 patients) in the Compound 1 group and study withdrawal (⅔ patients) in the placebo group. Seventeen (43.6%) patients were on antipsychotic or centrally acting anticholinergic agents prior to screening and washout; 17.9% were on pimavanserin, 15.4% on quetiapine, and 2.6% on risperidone. One patient randomized to Compound 1 was not included in the mITT efficacy analysis. Table 1.3.1 shows the baseline demographics and clinical characteristics for the mITT population. Mean (range) time since onset of PD was 9.0 (2.4-20.7) years. Overall, baseline SAPS-PD, NPI, MMSE, and CGI-S scores indicate that the patient population enrolled had predominantly hallucinations versus delusions at baseline. Significant cognitive impairment (MMSE≤24) was present in 36.8% of patients at baseline. There were no notable differences at baseline between treatment groups on these scales.

Mean (range) duration of exposure was 32.1 (2-43) days for Compound 1 and 37.4 (9-45) days for placebo. All patients received 25 mg for 1 week. In the Compound 1 treatment group, 50.0% were up titrated to 75 mg by Week 3 and more than half (59.1%) received 75 mg by Week 5. Dose exposure was similar for those patients receiving the placebo equivalent.

Efficacy

Treatment with Compound 1 resulted in improvement in symptoms of psychosis as measured by SAPS-PD total scores after 6 weeks. Least-squares (LS) mean standard error (SE) change from baseline at Week 6 of −2.5 (1.62) and −1.4 (2.0) did not demonstrate a statistically significant difference (p=nonsignificant [ns]) for Compound 1 and placebo, respectively. Reduction in SAPS-PD total scores were observed as early as Week 1 with all patients on 25 mg Compound 1 and consistently through Week 6. SAPS-PD responders were defined as patients with ≥30%, ≥50%, and ≥100% improvement (reduction) from baseline, respectively, in SAPS-PD total scores. At Week 6, both ≥30% response and ≥50% response was achieved by 37.5% of patients in the Compound 1 group and 27.3% of patients in the placebo group. Resolution of symptoms of psychosis (i.e., 100% response) at week 6 was seen in 25.0% of patients in the Compound 1 group and no patients in the placebo group.

Treatment with Compound 1 resulted in improvement in hallucinations as measured by SAPS-PD hallucinations scores after 6 weeks of treatment. LS mean (SE) change in SAPS-PD hallucinations subscale scores from baseline at Week 6 were −3.6 (1.07) and −1.9 (1.35; p=ns) for Compound 1 versus placebo, respectively. Reduction in SAPS-PD total scores were observed as early as 1 week for patients on Compound 1 and consistently through Week 6. Conversely, there was no improvement on SAPS-PD delusions subscale scores and at Week 6 SAPS-PD delusions subscale scores showed slight worsening in the Compound 1 group.

Studies have demonstrated that cognitive impairments may impact treatment of patients with PDP. To assess the efficacy of Compound 1 in patients with Parkinson's disease and cognitive impairment, an exploratory analysis was done in patients with MMSE of ≤24 (indicative of cognitive impairment) and patients with MMSE >24. Treatment of patients with baseline MMSE scores ≤24 with Compound 1 resulted in improvement in SAPS-PD total scores at Week 6. LS mean (SE) change in SAPS-PD total scores from baseline at Week 6 was −5.2 (2.81) and −2.1 (3.00; p=ns) for Compound 1 and placebo, respectively. Reduction in SAPS-PD total scores was observed at Week 1 and throughout the 6-week treatment period. For patients with MMSE scores of >24, no consistent reduction in SAPS-PD total scores were observed throughout the 6-week treatment period. LS mean (SE) change from baseline at Week 6 was −1.3 (2.03) for Compound 1 and −0.4 (2.94) for placebo. Treatment with Compound 1 did not affect MMSE scores. LS mean (SE) change from baseline in MMSE scores at week 6 was −0.8 (0.48) and 0.3 (0.55) for Compound 1 and placebo (p=ns), respectively.

There were no significant differences between Compound 1 and placebo groups in the change from baseline at Week 6 for CGI-S scores with LS mean (SE) change from baseline at Week 6 of −0.4 (0.33) and −0.7 (0.39) for Compound 1 and placebo (p=ns), respectively. NPI total scores, and NPI hallucinations+delusions scores were not different between Compound 1 and placebo. The NPI hallucination subscale scores for the Compound 1 group showed improvement at Week 6. LS mean (SE) change from baseline in NPI hallucinations subscale scores at Week 6 was −2.5 (0.77) and −0.8 (0.97; p=ns) for Compound 1 and placebo, respectively. At Week 6, significant improvement (p=0.022) was observed in the change from baseline in LS mean (SE) SCOPA-DS scores for patients receiving Compound 1 (−1.8 [0.74]) versus placebo (0.9 [0.80]). Conversely, no improvement was observed in change from baseline at Week 6 for SCOPA-NS scores. LS mean (SE) SCOPA-NS scores at Week 6 were −0.1 (0.73) and 0.2 (0.79; p=ns) for Compound 1 and placebo, respectively Safety To assess whether treatment with Compound 1 has an impact on motor symptoms of PD, UPDRS Part III scores were measured at baseline and post baseline study visits. Mean (SD) baseline UPDRS Part III scores were 33.4 (10.28) and 35.9 (13.12) for Compound 1 and placebo groups, respectively. No consistent changes were observed in LS mean (SE) change from baseline in UPDRS Part III scores for Compound 1 and placebo groups through Week 6.

Overall, 18 (72.0%) patients in the Compound 1 group experienced 65 AEs and 12 (85.70) patients in the placebo group experienced 32 AEs. Two patients in the Compound 1 group experienced serious AEs: hip fracture and altered mental state, respectively; neither event was considered related to treatment and both resolved. Five patients in the Compound 1 group each experienced AEs that resulted in discontinuation. No deaths were reported.

AEs by dose at time of event onset are shown in Table 1.3.2.

TABLE 1.3.2

Adverse Events In ≥2 Patients At Any Dose of Compound
1 or Placebo By Dose At Onset of Event (Safety Population)

| System Organ Class/Preferred Term, n (%) | Compound 1 25 mg (n = 11) | Compound 1 50 mg (n = 9) | Compound 1 75 mg (n = 10) | Placebo (n = 12) |
|---|---|---|---|---|
| Any adverse event | 11 (100) | 9 (100) | 10 (100) | 12 (100) |
| Gastrointestinal disorders | 3 (27.3) | 2 (22.2) | 0 | 3 (25.0) |
| Nausea | 2 (18.2) | 1 (11.1%) | 0 | 1 (8.3%) |
| General disorders and administration site conditions | 2 (18.2) | 2 (22.2) | 0 | 3 (25.0) |
| Fatigue | 1 (9.1) | 1 (11.1) | 0 | 2 (16.7) |
| Injury, poisoning and procedural complications | 0 | 3 (33.3) | 3 (30.0) | 4 (33.3) |
| Fall | 0 | 3 (33.3) | 1 (10.0) | 3 (25.0) |
| Investigations | 2 (18.2) | 0 | 1 (10.0) | 0 |
| Nervous system disorder | 3 (27.3) | 4 (44.4) | 1 (10.0) | 3 (25.0) |
| Dizziness | 2 (18.2) | 4 (44.4) | 0 | 1 (8.3) |
| Somnolence | 2 (18.2) | 1 (11.1) | 1 (10.0) | 0 |
| Psychiatric disorders | 3 (27.3) | 6 (66.7) | 6 (60.0) | 6 (50.0) |
| Confusional state | 1 (9.1) | 1 (11.1) | 3 (30.0) | 2 (16.7) |
| Hallucinations | 2 (18.2) | 3 (33.3) | 2 (20.0) | 2 (16.7) |
| Insomnia | 0 | 2 (22.2) | 0 | 1 (8.3) |
| Vascular disorders | 1 (9.1) | 1 (11.1) | 0 | 3 (25.0) |
| Hypertension | 1 (9.1) | 0 | 0 | 2 (16.7) |

The most common AEs (≥100%) for Compound 1 versus placebo included hallucinations (24% vs 140%), confusional state (20% vs 140%), dizziness (16% vs 70%), nausea (12% vs 70%), falls (12% vs 21%), and fatigue (8% vs 14%). Overall, the incidence of psychiatric AEs was higher in the Compound 1 50 mg and 75 mg dose groups compared with the 25 mg dose group. The incidence of confusional state was highest in patients receiving 75 mg Compound 1.

Overall, the incidence of patients with orthostatic hypotension predose and postdose was similar in the Compound 1 group compared with placebo. There were no clinically meaningful changes in ECG parameters, laboratory values, or the C-SSRS over the course of the study. This study suggests that the improvements in symptoms of Parkinson's disease psychosis with Compound 1 occurred without worsening of motor function as demonstrated by the lack of worsening in UPDRS Part III scores.

Example 2: Class-Effect Adverse Events Across Antipsychotics

The antipsychotic class of pharmaceutical compounds is, in part, characterized by certain adverse event risks associated with their use in treating schizophrenia, bipolar and depression patient populations. The Medical Dictionary for Regulatory Activities (MedDRA) is an internationally used set of terms relating to medical conditions, medicines and medical devices, including adverse events. Using MedDRA's standardization of terms (preferred terms), a list of preferred terms of antipsychotic-class related adverse events was established based on reportings to the FDA real-world Adverse Event Reporting Database (FAERS). In particular, FAERS was used to identify preferred terms associated with the 11 most recently FDA-approved antipsychotics (aripiprazole, asenapine, brexpiprazole, cariprazine, iloperidone, lurasidone, olanzapine, paliperidone, quetiapine, risperidone, and ziprasidone). The preferred terms cover a variety of medical systems and organs symptoms. A total of over 9,500 adverse event records were generated using 2018 2nd Quarter data deployed into the Empirica Signal server.

The preferred terms for adverse events of the pool of 11 antipsychotics were ranked by relative risk using a calculated empirical bayes geometric mean (EBGM). Preferred terms that correspond to individual symptoms of schizophrenia and/or bipolar disorders, such as those that correspond with individual items of a psychiatric rating scale used in clinical trials of schizophrenia or bipolar disorder (e.g., PANSS, MADRS) were selected and flagged as disease-related and were not analyzed as side effects of medication. A higher EBGM value for a given drug corresponds with a greater statistical association between the preferred term/adverse event and the drug, compared to all other drugs and all other preferred terms/adverse events. Here, a rank ordering by EBGM values was created to list the preferred terms/adverse events describing the effect of antipsychotics (calculated as an overall pool of 11 antipsychotics) as a class. Accordingly, a compound that causes a clinically significant portion of the treated patient population to have adverse events with preferred terms among the high-ranking (for example, the preferred terms having EGBM values above a threshold) can be considered to have an adverse event profile similar to the class of antipsychotics.

In an example, the preferred terms of association for the pool of 11 antipsychotics are shown in Table 17 below. A compound exhibiting a clinically significant portion of a patient population with adverse events matching these exemplified preferred terms can be considered to have an adverse event profile similar to the class of antipsychotics.

TABLE 17

Selected Preferred Terms of Greatest Association
for the Pool of 11 Antipsychotics

| Adverse Event (Preferred Term) | Empirical Bayes Geometric Mean (EBGM) |
|---|---|
| Hyperprolactinaemia | 30.7 |
| Blood prolactin abnormal | 24.7 |
| Blood prolactin increased | 20.5 |
| Galactorrhoea | 19.4 |
| Cogwheel rigidity | 17.9 |
| Obesity | 17.9 |

TABLE 17-continued

Selected Preferred Terms of Greatest Association
for the Pool of 11 Antipsychotics

| Adverse Event (Preferred Term) | Empirical Bayes Geometric Mean (EBGM) |
|---|---|
| Metabolic syndrome | 17.7 |
| Akathisia | 15.4 |
| Oromandibular dystonia | 15.3 |
| Parkinsonism | 12.3 |
| Drooling | 10.4 |
| Oculogyric crisis | 9.35 |
| Obsessive-compulsive disorder | 9.17 |
| Muscle rigidity | 8.6 |
| Type 2 diabetes mellitus | 8.44 |
| Diabetes mellitus | 8.39 |
| Overweight | 8.01 |
| Parkinsonian gait | 7.69 |
| Tongue spasm | 7.42 |
| Tardive dyskinesia | 7.24 |
| Bradykinesia | 7.18 |
| Tic | 6.59 |
| Psychomotor retardation | 6.51 |
| Extrapyramidal disorder | 6.42 |
| Enuresis | 6.4 |
| Glucose tolerance impaired | 6.22 |
| Salivary hypersecretion | 6.21 |
| Dystonia | 6.09 |
| Glycosuria | 6.09 |
| Restlessness | 6.02 |
| Torticollis | 6.02 |
| Impaired fasting glucose | 5.88 |
| Dermatillomania | 5.88 |
| Body mass index increased | 5.81 |
| Hyperkinesia | 5.69 |
| Hepatitis viral | 5.64 |
| Dyskinesia | 5.59 |
| Blood triglycerides increased | 5.52 |
| Electrocardiogram QT prolonged | 5.44 |
| Dyssomnia | 5.34 |
| Orthostatic hypertension | 5.29 |
| Bruxism | 5.11 |
| Increased appetite | 5.1 |
| Excessive eye blinking | 5.01 |
| Pancreatitis chronic | 4.94 |
| Weight increased | 4.86 |
| Dyslipidaemia | 4.75 |
| Restless legs syndrome | 4.22 |
| Tongue biting | 4.2 |
| Nuchal rigidity | 4.13 |

The over 9,500 preferred terms for adverse events of the pool of 11 antipsychotics were used to query clinical trial data from Example 1.1 (4 week study). The ranking, by EBGM, of the preferred terms for Compound 1 is provided in Table 18. Compound 1 demonstrated a clinically insignificant occurrence of adverse events (e.g., hyperprolactinaemia, blood prolactin abnormal, blood prolactin increased, galactorrhoea, cogwheel rigidity, obesity, metabolic syndrome, etc.) associated with the current antipsychotic class, as defined by the preferred terms of greatest relative risk in real-world adverse event reporting databases (e.g., class-related adverse events). Also, preferred terms observed in subjects who were administered placebo as a comparator to Compound 1 showed similar occurrence of adverse events. Accordingly, Compound 1 does not exhibit an adverse event profile matching the antipsychotic class effect.

TABLE 18

Preferred Terms of Greatest Association for Compound 1 and
Placebo Based on Example 1.1 (4 Week Study) Clinical Data

| Adverse Event (Preferred Term) | EBGM | Compound 1 % Subjects with AE | Placebo % Subjects with AE |
|---|---|---|---|
| Akathisia | 15.4 | 0.8 | 1.67 |
| Extrapyramidal disorder | 6.42 | 0.8 | |
| Restlessness | 6.02 | 0.8 | |
| Increased appetite | 5.1 | 0.8 | |
| Pancreatitis chronic | 4.94 | | 0.83 |
| Weight increased | 4.86 | 1.6 | |
| Nuchal rigidity | 4.13 | 0.8 | |

** Empty cells = no adverse event reported matching Preferred Term

Example 3: Pharmacokinetics

The pharmacokinetics (PK), safety, and tolerability of Compound 1 were evaluated in single ascending doses (5 mg to 125 mg and 25 mg to 150 mg) in healthy adult male subjects and in adult male and female patients with schizophrenia, respectively, or as multiple ascending doses (10, 25, 50, 75, and 100 mg, once daily) in adult male and female patients with schizophrenia. Blood samples from time 0 to 144 hours post-dose were collected for PK analysis. Safety evaluations included adverse events, vital signs, clinical laboratory tests, physical and neurological examinations, C-SSRS, 12-lead ECGs, and safety EEGs.

Healthy Adult Male Subjects, Single Ascending Doses

The safety, tolerability and maximum tolerated dose (MTD) of a single oral dose of Compound 1 was tested in 39 normal healthy adult male subjects. To be included, the subject had to be a healthy male between the ages of 18-50 (inclusive), have a BMI between 16-32 kg/m2 (inclusive), have no diagnosis of schizophrenia, and not be using CNS active drugs or CYP2D6 inhibitors concomitantly.

Single doses of Compound 1, at concentrations of 5 mg, 10 mg, 25 mg, 50 mg, 100 mg, and 125 mg were given to the subjects. Six subjects were present in each group, except for the 125 mg group, where nine subjects were administered the dose, and there were 13 placebo subjects. There were no deaths, nor were there clinically significant treatment-emergent changes in laboratory parameters in this study. The results of the plasma PK parameters are shown below in Table 19:

TABLE 19

Plasma PK Parameters Following a Single Oral Dose of Compound 1 In Healthy Adult Male Subjects

| Parameter | 5 mg (N = 6) | 10 mg (N = 6) | 25 mg (N = 6) | 50 mg (N = 6) | 100 mg (N = 5) | 125 mg (N = 9) |
|---|---|---|---|---|---|---|
| $C_{max}$, ng/mL (CV %) | 17.3 (3.7) | 25.7 (5.7) | 65.4 (20.4) | 139 (22.7) | 287 (58.2) | 379 (62.3) |
| $AUC_{0-last}$, h · ng/mL (CV %) | 104 (27) | 223 (31) | 643 | 1116 (15) | 2700 (63) | 4188 (32) |
| $t_{max}$, median, h | 1.25 | 1.75 | 2.51 | 2.50 | 3.00 | 3.00 |
| $t_{1/2}$, median, h | 6.8 (53.0) | 5.7 (30.8) | 11.3 (63.9) | 12.0 (60.3) | 12.2 (61.6) | 13.6 (52.5) |
| $V_z/F$, L (CV %) | 489 (64) | 376 (64) | 657 (48) | 763 (65) | 6450 (223) | 599 (41) |
| CL/F, L/h (CV %) | 49.9 (22.7) | 47.4 (22.5) | 49.2 (66.3) | 45.7 (16.5) | 969 (236) | 34.4 (49.8) |

Adult Male and Female Subjects with Schizophrenia, Single Ascending Doses

A study was performed to evaluate the safety, tolerability and MTD of a single oral dose of Compound 1 in male and female subjects with schizophrenia. To be included, the subjects had to be a male or female between the ages of 18-55 (inclusive) and have a BMI between 19.5 kg/m2 and 37 kg/m2 (inclusive). Additionally, the subjects had to meet Diagnostic and Statistical Manual of Mental Disorders Fourth Edition; Text Revision (DSM-IV-TR) criteria for a primary diagnosis of schizophrenia, and not be using CNS active drugs or CYP2D6 inhibitors concomitantly.

Single doses of Compound 1 at concentrations of 25 mg, 50 mg, 100 mg, and 150 mg were given to the subjects. Nine subjects were present in each group, and there were twelve placebo subjects. There were no deaths, nor were there clinically significant treatment-emergent changes in laboratory parameters in this study. The results of the plasma PK parameters are shown below in Table 20:

TABLE 20

Study 2: Plasma PK Parameters Following Single Oral Dose of Compound 1

| Parameter | 25 mg (N = 9) | 50 mg (N = 9) | 100 mg (N = 9) | 150 mg (N = 9) |
|---|---|---|---|---|
| $C_{max}$, ng/mL (CV %) | 80.0 (18.6) | 208 (80.6) | 366 (96.8) | 450 (152) |
| $AUC_{0-\infty}$, h · ng/mL (CV %) | 694 (43.1) | 1791 (16.4) | 3644 (20.9) | 50.86 (43.2) |
| $t_{max}$, median, h | 1.0 | 1.5 | 1.5 | 4.0 |
| $t_{1/2}$, h (CV %) | 14.4 (8.0) | 12.4 (5.6) | 17.1 (5.6) | 17.5 (7.3) |
| $V_z/F$, l/h (CV %) | 750 (328) | 491 (207) | 685 (217) | 789 (343) |

Study Design: Adult Male and Female Subjects with Schizophrenia, Multiple Ascending Doses: Two-Part Clinical Study: Multiple Dose and 28-Day Open Label This study was conducted in two parts: a multiple dose study and a 28-day open label study. Compound 1 was evaluated in human adult male and female subjects with a diagnosis of schizophrenia to study its safety, tolerability, and pharmacokinetics in the treatment of schizophrenia. The study had two separate parts, enrolling separate cohorts of patients, but utilizing the same study entry criteria. Part A was a multicenter, randomized, single-blind, placebo-controlled, ascending multiple oral dose study, while Part B was a single site, non-randomized, open-label, study that evaluated the safety, tolerability, and pharmacokinetics of 28 days of treatment with a 75 mg/day dose of Compound 1. Efficacy assessments were performed during open-label treatment in Part B.

Study Entry Criteria: Male and female subjects, 18 to 55 years old (inclusive), were eligible for enrollment if they met Diagnostic and Statistical Manual of Mental Disorders Fourth Edition; Text Revision (DSM-IV-TR) criteria for a primary diagnosis of schizophrenia. Subjects had to have a body mass index (BMI) of 19.5-37 kg/m² (inclusive); be clinically stable for the previous 6 months; and have a CGI-S score ≤4; had a PANSS total score ≤80 (with a score ≤4 [moderate-or-less] on the following PANSS items: hostility [P7], uncooperativeness [G8]). The subjects were required to remain drug-free during the study period, including no use of antipsychotic medication, antidepressants or mood stabilizers, or prescription or over-the-counter medication including vitamins and dietary supplements. Permitted medications included OTC analgesics, e.g., acetaminophen, hydrocortisone cream, female contraceptives, and medications for stable conditions (e.g., hypertension or hypercholesterolemia), and limited use of lorazepam and zolpidem were allowed during the washout and treatment period.

Study Design: Multiple Dose (Part A): Sixty subjects were randomized in five ascending dosage cohorts (N=12) and assigned to the following Compound 1 dosage groups: 10 mg, 25 mg, 50 mg, 75 mg, 100 mg (administered orally in a single daily dose while fasting). In each cohort, subjects were randomized in a 3:1 ratio to receive either Compound 1 (N=9) or matching placebo (N=3) for seven days.

Of the 60 subjects randomized, 71.7% were male, the mean age was 41.8 (range, 24-55), 85.0% were African-American, and the mean PANSS total score was 59.4. All but one subject completed the study per protocol. This subject discontinued study due to an SAE of psychotic disorder (judged not to be related to study drug).

Table 21 shows the pharmacokinetic parameters following (A) a single oral dose of the ascending concentrations of Compound 1 on Day 1 and (B) multiple doses of Compound 1 on Day 7:

TABLE 21

Pharmacokinetic Parameters Following (A) Single
Oral Dose, or (B) Multiple Doses of Compound 1

| Parameter | 10 mg (N = 9) | 25 mg (N = 9) | 50 mg (N = 9) | 75 mg (N = 9) | 100 mg (N = 9) |
|---|---|---|---|---|---|
| A. Single Dose (Day 1) | | | | | |
| $C_{max}$, ng/mL (CV %) | 27.0 (38.1) | 95.2 (31.1) | 198 (35.1) | 281 (24.9) | 375 (27.8) |
| $t_{max}$, median, h | 2.0 | 2.0 | 4.0 | 4.0 | 4.0 |
| $AUC_{0-24}$, h · ng/mL (CV %) | 196 | 928 | 1620 | 2296 | 3781 |
| B. Multiple Doses (Day 7) | | | | | |
| $C_{max}$, mean, ng/mL (CV %) | 28.3 (38.3) | 112 (26.6) | 203 (16.8) | 246 (38.2) | 431 (12.2) |
| $t_{max}$, median, h | 2.0 | 2.0 | 4.0 | 2.0 | 2.0 |
| $t_{1/2}$, h | 21.5 | 21.0 | 20.2 | 21.3 | 21.1 |
| $AUC_{0-24}$, h · ng/mL | 217 | 1158 | 2039 | 2553 | 4718 |
| $V_{SS}/F$, l/h | 2474 | 725 | 716 | 1070 | 650 |
| $CL_{SS}/F$, l/h | 97.7 | 23.8 | 24.7 | 40.5 | 21.9 |

Means shown, except for $t_{max}$ where the median is reported $C_{max}$, maximum plasma concentration; CV %, percent coefficient of variation; tmax, time to Cmax, $t_{1/2}$, elimination half-life; $AUC_{0-24}$, area under the plasma concentration time curve from 0-24 hours post-dose; $V_{SS}/F$, apparent volume of distribution at steady state; $Cl_{SS}/F$, clearance at steady state In the dose range of 10-100 mg/day, Compound 1 was found to be dose proportional for $C_{max}$ at Day 7 (β=1.17 [95% CI: 0.98-1.37]), and approximately dose proportional for $AUC_{0-24}$ (β=1.30 [95% CI: 1.10-1.50]). The mean $V_{ss}/F$ and mean $CL_{ss}/F$ of Compound 1 at Day 7 did not appear to change substantially with increases in dose.

Study Design: Open-Label Dosing for 28 Days (Part B):

In the open-label study, adult patients (N=16) diagnosed with schizophrenia were admitted to the clinic and completed a washout of their prior antipsychotic medications. After successful washout, subjects were dosed with Compound 1 (75 mg/day) for 28 days. Patients remained in the clinic for the first two weeks of dosing and outpatient for the remaining two weeks of dosing. Safety assessments included incidence of adverse events, clinical laboratory measures, and movement disorder scales (BARS, AIMS and M-SAS). The effect of Compound 1 on the positive and negative syndrome (PANSS) scale and clinical global impression-severity (CGI-S) was also assessed.

A total of 14 subjects completed the 28-day open-label study. Two subjects discontinued the study after two weeks due to multiple mild adverse events. Of the 16 subjects randomized, 50% were male, the mean age was 31.8 (range, 23-40), 75.0% were African-American, and the mean PANSS total score was 73.3.

No exacerbations of schizophrenia symptoms were observed in any subject. There were no clinically significant treatment-emergent changes in laboratory parameters; ECG parameters, including QTcB and QTcF intervals; neurological examinations; or movement disorder effects as measured by the Barnes Akathisia Scale, Abnormal Involuntary Movement Scale, or the modified Simpson-Angus Scale in either Part A or Part B of the study, nor were there any deaths.

The pharmacokinetic parameters following multiple 75 mg/day doses of Compound 1 (Part B, Day 13) were as follows: $C_{max}$ (CV %), 316 ng/mL (17.5%); $t_{max}$ (median), 4.0 hours; $AUC_{0-24}$, 3487 h ng/mL. Visual inspection of mean trough plasma concentrations of Compound 1 showed that steady state was achieved by Day 7.

In addition, treatment with Compound 1 demonstrated improvement in efficacy measures (PANSS total score, CGI-S) compared with baseline. Furthermore, ad hoc subgroup analyses showed a significantly greater decrease from baseline in PANSS total scores at the end of the 28-day treatment period in subjects who had less frequent hospitalizations per year of illness compared with subjects who had more frequent hospitalizations per year of illness.

In summary, no safety issues were observed with multiple oral doses of Compound 1 in doses ranging from 10-100 mg/d for seven days, or in a dose of 75 mg/d for 28 days. There were no clinically significant, treatment-emergent changes in vital signs, physical examination, laboratory parameters, or ECG parameters, including QTcF intervals. No subject had treatment-emergent suicidal ideation or behavior. Treatment with Compound 1 at 75 mg/d for 28 days was associated with improvement in PANSS total score that was greater in patients with high baseline PANSS total scores, lower age, and fewer hospitalizations. Results from this study demonstrate an acceptable safety and tolerability profile of Compound 1 (75 mg/day) up to 28 days in patients with schizophrenia.

Pharmacokinetic (pk) metrics measuring from plasma samples across various populations (e.g., clinical studies) can be pooled to model population pharmacokinetic profiles. For example, pooling pk measurements across nine (9) various populations (e.g., clinical studies) yielded the modeled population pk profiles shown in Table 22.

TABLE 22

Simulated Pharmacokinetic Profiles of 1,000 patients with schizophrenia that were generated from the full model at 25, 50, 75, 100, 125, and 150 mg QD and their geometric means calculated at each time point.

| Parameter | Dose | | | | | |
|---|---|---|---|---|---|---|
| | 25 mg | 50 mg | 75 mg | 100 mg | 125 mg | 150 mg |
| Day 1 | | | | | | |
| $AUC_{last}$, ng/mL*hr | 778 | 1580 | 2410 | 3100 | 4000 | 4690 |
| $C_{trough}$, ng/mL | 7.03 | 14.5 | 22.8 | 27.8 | 37.5 | 42.2 |
| $C_{max}$, ng/mL | 69.9 | 142 | 213 | 280 | 355 | 424 |
| Day 3 | | | | | | |
| $AUC_{last}$, ng/mL*hr | 866 | 1770 | 2700 | 3460 | 4490 | 5230 |
| $C_{trough}$, ng/mL | 7.97 | 16.5 | 26.0 | 31.5 | 42.8 | 47.9 |
| $C_{max}$, ng/mL | 77.7 | 158 | 238 | 312 | 398 | 471 |

$C_{max}$ = maximum serum concentration.
$AUC_{last}$ = area under the concentration-time curve from zero (predose) through the end of observation.
$C_{trough}$ = minimum concentration in the dosing interval.

Example 4: Preparation of (S)-(4,5-dihydro-7H-thieno[2,3-c]pyran-7-yl)-N-methylmethanamine ("(S)-TPMA") HCl of Crystalline Form A (i.e., Crystalline Form A of the HCl Salt of Compound 1) and Formulations Thereof Scheme 1: Preparation of 4,5-dihydro-7H-thieno[2,3-c]pyran-7-yl)-N-methylmethanamine triflate

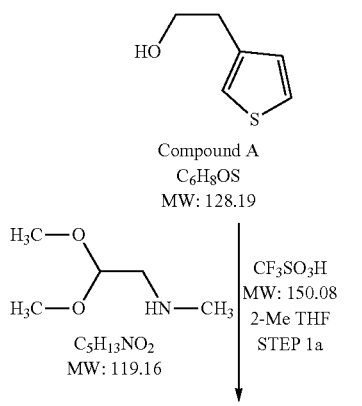

Compound A
$C_6H_8OS$
MW: 128.19

CF$_3$SO$_3$H
MW: 150.08
2-Me THF
STEP 1a $C_5H_{13}NO_2$
MW: 119.16

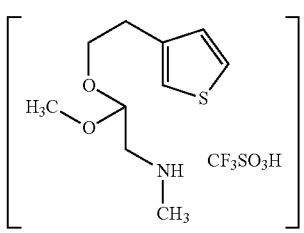

Compound B
$C_{11}H_{18}NO_5F_3S_2$
MW: 365.39

STEP 1b

-continued

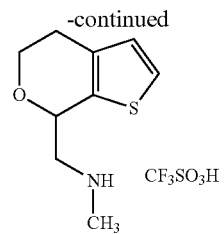

Compound C
$C_{10}H_{14}NO_4F_3S_2$
MW: 335.35

77 g of 3-thiopheneethanol (Compound A) was added to a solution of 69 g of N-methylaminoacetaldehyde dimethyl acetal in 595 ml (508 g) of 2-methyl tetrahydrofuran (THF). After stirring for 5 minutes 99 g (58.2 ml) trifluoromethanesulfonic acid was added. It is important to note that trifluoromethanesulfonic acid is a very hazardous substance. The reaction was heated to reflux for 1 hour (80±2° C.). The reaction was then distilled at atmospheric pressure to remove the byproduct methanol and to reduce the reaction volume to a targeted volume of 460 ml over 4-8 hours. The reaction was judged complete when 1.0% or less (HPLC Peak Area % of peaks of interest, Compounds A, B and C) of compound 1B remained by a sample HPLC analysis.

If the amount of Compound B was greater than or equal to 1%, an appropriate amount of 2-methyl THF was added and distillation continued to the target volume. If the target volume was reached before the completion of reaction (about 4 hours), 300 ml 2-methyl THF was added to the reaction for continuation of the distillation. After reaction completion, the reaction was cooled to about 40-50° C. and concentrated to a target volume of 325 ml under vacuum distillation. 218 g (325 ml) of Toluene was then added over about 15 minutes and the reaction slurry formed was then stirred for 1 hour at 50±2° C., and then cooled to 20±2° C. linearly over 1 hour 45 minutes while being stirred. The slurry was filtered and the product cake was washed with a 2-methyl THF and toluene mixture (1:1 volume/volume). The wet-cake was dried under vacuum at 40±5° C. to constant weight to yield racemic TPMA triflate (Compound C) as an off-white solid and a yield of about 79% was obtained.

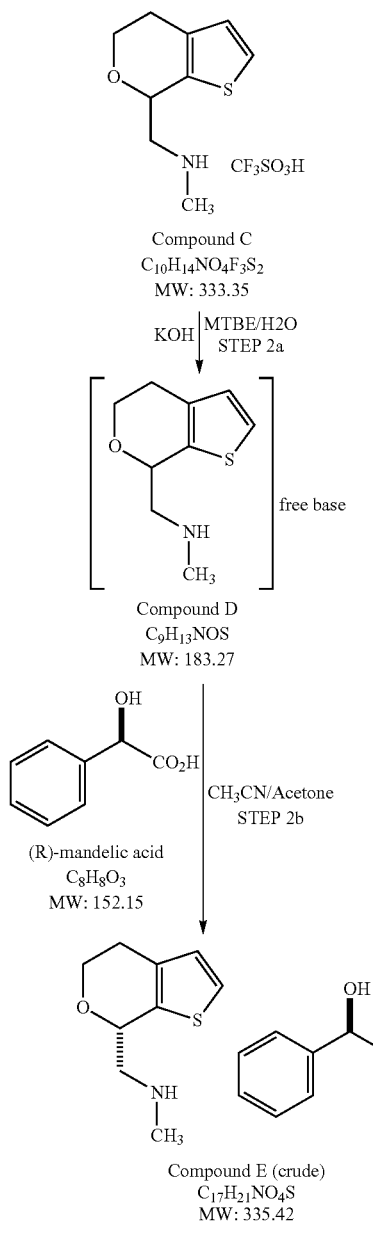

Scheme 2: Preparation of (S) - (-) - 4,5-dihydro-7H-thieno[2,3-c]pyran-7-yl)-N-methylmethanamine (R) mandelate To a suspension of 555.3 g of TPMA triflate (Compound 1C) in 1668 ml methyl tert-butyl ether (MTBE) was added 1076 g of 1.77 N aqueous KOH. After stirring for 10 minutes the pH was checked and if less than 13 small portions of 1.77 N KOH were added until the pH was 13 or greater. The aqueous and organic layers were allowed to settle and separate and separately collected. The MTBE (upper) organic phase layer was held for further processing. The aqueous (bottom) phase layer was extracted twice with MTBE (first with 835 ml and second with 150 ml), the organic (MBTE) layer being collected each time. The MTBE layers (organic layers) were combined, and washed with 20% aqueous NaCl solution (492.9 g) stirred and the phases allowed to settle for 10 minutes. The aqueous layer was removed and the remaining MTBE organic layer was distilled at atmospheric pressure to reduce the reaction volume to a targeted level of 1.9 L. After completion, the process stream was cooled to about 45° C. and concentrated to a target volume of 890 ml under vacuum distillation while maintaining the temperature at 35-45° C. The water content after vacuum distillation was found to be about 0.37% buy weight. A filtration was then performed to remove insoluble materials using a wash of 204 ml MTBE, and the process stream (filtrate) was transferred to a clean reactor. 2512 mL of acetonitrile was added and a solvent switch was performed via vacuum distillation at 35-45° C. to the targeted volume of 800 ml, and the reactor washed with 150 ml of acetonitrile and added to the process stream. The resulting process stream, acetonitrile solution of TPMA free base (Compound D). Acetonitrile was then added, if needed, to the acetonitrile solution of TPMA free base (Compound D) to achieve about a 33 weight % of Compound D.

A solution of 250.3 g of (R)-mandelic acid in 1828 ml of acetone was warmed to 48±2° C. The TPMA free base solution in acetonitrile (917.7 g solution of 302.1 g of Compound D in acetonitrile) was then added at a rate maintaining the reaction temperature below 51° C. After stirring at 48±2° C. for about 10 minutes the process stream was cooled to 45±2° C. and charged with 1.5 g of (S)-TPMA (R)-mandelate seed crystals. The process stream was stirred at 45±2° C. for about 30 minutes and cooled linearly to 21±2° C. over 90 minutes. After holding at 45±2° C. for about 30 minutes the process stream was cooled linearly to 10±2° C. over 45 minutes. The reaction slurry was then stirred for 60 minutes at 10±2° C., filtered and the product cake was washed with acetone/CH$_3$CN mixture (2.3:1 weight/weight). The wet-cake was dried under vacuum at 40±2° C. to a constant weight to yield crude (S)-TPMA (R)-mandelate (Compound E) as a white crystalline solid, and a yield of about 41% was obtained.

Scheme 3: Recrystallization of (S)- 4,5-dihydro-7H-thieno[2,3-c]pyran-7-yl)-N-methylmethanamine (R) mandelate

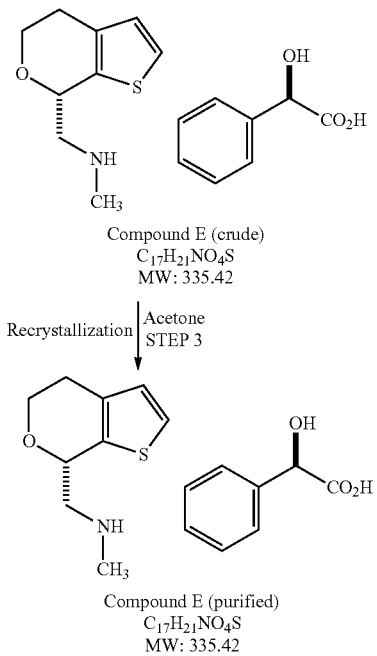

A slurry of crude (S)-TPMA (R)-mandelate (Compound E) from Scheme 2 (200.1 g) in 4205 ml of acetone was warmed to about 56° C. (boiling point of acetone) and stirred until a clear solution was obtained. After cooling the solution to 47±2° C. over approximately 20 minutes (S)-TPMA (R)-mandelate seed crystals were added. The process stream was stirred at 47±2° C. for about 30 minutes and cooled linearly to 21±2° C. over 90 minutes. After holding at 21±2° C. for about 30 minutes the slurry was cooled linearly to 10±2° C. over 45 minutes and then stirred for 1 hour at 10±2° C., filtered, and the product cake was washed with acetone (twice with 401 ml each time). The wet-cake was dried under vacuum at about 40±2° C. to a constant weight to yield (S)-TPMA (R)-mandelate (purified Compound E) as a white crystalline solid, and a yield of about 77% was obtained.

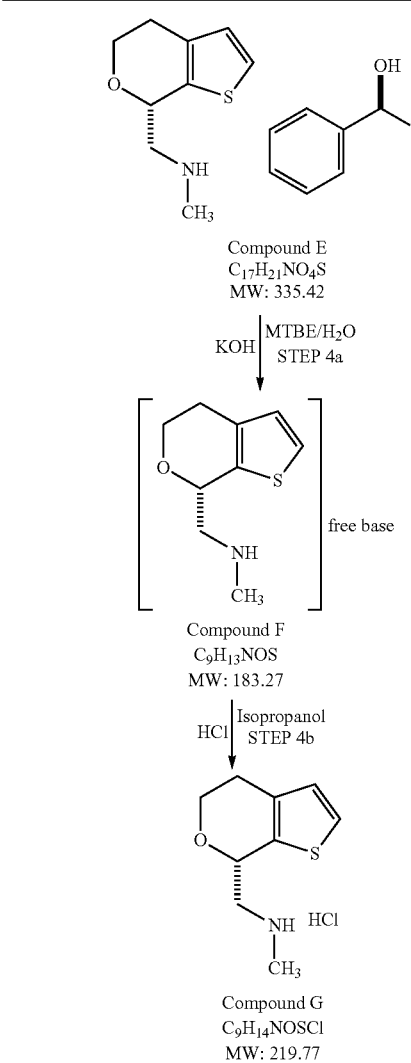

Scheme 4: Formation (S)-(-)- 4,5-dihydro-7H-thieno[2,3-c]pyran-7-yl)-N-methylmethanamine hydrochloride of Crystalline Form A Compound E
C$_{17}$H$_{21}$NO$_4$S
MW: 335.42

KOH | MTBE/H$_2$O STEP 4a free base

Compound F
C$_9$H$_{13}$NOS
MW: 183.27

HCl | Isopropanol STEP 4b

Compound G
C$_9$H$_{14}$NOSCl
MW: 219.77

Scheme 4 of the present example provides a reactive crystallization of (S)-(-)-4,5-dihydro-7H-thieno[2,3-c]pyran-7-yl)-N-methylmethanamine HCl, ((S)-TPMA HCl), as crystalline Form A. As (S)-TPMA HCl crystallizes it displays two distinct morphologies (polymorphs), the first a block like crystal (Form A) and the second a needle like crystal (Form B). Based on single crystal x-ray diffraction studies, described herein, Form A has a monoclinic crystal system while Form B has an orthorhombic crystal system.

To a suspension of (S)-(4,5-dihydro-7H-thieno[2,3-c]pyran-7-yl)-N-methylmethanamine (R)-mandelate salt (Compound E) from Scheme 3 (100 g) in 305 ml of MTBE, 172.5 ml of a 10% KOH aqueous solution was added. After stirring for 10 minutes at 20±2° C. the aqueous and organic layers were separated. The organic MTBE (upper) layer was saved for further processing. If the pH of the aqueous layer was less than 13, small portions of the 19% KOH solution were added to raise the pH to 13. The aqueous (bottom) layer was back extracted twice with MTBE (first with 208 ml MTBE, second with 155 ml MTBE), the organic layer being saved for further processing each time. The saved organic layers were combined, and the combined organic layer was subjected to azeotropic distillation to remove water and distilled at atmospheric pressure to a target volume of 140 ml. The process stream was then filtered, to remove insoluble material (e.g. salt precipitated due to removal of water), and the filtrate transferred to a clean reactor. 775 ml of Isopropanol was added (resulting in a total process stream volume of about 1030 ml) and a solvent switch was performed via vacuum distillation at less than 45° C. to provide a 10%-15% solution of (S)-(4,5-dihydro-7H-thieno[2,3-c]pyran-7-yl)-N-methylmethanamine in isopropanol.

In various embodiments, the amount of isopropanol added was selected so to adjust the freebase (Compound F) weight % concentration to 6-7%. The reaction mixture was cooled to 20±2° C., filtered, the filter washed with 78 ml isopropanol, and the filtrate transferred to a clean reactor. 201.6 g of a 6% HCl (w/w) solution in isopropanol was then added into the reactor over 45 minutes at about 20±2° C. It is to be understood that in various embodiments, the target amount of HCl is about 10% excess relative to the freebase (Compound F) molar equivalence. The HCl was added as follows, the first 10% was added over 15 mins, the next 30% was added over 15 mins, and the remainder was then added over 15 mins. A retreat curve impeller at 160 rpm to 270 rpm in a 5 L scale reactor was used, with a process stream volume of about 740 ml, and produced reasonable-sized particles and particle distributions with no obvious agglomeration observed. The slurry formed was warmed up to 40±2° C. linearly over 20 minutes and held at 40±2° C. for about 30 minutes. It was then cooled linearly to 20±2° C. over 20 minutes. After stirring at 20±2° C. for about 30 minutes the slurry was filtered and the product cake was washed with isopropanol (first with 86 ml, second with 92 ml). The cake was dried under vacuum at 40±2° C. to a constant weight to yield (S)-(-)-TPMA hydrochloride (Compound G) as a white crystalline solid, and a yield of about 84% was obtained.

In Step 4b of Scheme 4, slow addition, that is here, low supersaturation generation rate, favors the formation of desired block (S)-(-)-TPMA HCl crystals (Form A) while decreasing the generation the undesired needles (Form B) and higher temperature favored the formation of the block like Form A crystals over Form B.

An $^1$H NMR spectrum of the (S)-(-)-(4,5-dihydro-7H-thieno[2,3-c]pyran-7-yl)-N-methylmethanamine hydrochloride (Compound G) obtained in this Example 4 has the following characteristics: $^1$H NMR (300 MHz, DMSO-d$_6$); δ (ppm): 2.53 (s, 3H, —CH$_3$); 2.5-2.8 (m, 2H, —CH$_2$—); 3.15-3.37 (dd, 2H, CH$_2$—NH); 3.77 and 4.13 (2ddd, 2H, CH$_2$—O); 5.19 (dd, 1H, O—CH—C=); 6.95 (d, J=5 Hz, 1H, HC=); 7.49 (dd, J=5 Hz, 1H, HC=); 9.12 (br, 2H, NH$_2^+$).

Figure 21:
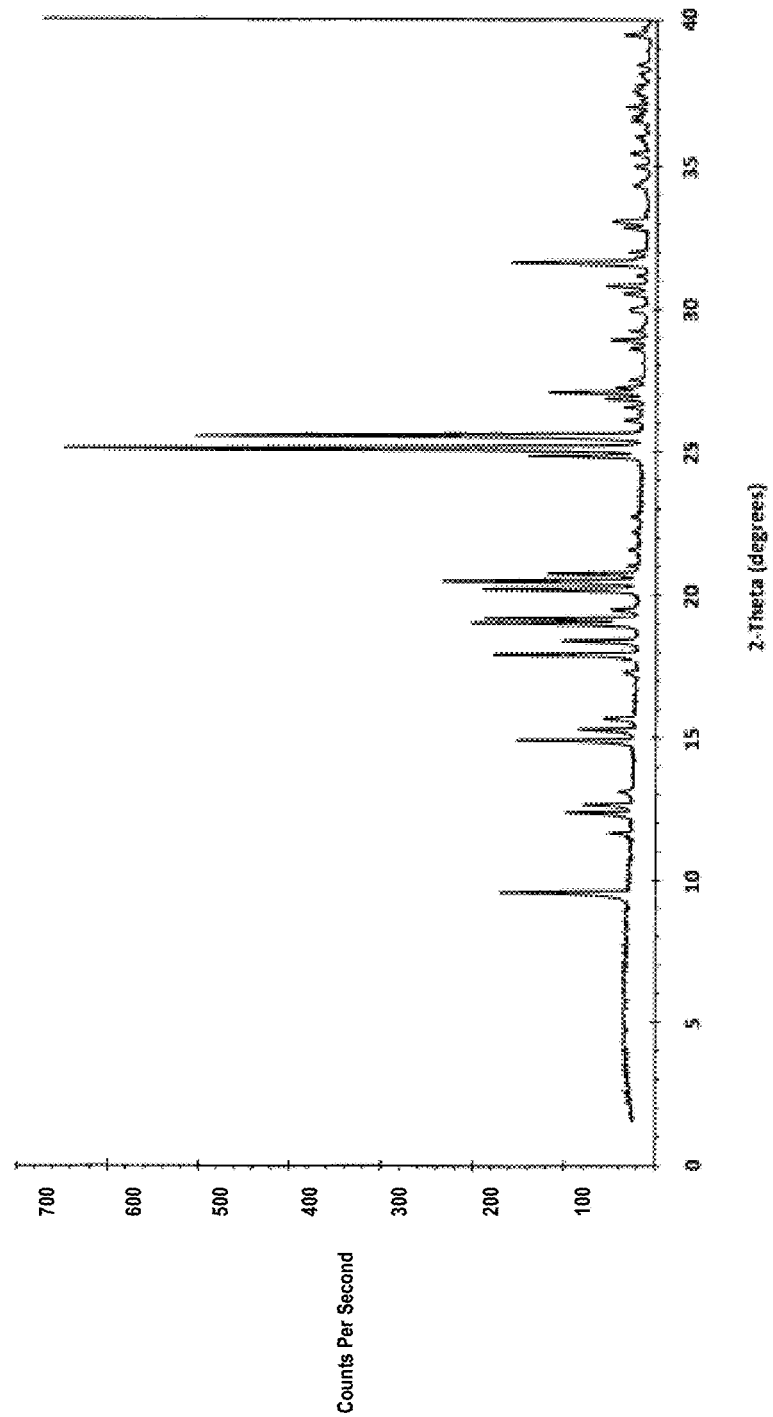
FIG. 21 and FIG. 22 present XRPD patterns for Compound 1 hydrochloride of crystalline Form A.
Figure 22:
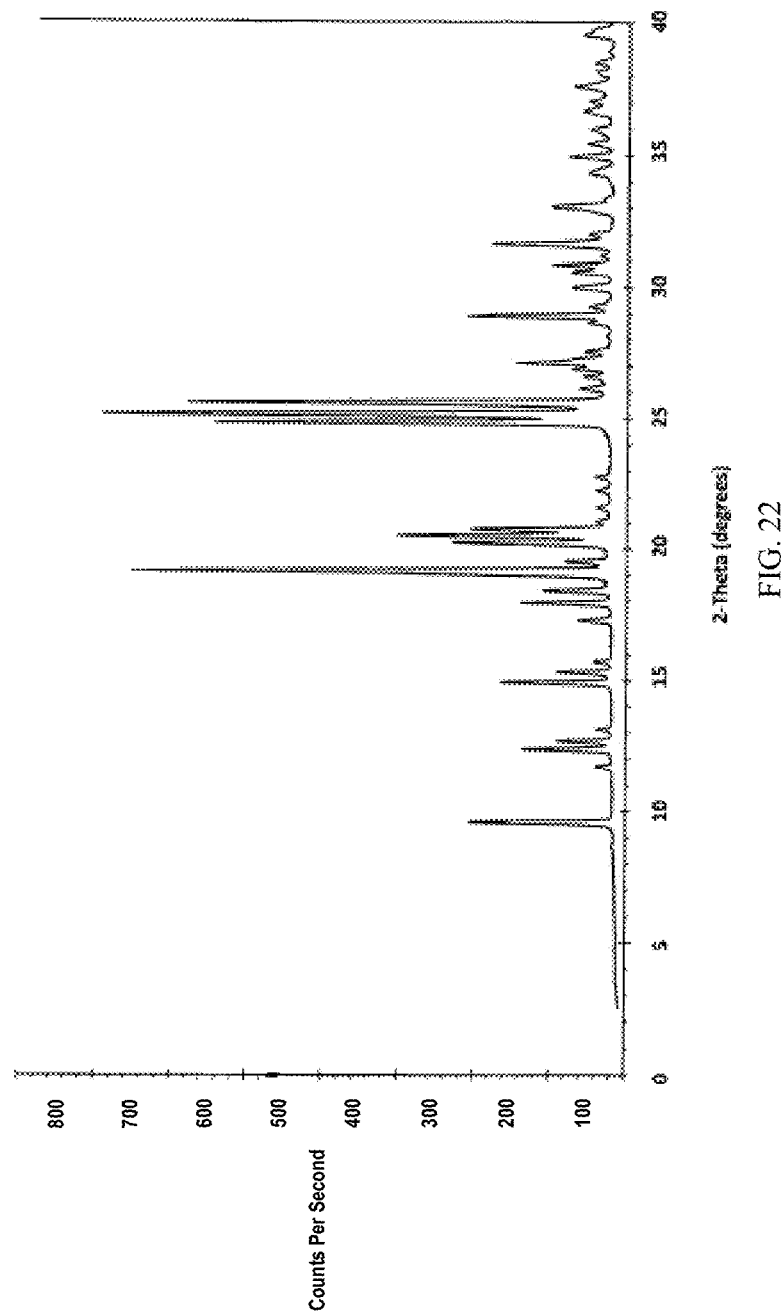
Figure 23:
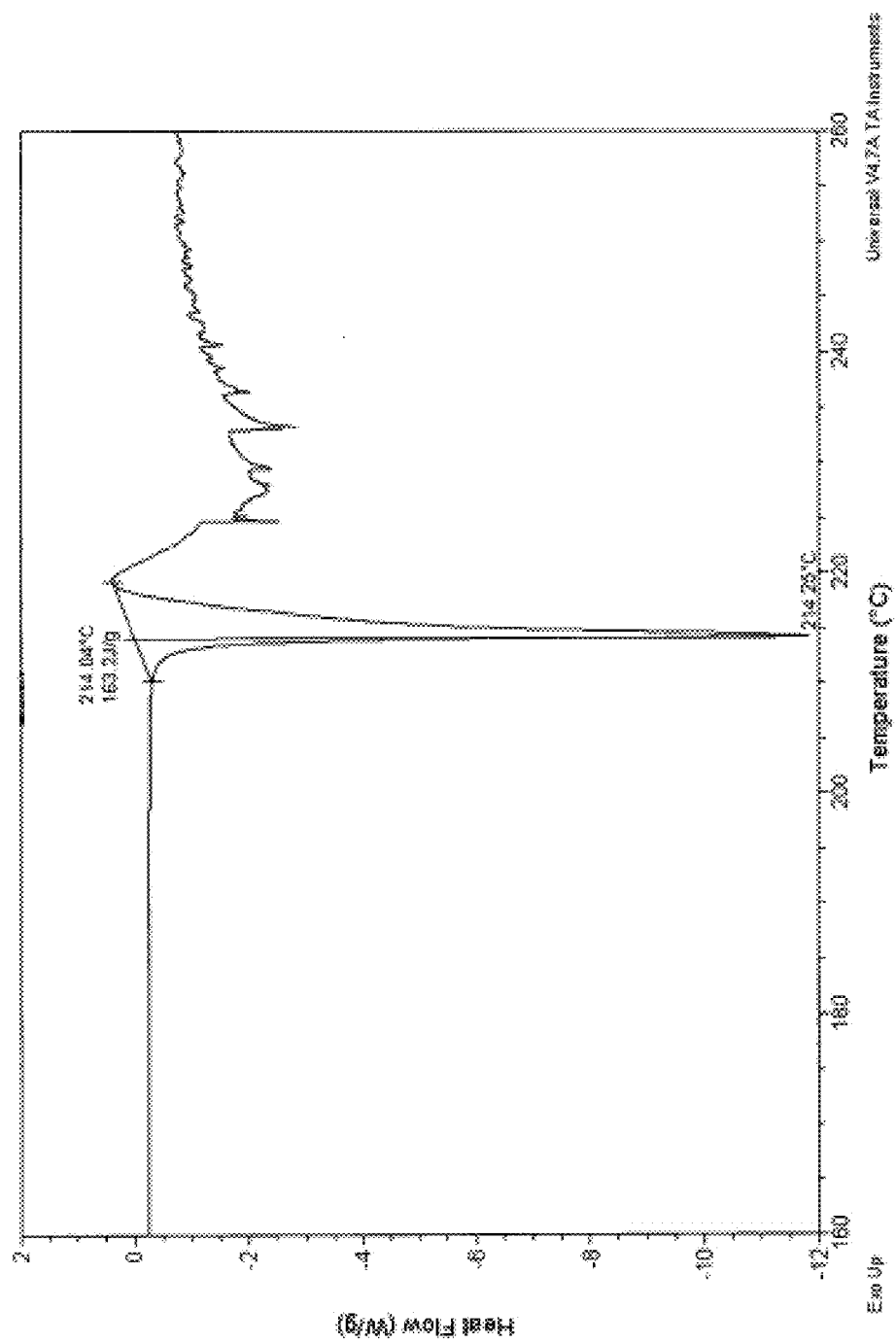
FIG. 23 is a DSC thermogram for Compound 1 hydrochloride of crystalline Form A.

FIGS. 21 and 22 present XRPD patterns for (S)-(4,5-dihydro-7H-thieno[2,3-c]pyran-7-yl)-N-methylmethanamine hydrochloride of Form A; FIG. 21 is the XRPD measured in transmission mode and FIG. 22 in reflection mode. FIG. 23 is a DSC thermogram for (S)-(4,5-dihydro-7H-thieno[2,3-c]pyran-7-yl)-N-methylmethanamine hydrochloride, of polymorph Form A.

Formulations and Manufacture

Formulations comprising Compound 1, or a pharmaceutically acceptable salt thereof, and at least one pharmaceutically acceptable excipient are disclosed in, e.g., PCT Patent Publication No. WO2019/161238, which is incorporated herein by reference in entirety and for all purposes, or a method analogous thereto.

In some embodiments, provided are pharmaceutical compositions comprising Compound 1, or a pharmaceutically acceptable salt thereof, and at least one pharmaceutically acceptable excipient. In some embodiments, provided are pharmaceutical compositions substantially similar to the formulations described in Table 23 and Table 24.

TABLE 23

| Common Blend Formulation | | |
|---|---|---|
| Ingredient | Function | % W/W |
| Common Granulation Composition | | |
| Compound 1, HCl | API | 70.00 |
| Microcrystalline Cellulose | Filler | 27.80 |
| Sodium Starch Glycolate | Disintegrant | 2.00 |
| Magnesium Stearate | Lubricant | 0.20 |
| Total | | 100.0 |
| Common Compression Blend Composition | | |
| Compound 1, HCl Granules | API | 42.87 |
| Microcrystalline Cellulose | Filler | 45.80 |
| Mannitol | Filler | 8.83 |
| Sodium Starch Glycolate | Disintegrant | 2.00 |
| Magnesium Stearate | Lubricant | 0.50 |
| Total | | 100.0 |

TABLE 24

| Tablet Compositions Using Common Blend Formulation for Compression Formulation | | | | | | |
|---|---|---|---|---|---|---|
| Dose Strength (mg) | | 12.5 mg | 25 mg | 50 mg | 75 mg | 100 mg |
| Ingredient | Function | % W/W | | | | |
| Compound 1, HCl | API | 30.00 | | | | |
| Microcrystalline Cellulose | Filler | 57.72 | | | | |
| Mannitol | Filler | 8.83 | | | | |
| Sodium Starch Glycolate | Disintegrant | 2.86 | | | | |
| Magnesium Stearate | Lubricant | 0.59 | | | | |
| Total (mg/tablet) | | 50.0 | 100.0 | 200.0 | 300.0 | 400.0 |
| Coating, mg/tablet (% W/W) | | | | | | |
| Core Tablet | | 50.0 (96.15) | 100.0 (96.15) | 200.0 (97.09) | 300.0 (97.09) | 400.0 (97.09) |
| Opadry 20A120006 Yellow, Opadry 20A18407 White, Opadry 20A820002 Yellow, or Opadry 20A110008 Green (HPMC/HPC) | Polymer Coating System | 2.0 (3.85) | 4.0 (3.85) | 6.0 (2.91) | 9.0 (2.91) | 12.0 (2.91) |
| Carnauba wax | Polishing agent | 0.002 (0.00385) | 0.004 (0.00385) | 0.008 (0.00388) | 0.012 (0.00388) | 0.016 (0.00388) |
| Total | | 52.0 (100) | 104.0 (100) | 206.0 (100) | 309.0 (100) | 412.0 (100) |

Example 5: Preclinical Abuse Liability Assessment of Compound 1

Compound 1 is a psychotropic agent with a unique, non-D2, non-5-HT$_{2A}$ mechanism of action (MOA) which has shown broad efficacy across multiple animal models relating to aspects of schizophrenia. The molecular targets responsible for the antipsychotic efficacy of Compound 1 are not fully elucidated but include agonism of trace amine associated receptor-1 (TAAR1) and 5HT$_{1A}$ receptors. Based on its unique MOA and profile in animal models, Compound 1 represents a promising candidate for the treatment of schizophrenia and potentially other neuropsychiatric disorders. See, e.g, Koblan et al. THE NEW ENGLAND JOURNAL OF MEDICINE 382(16), 1497-1506 (2020); Dedic et al. THE JOURNAL OF PHARMACOLOGY AND EXPERIMENTAL THERAPEUTICS 371, 1-14 (2019). Given the central nervous system activity of Compound 1, a series of nonclinical studies were undertaken with Compound 1 to evaluate potential risk for abuse. The United States Food and Drug Administration (FDA) provides a guidance document for assessing abuse potential of drugs: "Assessment of Abuse Potential of Drugs. Guidance for Industry. January 2017" which is incorporated herein in its entirety. A series of abuse-related animal behavioral studies (self-administration and drug discrimination) were conducted in male and female rats to evaluate whether Compound 1 produces behavioral changes suggestive of human abuse potential. In addition, studies were undertaken to probe the potential for Compound 1 to block reinstatement of cocaine-seeking behavior in male rats.

Experimentally naïve rats were housed individually in plastic cages containing bedding. Housing rooms were maintained under a 12/12-hour light/dark cycle at controlled ambient temperature and relative humidity. Animals were allowed to acclimate to laboratory conditions before the beginning of experiments and had free access to water. Access to food was restricted to facilitate training and maintenance of operant behavior with the exception of training of female rats in the MDMA drug discrimination study. Experiments were conducted in operant chambers (MED Associates, Inc., St. Albans, Vt., U.S.A.) located within sound-attenuating, ventilated cubicles. Each chamber was equipped with a stimulus light, lever(s) located near a food receptacle which was connected to a food pellet dispenser. Chambers used for reinstatement studies were also equipped with a Sonalert® tone generator.

Self-Administration Studies: Following successful completion of operant training and recovery from intravenous (i.v.) catheterization surgery, self-administration training sessions were conducted (0.5 mg/kg/infusion cocaine under an FR10 schedule, 0.07 mg/kg/infusion amphetamine under an FR5 schedule, or 0.015 mg/kg/infusion heroin under an FR3 schedule). After training drug responding stabilized, saline was substituted until self-administration was extinguished. Ascending i.v. doses of Compound 1, selected based on assessment of effects of Compound 1 on operant behavior, were substituted for training drug for at least 5 consecutive test sessions. Intermittent re-testing with the training drug (0.25 mg/kg/infusion cocaine, 0.07 mg/kg/infusion amphetamine, 0.015 mg/kg/infusion heroin) was conducted to ensure maintenance of self-administration behavior. Mean numbers of infusions over the last three sessions of stable responding (or the mean of 10 sessions if there was no stable response) were calculated for each animal.

Figure 24A:
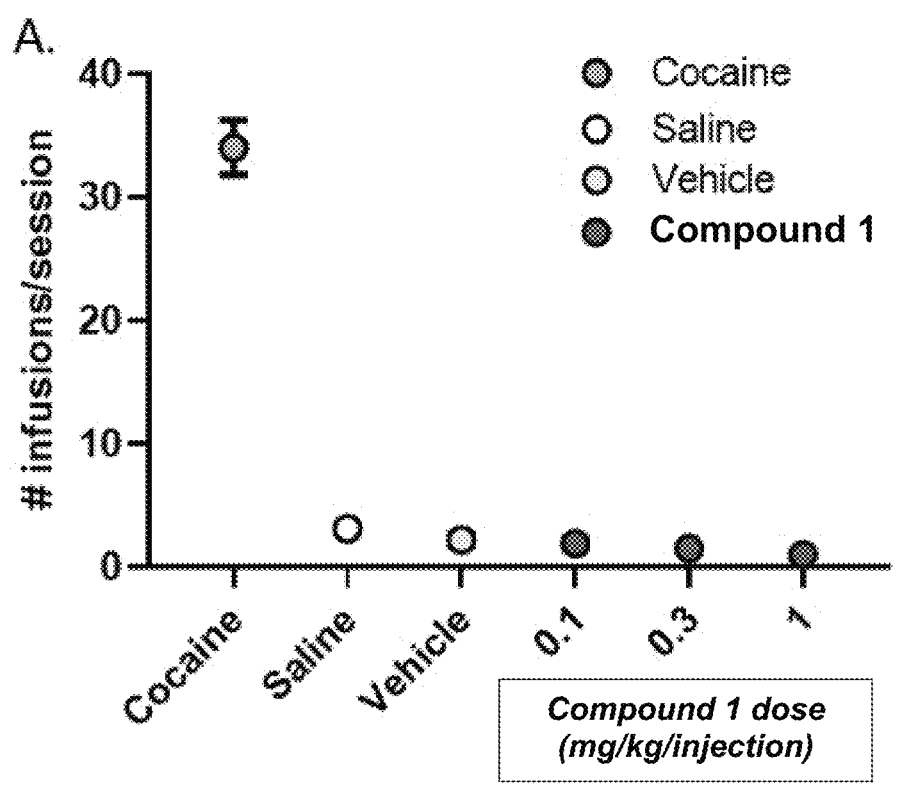
FIG. 24A shows the mean (±SEM) number of infusions in the self-administration (cocaine substitution) test of Example 5.
Figure 24B:
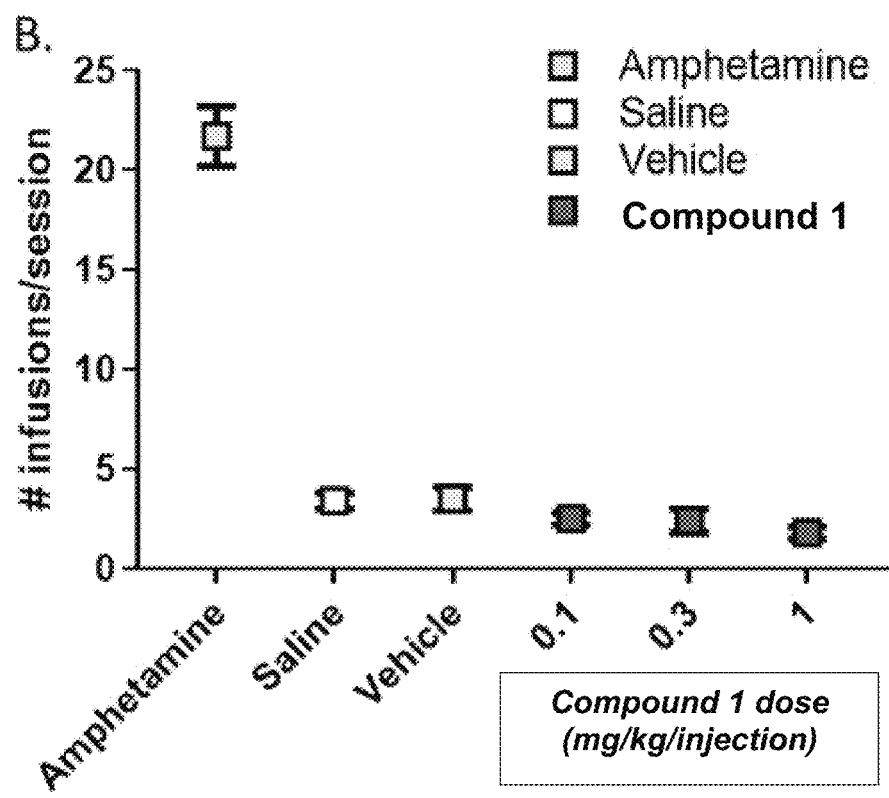
FIG. 24B shows the mean (±SEM) number of infusions in the self-administration (amphetamine substitution) test of Example 5.
Figure 24C:
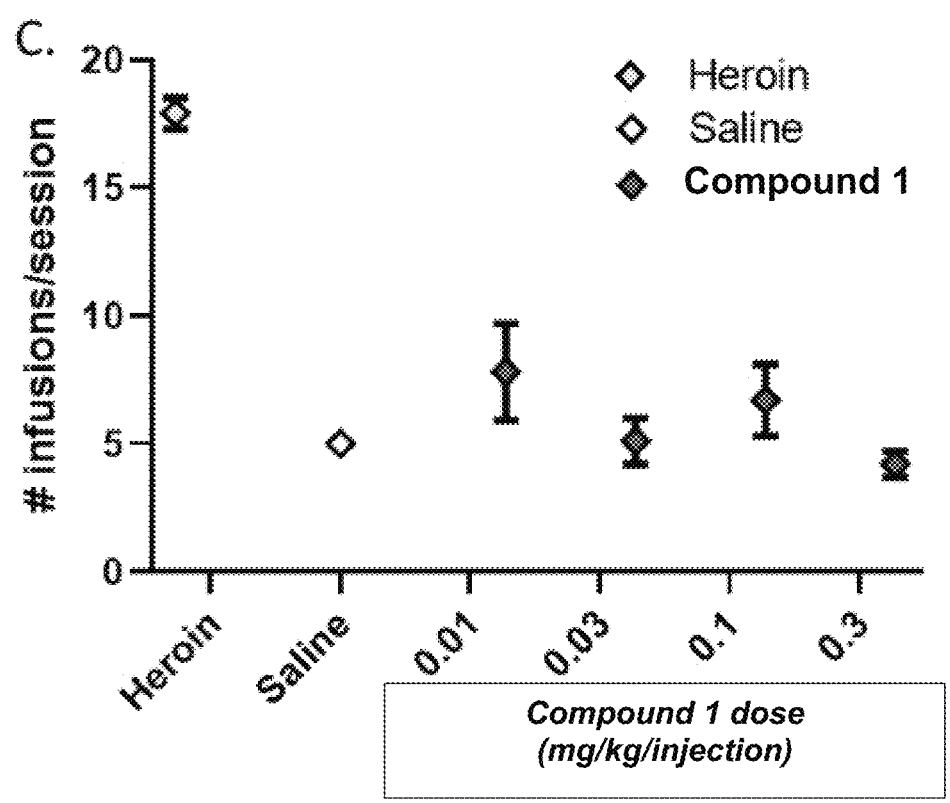
FIG. 24C shows the mean (±SEM) number of infusions in the self-administration (heroin substitution) test of Example 5.

FIG. 24A, FIG. 24B, and FIG. 24C show that Compound 1 was not self-administered by rats trained to self-administer cocaine, amphetamine or heroin, respectively. The mean (±SEM) number of infusions in a self-administration (cocaine substitution) test in male SD rats (n=10) was 1.9±0.4, 1.5±0.3 and 1.0±0.3 per session at Compound 1 dose levels of 0.1, 0.3 and 1 mg/kg/infusion, respectively. The mean number of infusions at each Compound 1 dose level was significantly lower than the preceding cocaine session mean (range 32.7±2.1 to 33.4±2.7; p<0.001 by Tukey's multiple comparison test) and not significantly different from vehicle (2.2±0.5) or saline (3.1±0.3) controls.

The mean (±SEM) number of infusions in a self-administration (amphetamine substitution) test in male SD rats (n=12) was 2.5±0.3, 2.4±0.6 and 1.8±0.3 per session at Compound 1 dose levels of 0.1, 0.3 and 1 mg/kg/infusion, respectively. The mean number of infusions at each Compound 1 dose level was significantly lower than the preceding amphetamine session mean (range 18.5±0.5 to 19.4±0.6; p<0.001 by Tukey's multiple comparison test) and not significantly different from vehicle (3.5±0.6) or saline (3.4±0.4) controls.

The mean (±SEM) number of infusions in a self-administration (heroin substitution) test in male SD rats (n=8-9/session) was 8.0±2.5, 5.4±0.9, 6.4±1.4, and 4.4±0.5 at Compound 1 dose levels of 0.01, 0.03, 0.1, and 0.3 mg/kg/injection, respectively. The statistically-adjusted mean number of infusions at each Compound 1 dose level was significantly lower than the heroin acquisition session mean (19.0±0.4, p<0.001 by Dunnett's test) and was not significantly different from the saline extinction session mean (4.8±0.2).

Drug Discrimination: Following successful completion of operant training, separate groups of rats were trained to discriminate between a training drug (0.6 mg/kg amphetamine i.p. or 1.25 mg/kg 3,4-methylenedioxymethamphetamine (MDMA) i.p.) and saline in 2-choice lever-pressing tests using food reinforcement (FR10 for amphetamine, FR5 for MDMA). The training substance was administered 15 minutes before the session. When each animal achieved discrimination training criteria, Compound 1 or buspirone doses were orally administered prior to test sessions. The percentage of total responses on the training drug-appropriate lever and response rates were calculated for each rat.

Figure 25A:
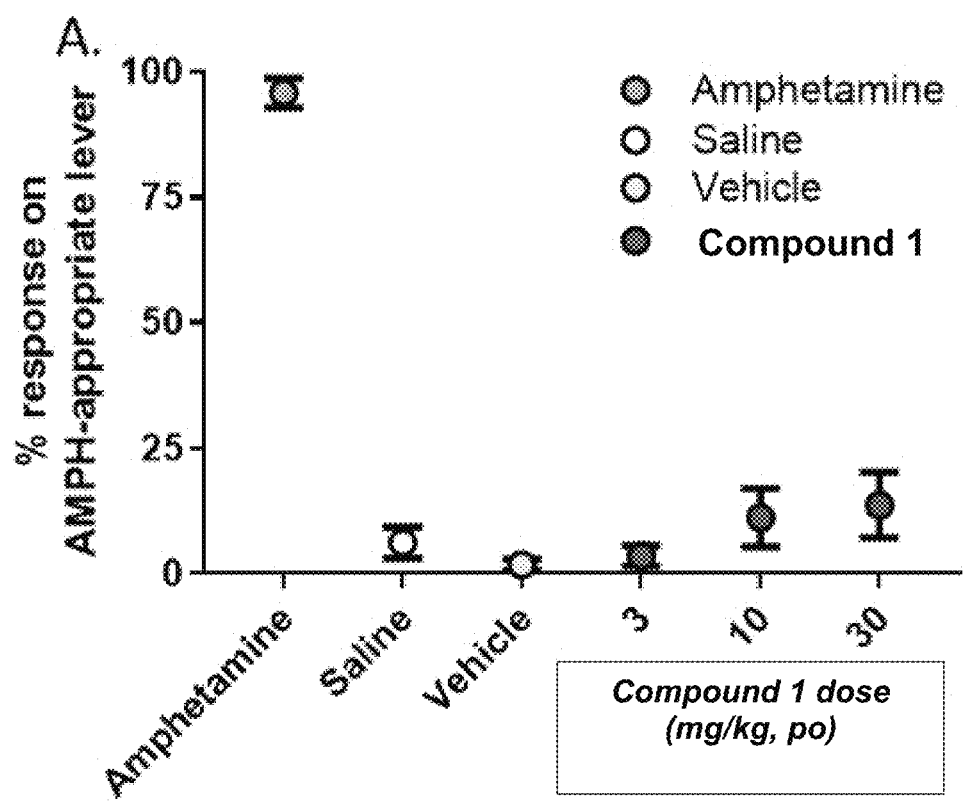
FIG. 25A shows the mean (±SEM) amphetamine-appropriate lever response percentage to Compound 1 in the drug discrimination study of Example 5 (po=per os).
Figure 25B:
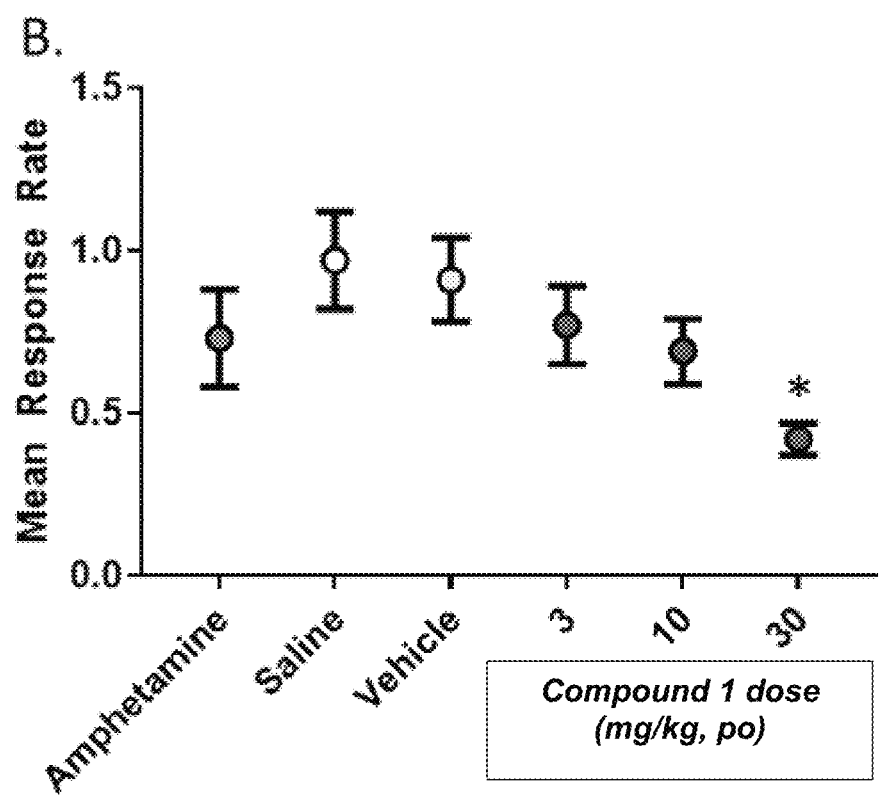
FIG. 25B shows the mean (±SEM) response rate to Compound 1 in the drug discrimination study of Example 5.

FIG. 25A and FIG. 25B show that Compound 1 did not generalize to amphetamine cue in rats. Mean (±SEM) amphetamine-appropriate lever responses of 3.5% (±2.0%), 11.2% (±5.8%) and 13.7% (±6.6%) were observed at 3, 10, and 30 mg/kg Compound 1, respectively, in male SD rats (n=10). Mean (±SEM) response rate (response/s) was not affected at 3 or 10 mg/kg Compound 1 (0.77±0.12 or 0.69±0.10, respectively, versus 0.91±0.13 responses/s with vehicle, p>0.05). At 30 mg/kg, Compound 1 significantly decreased the response rate (0.42±0.05, *p<0.001 by Tukey's multiple comparison test).

Figure 26A:
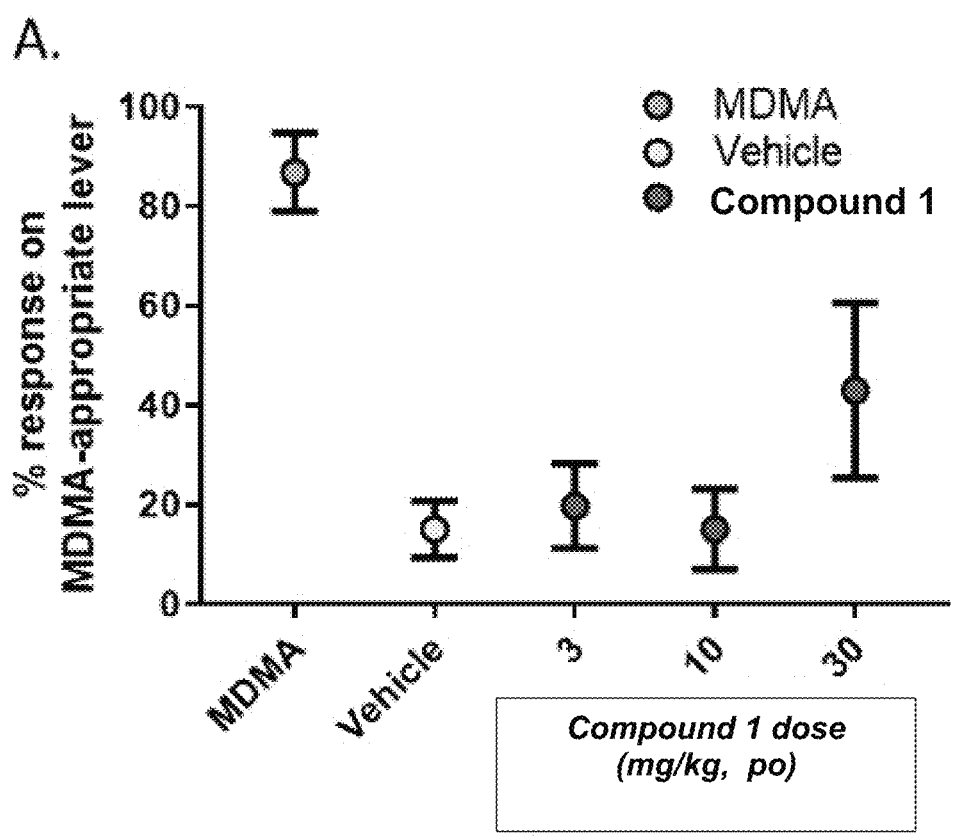
FIG. 26A shows the mean (±SEM) MDMA-appropriate lever response percentage to Compound 1 in the drug discrimination study of Example 5.
Figure 26B:
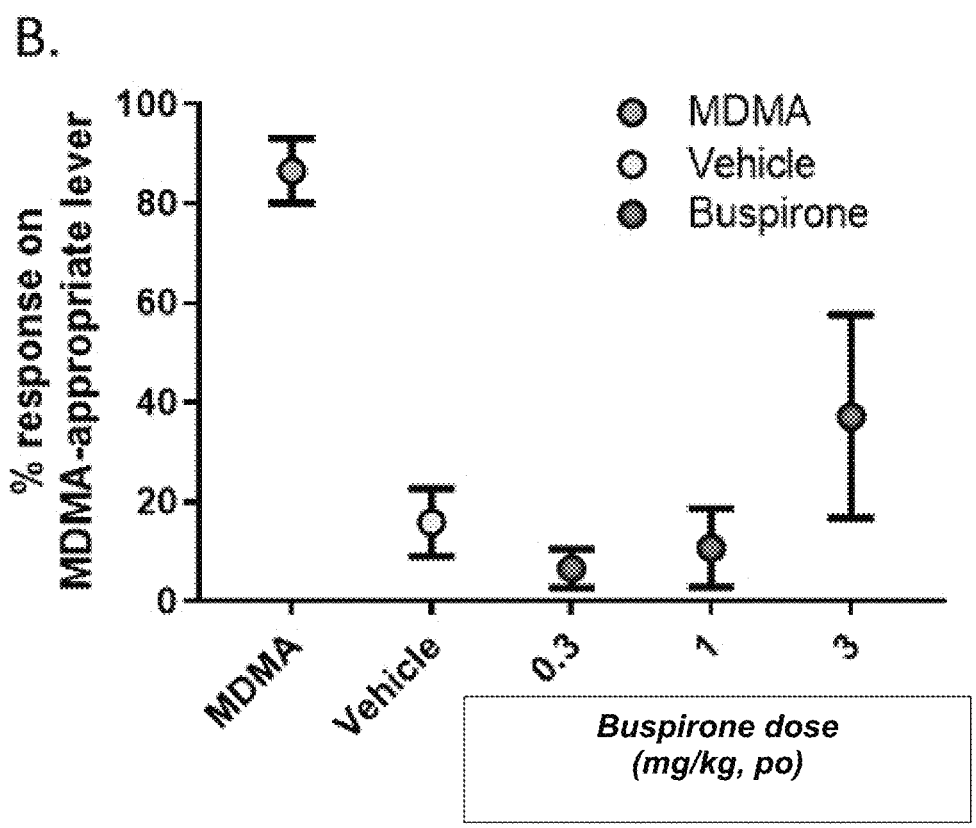
FIG. 26B shows the mean (±SEM) amphetamine-appropriate lever response percentage to buspirone in the drug discrimination study of Example 5.

FIG. 26A and FIG. 26B show that Compound 1 partially generalized to the i.p. MDMA cue in rats. In female Lister hooded rats (n=6-7/dose), Compound 1, at 3 or 10 mg/kg, did not generalize to the MDMA cue (19.8±8.5% and 15.1±8.1% generalization to MDMA, respectively). At 30 mg/kg, Compound 1 partially generalized to the MDMA cue (43.0±17.6% generalization). None of the Compound 1 doses resulted in unacceptable suppression of lever pressing. In female Lister hooded rats (n=6/dose), buspirone, at 0.3 or 1 mg/kg, did not generalize to the MDMA cue (6.6±3.9% or 10.8±7.9% generalization to MDMA, respectively). At the highest dose, buspirone partially generalized to the MDMA cue (37.2±20.4% generalization). None of the buspirone doses resulted in unacceptable suppression of lever pressing.

MDMA and 5-HT$_{2A}$ agonist hallucinogens generalize fully to the MDMA discriminative cue. There is a 5-HT$_{1A}$-mediated component to MDMA's discriminative cue because buspirone, a 5-HT$_{1A}$ partial agonist that is an approved, non-scheduled, anxiolytic drug, partially generalized to the MDMA cue. Similar to buspirone, Compound 1 partially generalized to the MDMA cue. Like buspirone, Compound 1 partially generalized to the MDMA cue. The result indicates that Compound 1 does not produce MDMA-like or 5-HT$_{2A}$ agonist-like psychoactive effects. Although not wishing to be bound by any particular theory, the partial generalization observed with the highest dose of Compound 1 most likely derives from its 5-HT$_{1A}$ agonist properties.

Cocaine Reinstatement: After recovery from i.v. catheterization surgery, rats were trained to self-administer cocaine (0.5 mg/kg/infusion) under an FR1, during which each active lever press resulted in infusion delivery as well as a Sonalert® tone sounding, flashing stimulus lights, and extinguishing of the house light for the duration of the infusion. Following successful cocaine self-administration training, extinction sessions were conducted under "prime" or "cue" conditions. During "prime" extinction sessions, cocaine infusions were not delivered; other conditions during extinction were identical to those during self-administration. During "cue" extinction sessions, the house light was illuminated, and the levers were extended but infusions were not administered nor did any other scheduled stimulus change occur. Conditions during reinstatement testing were identical to those during extinction except that an oral dose of Compound 1 (1-10 mg/kg) or its vehicle was administered 60 minutes pre-session and (a) 17 mg/kg i.p. cocaine was administered 10 minutes pre-session ("prime"); or (b) cocaine self-administered infusions did not occur, and cues previously associated with cocaine infusion were presented non-contingently for 6 seconds at the start of the reinstatement test session ("cue") and following each right-side lever press. Mean numbers of active lever presses during reinstatement test sessions were calculated for each animal.

Figure 27A:
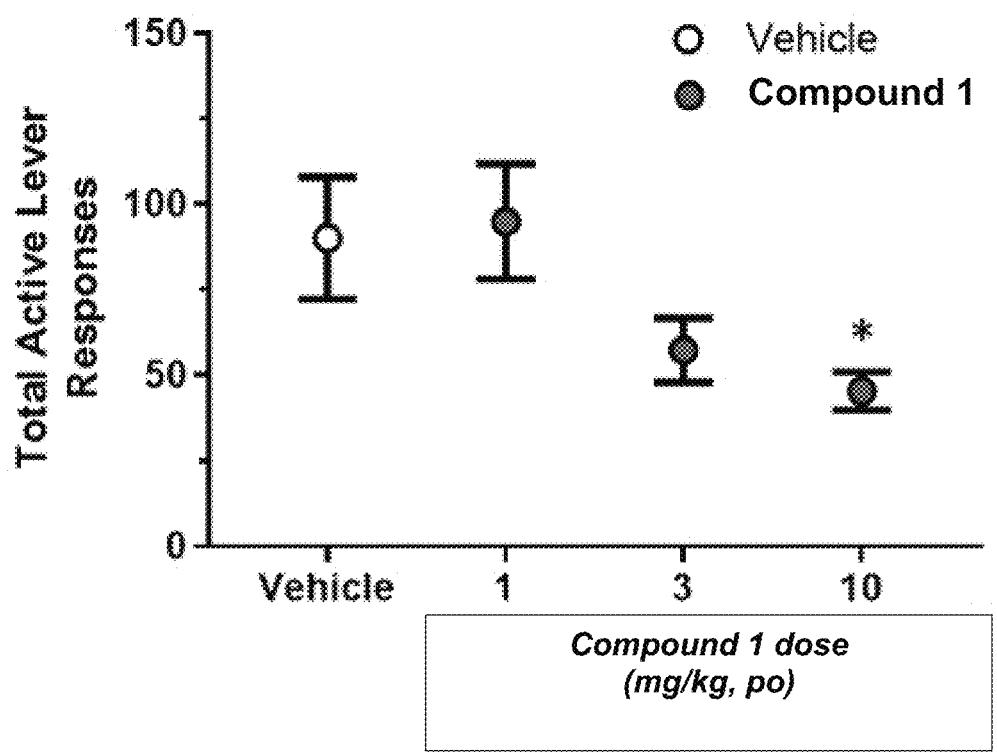
FIG. 27A shows the mean (±SEM) numbers of active lever presses during cue-induced reinstatement test sessions in the cocaine reinstatement study of Example 5.
Figure 27B:
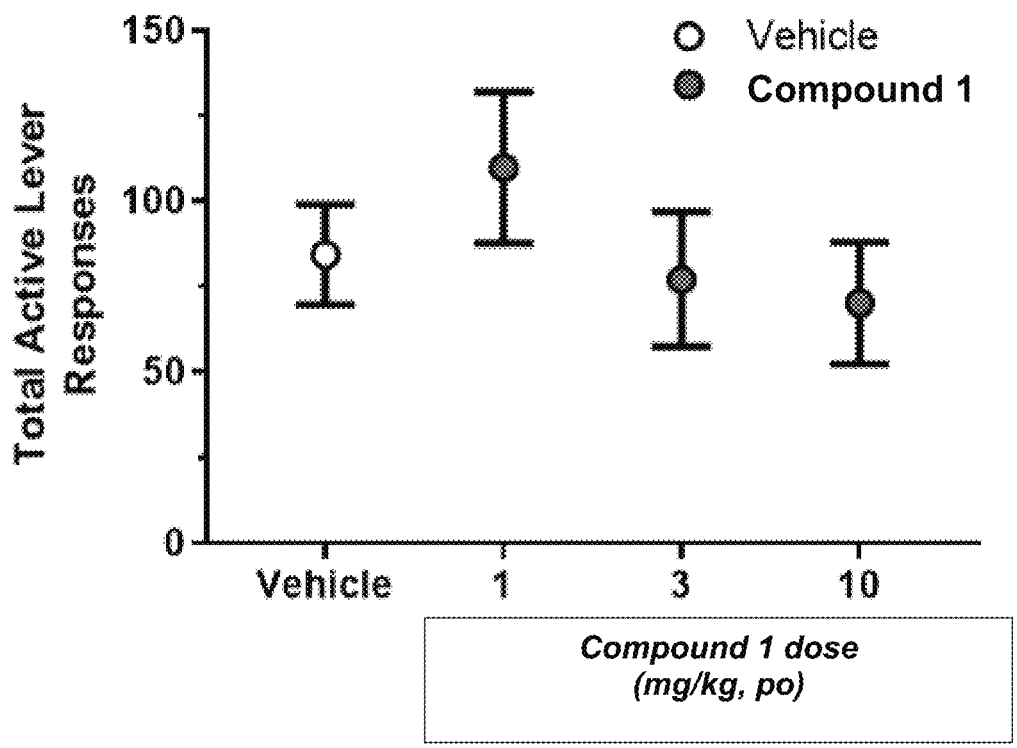
FIG. 27B shows the mean (±SEM) numbers of active lever presses during cocaine prime-induced reinstatement test sessions in the cocaine reinstatement study of Example 5.

FIG. 27A and FIG. 27B show that Compound 1 attenuated cue-induced reinstatement of responding in rats trained to self-administer cocaine (0.5 mg/kg/infusion). Compound 1 (10 mg/kg) significantly reduced cue-reinstated responding in male Long-Evans hooded rats (n=11-12/group). Mean (±SEM) numbers of active lever presses during cue-induced reinstatement test sessions were 90.08±17.86, 94.92±16.83, 57.27±9.36, and 45.36±5.55 for vehicle, 1, 3, or 10 mg/kg Compound 1, respectively (*p<0.05 by uncorrected Fisher's LSD test). Compound 1 (1, 3 or 10 mg/kg) did not significantly reduce cocaine prime-reinstated responding in male Long-Evans hooded rats (n=11-12/group). Mean (±SEM) numbers of active lever presses during cocaine prime-induced reinstatement test sessions were 84.38±14.65, 109.82±22.16, 77.08 19.70, and 70.17±17.78 for vehicle, 1, 3, or 10 mg/kg Compound 1, respectively.

Rats trained to self-administer amphetamine or cocaine did not self-administer Compound 1. Similarly, Compound 1 was not positively reinforcing in rats trained to self-administer a low dose of heroin. Based on the established predictive validity of self-administration procedures in rodents, these results suggest the absence of reinforcing effects of Compound 1 in humans. Over the behaviorally-active dose range of 3 to 30 mg/kg, Compound 1 did not demonstrate similar subjective qualities to amphetamine in rats trained on an amphetamine cue in a drug discrimination procedure. Compound 1 and buspirone, a non-scheduled anxiolytic with 5-HT$_{1A}$ partial agonist activity, demonstrated weak (<50%) partial generalization to the cue elicited by MDMA. Collectively, these results suggest that Compound 1 is not likely to pose a risk for recreational abuse in humans. Further, the reinstatement study results suggest potential therapeutic utility of Compound 1 in the treatment of substance use disorders.

Physical Dependence:

An evaluation of the potential of Compound 1 to produce withdrawal-induced physical dependence was conducted.

Animals

Female Sprague Dawley Rats.
10 rats per group in the main study
12 (+1 spare/group) rats per group for the PK phase
Test Article(s)

Negative Control: Vehicle: 100 mM acetate buffer (pH 5.5) in deionized water; 5 mL/kg
Positive Control: Diazepam 10/15/20 mg/kg p.o. b.i.d. on Days 1-5/6-18/19-46, respectively
Test Item: Compound 1; 3/10 mg/kg p.o. b.i.d.

Rats were dosed with vehicle orally once daily (q.d.), to familiarize them with dosing during the baseline phase (Day −6 to Day 0), and twice daily (b.i.d.) with vehicle, Compound 1, or diazepam on Day 1 to Day 46 using the dose volume (5 ml/kg/administration) based on body weight. Animals were not dosed during the withdrawal phase. Dosing in the morning was staggered such that every animal was observed individually on each day.

Baseline phase: 7 days vehicle Day −6 to Day 0
Drug dosing phase: 46 days Day 1 to Day 46
Withdrawal phase: 7 days Day 47 to Day 53
Termination: 8th day of drug withdrawal (Day 54)

Body weights were recorded prior to each dosing session on Day −6 to Day 46 and in the morning during the withdrawal phase. Only body weight recorded prior to the morning dosing session was used for statistical analysis. Food and water intake were measured once daily in the morning from Day −6 to Day 46 just prior to dosing, and in the morning of the withdrawal phase. Body temperatures were measured once daily using a rectal probe from Day −6 to Day 46 just prior to dosing, and, immediately prior to body weight measurement during the withdrawal. A detailed observation checklist was used to record any physical or behavioral signs of pharmacological effect during dosing and of drug dependence in the withdrawal phase. Rats were observed on a workbench in their open topped home cages (in the holding room where they were kept throughout the study) for a 2 min period 1 hr after the morning dose during the baseline and dosing phases and twice daily on Day 46 and during the withdrawal phase. For the purposes of data interpretation, withdrawal is defined as beginning on Day 46 pm observation for physical and behavioral signs since this observation occurred 5 hr after the final dose of diazepam or Compound 1. For all other endpoints, withdrawal begins on Day 47.

Three groups of thirteen rats (twelve rats for blood sampling and one spare) were dosed with vehicle or Compound 1 (3 and 10 mg/kg p.o., b.i.d.) on Day 1 to Day 46 to mirror the dose regimen for rats in the main phase. Blood samples were collected on Day 1, Day 23 and Day 46 (n=3 rats per time-point) at the following time points: Pre-dose, 30 min, 1 hr, 2 hr, 4 hr, 7 hr, 7.5 hr, 8 hr, 9 hr, 11 hr and 24 hr. Dose formulation analysis was conducted.

Results: Rats in the vehicle-treated control group displayed few behavioral and physical signs, generally with low incidence (2-3 rats), during the baseline, on-dose and withdrawal phase. During the baseline phase, these were limited to rearing, increased reaction to sound (response to finger click) and increased irritability on dosing/gentle restraint. During the on-dose phase, rearing, escape attempts from the cage, increased locomotor activity, increased reaction to sound, piloerection and stained fur were observed. Only rearing was seen with moderate incidence (Days 4, 5 and 9; 4 rats). When administration of vehicle was abruptly terminated, only an increase in increased reaction to sound was observed, and with low incidence relative to Days 42-46 am of the on-dose period. Behaviors during the withdrawal period were limited to escape attempts from the cage, increased locomotor activity, increased reaction to sound and stained fur, again with low incidence with the exception of increased locomotor activity (Day 49 am; 4 rats).

Compound 1 (3 mg/kg/day p.o., b.i.d.) had no effect on body weight, food intake, water intake and body temperature during the dosing phase when expressed on a daily basis, weekly and overall during the dosing phase and daily change during the withdrawal phase. Cessation of Compound 1 (3 mg/kg p.o. b.i.d.) administration was associated with an isolated, but significant, increase in daily food intake compared to vehicle on Day 4 of withdrawal (Day 50); however, no significant change was noted when the data were analyzed as daily change in food intake during withdrawal (difference from mean of Days 42 to 46). Significant increases in daily water intake compared to vehicle were observed on Days 1 to 5 of withdrawal (Days 47-51). This was reflected in a significant increase in daily change in water intake on Days 4 and 5 of withdrawal (Days 50 and 51) relative to Days 42-46 of dosing. Withdrawal from Compound 1 (3 mg/kg p.o. b.i.d.) had no significant effect on body weight or body temperature. Compound 1 (3 mg/kg p.o. b.i.d.) produced, with low to moderate incidence, rearing, increased body tone, increased locomotor activity, increased reaction to sound, piloerection, and stained fur. Increased locomotor activity and increased body tone were predominantly but not exclusively observed within the first 1 to 2 weeks of dosing, increased reaction to sound was observed sporadically throughout the dosing phase whereas piloerection and stained fur were observed throughout the on-dose phase. When administration of Compound 1 (3 mg/kg p.o. b.i.d.) was terminated, the only new behaviors observed were teeth chattering with low incidence on 4 days (pm) and stained nose, also with low incidence. In addition, relative to the end of the on-dose phase (Days 42-46 am), increases in hunched posture, increased locomotor activity, piloerection and stained fur were observed during the withdrawal period. Compared to vehicle, during the withdrawal period, there was an increased incidence of hunched posture, rearing, increased reaction to sound, piloerection, teeth chattering, stained fur and stained nose, a decreased incidence of escape attempts from the cage, and increased locomotor activity. Compound 1 (10 mg/kg p.o. b.i.d.) was associated with an initial body weight loss over the first 4 days of the dosing period which resulted in significantly lower daily body weight compared to vehicle-treated controls on the majority of days of dosing up to Day 36. At the end of the on-dose phase, body weights of the rats were −2.6% lower than vehicle control group (p=0.088). Compound 1 (10 mg/kg p.o. b.i.d.) was associated with significantly lower daily food intake during Week 1 (Days 2, 3, 7) and sporadically thereafter (Days 8, 11, 12, 13, 23 and 45 (range −11.2% to −25.9% Week 1 and range −8.0% to −14.5% Weeks 2-6). This was reflected in a lower average weekly food intake during Weeks 1 to 4 and overall. Compound 1 (10 mg/kg p.o. b.i.d.) was also associated with significantly lower daily water intake (Days 1, 9, 11, 13, 15 and 23). This effect was limited to Weeks 1 and 2 as demonstrated when data were analyzed as weekly or overall. No effects on body temperature were observed during the dosing phase. Following abrupt cessation of Compound 1 (10 mg/kg p.o. b.i.d.) daily body weights on Days 1 to 7 of withdrawal (Days 47 to 53) were lower but not significantly different from the vehicle group and slowly returned to vehicle control levels. When body weight was expressed as cumulative change in body weight (difference from Day 46) during the seven-day withdrawal phase, progressive increases in cumulative body weight gain from Day 46 to Day 53), likely representing a reversal of the Compound 1-related decrease in body weight/body weight gain observed during the dosing period were observed, reaching statistical significance on Day 53. Daily food intake remained significantly lower on Day 1 of withdrawal (Day 47) and then increased above control levels on Day 4 and 7 (Days 50 and 53). When food intake was analyzed as daily change in food intake during withdrawal (difference from mean of Days 42 to 46) there was a significant decrease on Days 1 and 5 of withdrawal (Days 47 and 51) and increases on Days 4 and 7 (Days 50 and 53). However, the effect on Day 51 is not considered to be representative of a drug related withdrawal effect since similar decreases were observed across all dose groups on this day. As a result, during withdrawal it is considered that there is an initial decrease in food intake followed by a gradual increase in food intake towards the end of the withdrawal phase. This increase likely reflects a reversal of Compound 1 related decreased food intake during the dosing phase. Significantly higher daily water intakes were observed throughout the withdrawal period (Days 47 to 53) and on Days 47 to 53 (Days 1 to 7 of withdrawal) when data are expressed as daily changes in water intake (when compared to the last 5 days of dosing). An isolated significantly lower daily change in body temperature was observed on Day 3 of withdrawal (Day 49) only when the data were analyzed as difference from mean body temperature during the last 5 days of dosing (Days 42 to 46); daily body temperature was not altered during withdrawal relative to vehicle. Clear behavioral and physical signs were observed with low to high incidence during dosing, including hunched posture, piloerection, drooping abdomen, increased body tone, increased locomotor activity, increased reaction to sound, and stained fur. Upon cessation of Compound 1 (10 mg/kg p.o. b.i.d.) dosing five new behaviors and physical signs were observed with low incidence, tremors (Day 48 pm; 2 rats), ptosis (Days 47 pm, 48 pm and 49 pm; 2-3 rats), erratic respiration (Days 47 pm and 49 pm; 2 rats). teeth chattering (Days 47 pm, 49 pm and 51 pm; 2 rats) and stained nose (Days 46 pm, 47 pm, 48 pm, 49 pm-51 am, and 53 am/pm; 2-3 rats). In addition, relative to the end of the on-dose phase (Days 42-46 am), increases in the incidence of rearing, escape attempts from cage and increased locomotor activity were observed during the withdrawal period. There was also a decreased incidence, relative to the end of the on-dose phase, of drooping abdomen, hunched posture, increased reaction to sound and piloerection. Compared to vehicle, there was an increased incidence during the withdrawal phase of drooping abdomen, hunched posture, rearing, teeth chattering, tremors, increased reaction to sound, piloerection, increased body tone, ptosis, erratic or increased respiration, increased locomotor activity, stained fur and stained nose and a decreased incidence of escape attempts from cage.

Diazepam was administered using a dose-escalation regimen (10/15/20 mg/kg p.o. b.i.d. on Days 1-5/6-18/19-46). Diazepam had no effect on daily body weight from Days 1 to 18 but significantly increased this parameter from Days 19 to 46 when compared to the vehicle-treated controls. This was reflected in significantly higher body weight gain over the entire dosing period. At the end of the doing phase, the weight of the rats dosed with diazepam were 5.4% greater than those that received vehicle. This increase in body weight was associated significantly higher food intake on most days from Day 7 onward, average daily food intake during Weeks 2 to 5, Days 36-45 and overall daily food intake during the on-dose phase, but there was no effect on water intake. Diazepam administration also resulted in higher daily body temperature throughout the on-dose phase reaching statistical significance on Days 2 to 4, 7, 12, 28 to 31, 33 to 35, 37, 38, 40, 41 and 44. This was reflected in a significantly higher average body temperature during Weeks 1, 4, 5 and Days 36 to 46 and overall during the on-dose phase. Upon withdrawal of diazepam administration, daily body weight losses or lower body weight gains, were noted along with decreased food consumption, water intake, and body temperature (relative to the dosing period), which in the case of food and water intake were particularly marked on the first day of withdrawal and abated over the withdrawal phase. Clear behavioral and physical signs were observed with low to high incidence during diazepam administration, including ataxia/rolling gait, hunched posture, high stepping gait, subdued behavior, rearing, escape attempts from the cage, increased body tone, decreased body tone, increased locomotor activity, increased reaction to sound, and stained fur. Low incidence behaviors also included jumping, decreased locomotor activity, exophthalmos, erratic respiration, decreased respiration, and vacuous chewing movements. The incidence of many behavioral and physical signs noted quickly returned to control levels upon withdrawal or markedly declined during the withdrawal phase. However, drooping abdomen, increased respiration and stained nose were observed, albeit at low to moderate incidence, which had not been observed during the on-dose phase. In addition, relative to the end of the on-dose phase (Days 42-46 am), increases in the incidence of rearing, increased body tone, increased reaction to sound, piloerection, stained fur and high stepping were observed during the withdrawal period. There was also a decreased incidence, relative to the end of the on-dose phase, of ataxia/rolling gate, hunched posture, jumping, escape attempts from the cage, increased locomotor activity, decreased respiration and vacuous chewing. Compared to vehicle, there was an increased incidence during the withdrawal phase of drooping abdomen, hunched posture, high stepping, rearing, decreased locomotor activity, erratic or increased respiration, increased reaction to sound, piloerection, increased body tone, stained fur and stained nose. In addition, there was a decrease in observations of increased locomotor activity and escape attempts from cage. All of the dose formulation samples were within the acceptance criteria of ±10%. Maximum concentrations (Cmax) on Day 1, 23 and 46 of 534, 490 and 520 ng/ml were achieved at 3 mg/kg p.o. b.i.d. and 1390, 1690 and 1940 ng/ml were achieved at 10 mg/kg p.o. b.i.d., respectively. The doses of Compound 1 of 3 and 10 mg/kg p.o. b.i.d. for this study achieved exposures which were to 1.14 to 1.23 and 3.23 to 4.50 times greater, respectively, than the human drug exposure at its clinically effective dose (100 mg dose, Cmax=431 ng/ml; Compound 1 Investigators Brochure, version 9.0).

Conclusions: This study complies with the accepted criteria for the determination of the potential to induce a syndrome of physical dependence, including an adequate duration of dosing, abrupt discontinuation of dosing, and frequent monitoring for several days following dose withdrawal (CHMP/EMA, 2006; CDER/FDA, 2017). Following cessation of dosing for 46 days, the typical pattern of diazepam withdrawal signs, including hypophagia and hypodipsia, were observed. Physical dependence was demonstrated by the changes in the incidence, or the appearance of, many behavioral and physical signs following abrupt cessation of dosing, compared to vehicle. Cessation of dosing with Compound 1 (3 mg/kg p.o. b.i.d.) on day 46 resulted in changes in the incidence of behaviors and physical signs suggestive of withdrawal (hyperdipsia, hunched posture, rearing. increased reaction to sound, piloerection, teeth chattering, stained fur, stained nose and escape attempts from cage). There was also evidence of withdrawal following cessation of dosing with Compound 1 (10 mg/kg p.o. b.i.d.) demonstrated by transient hypophagia, hyperdipsia, and changes in the incidence of behaviors and physical signs suggestive of withdrawal (drooping abdomen, rearing, increased locomotor activity, increased reaction to sound, teeth chattering, tremors, ptosis, piloerection, hunched posture, stained fur, stained nose, increased body tone, escape attempts from cage, and erratic or increased respiration).

In summary, cessation of dosing following 46-days administration of Compound 1 at either 3 or 10 mg/kg p.o. b.i.d. resulted in a dose-dependent increase in some withdrawal signs indicative of physical dependence. However, the incidence and severity of the physiological effects and physical signs during withdrawal from Compound 1 was different to that observed during the withdrawal phase for diazepam (10/15/20 mg/kg p.o. b.i.d.), suggesting a distinct, milder withdrawal syndrome.

Various preferred embodiments [A] to [CB] of the invention are described in the text below:

[Embodiment A] A method of treating a neurological or psychiatric disease or disorder, in a patient in need thereof, without causing a clinically significant risk of adverse events, comprising administering to the patient a therapeutically effective amount of Compound 1

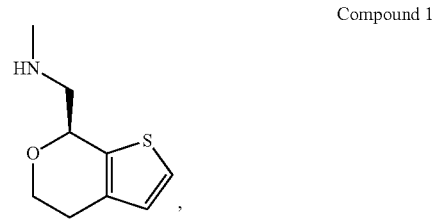

or a pharmaceutically acceptable salt thereof, wherein the patient does not experience a clinically significant adverse event.

[Embodiment B] A method of treating a neurological or psychiatric disease or disorder, in a patient in need thereof, without causing a clinically significant risk of adverse events, comprising administering to the patient a therapeutically effective amount of Compound 1

Compound 1

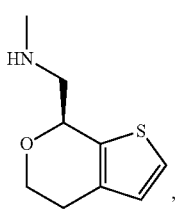

or a pharmaceutically acceptable salt thereof.

[Embodiment C] A method of treating a patient having a neurological or psychiatric disease or disorder without causing a clinically significant risk of adverse events, comprising administering to the patient a therapeutically effective amount of Compound 1 or a pharmaceutically acceptable salt thereof.

Compound 1

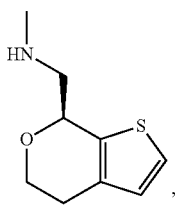

[Embodiment D] A method of treating schizophrenia, in a patient in need thereof, without causing a clinically significant risk of adverse events, comprising administering to the patient a therapeutically effective amount of Compound 1
or a pharmaceutically acceptable salt thereof.

Compound 1

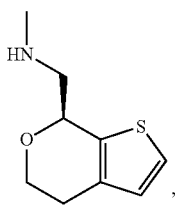

[Embodiment E] A method of treating a patient having schizophrenia without causing a clinically significant risk of adverse events, comprising administering to the patient a therapeutically effective amount of Compound 1
or a pharmaceutically acceptable salt thereof.

Compound 1

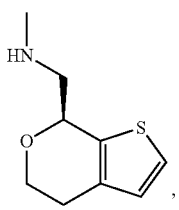

[Embodiment F] A method of treating a neurological or psychiatric disease or disorder in a patient, comprising administering to the patient a therapeutically effective amount of Compound 1

Compound 1

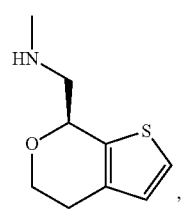

or a pharmaceutically acceptable salt thereof, wherein the method minimizes adverse events associated with antipsychotic agents with affinity to dopamine D2 in the patient.

[Embodiment G] A method of treating a neurological or psychiatric disease or disorder in a patient, comprising administering to the patient a therapeutically effective amount of an antipsychotic agent with no direct affinity to dopamine D2 receptors, wherein the method is substantially devoid of adverse events in the patient, wherein the adverse events are associated with antipsychotic agents with affinity to dopamine D2.

[Embodiment H] A method of Embodiment [G] above, or according to other embodiments of the invention, wherein the antipsychotic agent with no direct affinity to dopamine D2 receptors is Compound 1
or a pharmaceutically acceptable salt thereof.

Compound 1

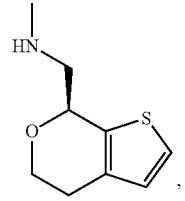

[Embodiment I] A method of minimizing adverse events in a patient in need of treatment for a neurological or psychiatric disease or disorder, the method comprising administering to the patient a therapeutically effective amount of an antipsychotic agent with no direct affinity to dopamine D2 receptors, wherein the antipsychotic agent is Compound 1

Compound 1

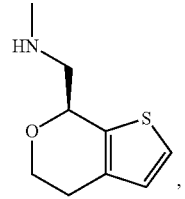

or a pharmaceutically acceptable salt thereof, and wherein the method minimizes adverse events associated with antipsychotic agents with affinity to dopamine D2 receptors.

[Embodiment J] A method of any one of Embodiments [A] to [I] above, or according to other embodiments of the invention, wherein the neurological or psychiatric disease or disorder is schizophrenia.

[Embodiment K] A method of Embodiment [J] above, or according to other embodiments of the invention, further comprising treating negative symptoms of schizophrenia.

[Embodiment L] A method of any one of Embodiments [A] to [I] above, or according to other embodiments of the invention, wherein the neurological or psychiatric disease or disorder is schizophrenia, cognitive impairment associated with schizophrenia, schizophrenia spectrum disorder, schizophrenia negative symptoms, attenuated psychosis syndrome, prodromal schizophrenia, delusional disorder, psychosis, psychotic disorder, delirium, Tourette's syndrome, anxiety and related disorders including general anxiety disorder (GAD) and post-traumatic stress disorder, behavior disorder, affective disorder, depression, major depressive disorder, dysthymia, mood disorders including bipolar disorder, bipolar depression, treatment-resistant depression (TRD), and major depressive disorder (MDD); manic disorder, seasonal affective disorder, obsessive-compulsive disorder, narcolepsy, REM behavior disorder, substance abuse or dependency, Lesch-Nyhan disease, Wilson's disease, autism spectrum disorder, neurodegenerative disorders including dementia, dementia related psychosis (DRP), Parkinson's disease psychosis (PDP), and Alzheimer's disease agitation and psychosis, or Huntington's chorea.

[Embodiment M] A method of any one of Embodiments [A] to [J] or [L] above, or according to other embodiments of the invention, wherein said neurological or psychiatric disease or disorder is selected from schizophrenia, attenuated psychosis syndrome, prodromal schizophrenia, schizoid personality disorder, and schizotypal personality disorder.

[Embodiment N] A method of Embodiment [L] above, or according to other embodiments of the invention, wherein said psychosis is selected from organic psychosis, drug-induced psychosis, Parkinson's disease psychosis, and excitative psychosis.

[Embodiment O] A method of any one of Embodiments [A] to [N] above, or according to other embodiments of the invention, wherein the patient fails to respond adequately to antipsychotic agents which are at least one typical antipsychotic agent or at least one atypical antipsychotic agent.

[Embodiment P] A method of any one of Embodiments [A] to [O] above, or according to other embodiments of the invention, wherein Compound 1, or a pharmaceutically acceptable salt thereof, comprises an HCl salt of Compound 1.

[Embodiment Q] A method of any one of Embodiments [A] to [P] above, or according to other embodiments of the invention, wherein Compound 1, or a pharmaceutically acceptable salt thereof, is administered orally.

[Embodiment R] A method of any one of Embodiments [A] to [Q] above, or according to other embodiments of the invention, wherein Compound 1, or a pharmaceutically acceptable salt thereof, is administered daily in the evening or at night, or at about bedtime.

[Embodiment S] A method of any one of Embodiments [A] to [R] above, or according to other embodiments of the invention, wherein Compound 1, or a pharmaceutically acceptable salt thereof, is administered at about 50 mg or about 75 mg per day.

[Embodiment T] A method of any one of Embodiments [A] to [S] above, or according to other embodiments of the invention, wherein Compound 1, or a pharmaceutically acceptable salt thereof, is administered daily during a 4-week treatment period.

[Embodiment U] A method of any one of Embodiments [A] to [S] above, or according to other embodiments of the invention, wherein Compound 1, or a pharmaceutically acceptable salt thereof, is administered daily during a 26-week treatment period.

[Embodiment V] A method of any one of Embodiments [A] to [U] above, or according to other embodiments of the invention, wherein a risk of adverse events in the patient is about the same as or similar to placebo.

[Embodiment W] A method of any one of Embodiments [A] to [V] above, or according to other embodiments of the invention, wherein the method minimizes cardiovascular adverse events.

[Embodiment X] A method of any one of Embodiments [A] to [W] above, or according to other embodiments of the invention, wherein the method results in a cardiovascular event in less than or equal to 5% of patients.

[Embodiment Y] A method of any one of Embodiments [A] to [W] above, or according to other embodiments of the invention, wherein the patient has an elevated risk of a cardiovascular adverse event from administration of an antipsychotic agent.

[Embodiment Z] A method of Embodiment [T] above, or according to other embodiments of the invention, wherein the method results in a cardiovascular adverse event in less than or equal to 5% of patients during the 29-day treatment period.

[Embodiment AA] A method of Embodiment [U] above, or according to other embodiments of the invention, wherein the method results in a cardiovascular adverse event in less than or equal to 6% of patients during the 26-week treatment period.

[Embodiment AB] A method of any one of Embodiments [A] to [V] above, or according to other embodiments of the invention, wherein the method results in a cardiovascular adverse event in a percentage of patients that is about the same as or similar to placebo.

[Embodiment AC] A method of any one of Embodiments [W] to [AB] above, or according to other embodiments of the invention, wherein a cardiovascular adverse event is characterized as atrial tachycardia, bradycardia, cardiovascular insufficiency, palpitations, postural tachycardia syndrome, increased blood pressure, hypertension, hypotension, hot flush, QT prolongation, orthostatic hypotension, or orthostatic tachycardia.

[Embodiment AD] A method of any one of Embodiments [A] to [V] above, or according to other embodiments of the invention, wherein the method minimizes extrapyramidal adverse events.

[Embodiment AE] A method of any one of Embodiments [A] to [V] or [AD] above, or according to other embodiments of the invention, wherein the method results in an extrapyramidal adverse event in less than or equal to 5% of patients.

[Embodiment AF] A method of any one of Embodiments [A] to [V] or [AD] above, or according to other embodiments of the invention, wherein the patient has an elevated risk of an extrapyramidal adverse event from administration of an antipsychotic agent.

[Embodiment AG] A method of any one of Embodiments [AD] to [AF] above, or according to other embodiments of the invention, wherein an extrapyramidal adverse event is characterized as akathisia, restlessness, joint stiffness, musculoskeletal stiffness, nuchal rigidity, postural tremor, or tremor.

[Embodiment AH] A method of any one of Embodiments [A] to [V] above, or according to other embodiments of the invention, wherein the method results in an extrapyramidal adverse event in a percentage of patients that is no more than placebo.

[Embodiment AI] A method of any one of Embodiments [A] to [V] above, or according to other embodiments of the invention, wherein the method is substantially devoid of QT prolongation.

[Embodiment AJ] A method of any one of Embodiments [A] to [V] or [AI] above, or according to other embodiments of the invention, wherein the method results in QT prolongation in less than or equal to 5% of patients.

[Embodiment AK] A method of any one of Embodiments [A] to [V] or [AI] above, or according to other embodiments of the invention, wherein the patient has an elevated risk of QT prolongation from administration of an antipsychotic agent.

[Embodiment AL] A method of Embodiment [T] above, or according to other embodiments of the invention, wherein the method is substantially devoid of QT prolongation during the 29-day treatment period.

[Embodiment AM] A method of any one of Embodiments [A] to [V] above, or according to other embodiments of the invention, wherein the method results in QT prolongation in a percentage of patients that is no more than placebo.

[Embodiment AN] A method of any one of Embodiments [AI] to [AM] above, or according to other embodiments of the invention, wherein QT prolongation is characterized as one or both of:
  a QTcF interval in the patient of greater than 450 msec at any time point not present at baseline; and
  an increase in QTcF interval from baseline of greater than or equal to 30 msec for at least one post-baseline measurement.

[Embodiment AO] A method of any one of Embodiments [A] to [V] above, or according to other embodiments of the invention, wherein the method minimizes hyperprolactinemia in the patient.

[Embodiment AP] A method of any one of Embodiments [A] to [V] above, or according to other embodiments of the invention, wherein the method results in hyperprolactinemia in a percentage of patients that is no more than placebo.

[Embodiment AQ] A method of any one of Embodiments [A] to [V] above, or according to other embodiments of the invention, wherein the method minimizes orthostatic hypotension in the patient.

[Embodiment AR] A method of any one of Embodiments [A] to [V] or [AQ] above, or according to other embodiments of the invention, wherein the method results in orthostatic hypotension in less than or equal to 5% of patients.

[Embodiment AS] A method of any one of Embodiments [A] to [V] or [AQ] above, or according to other embodiments of the invention, wherein the patient has an elevated risk of orthostatic hypotension from administration of an antipsychotic agent.

[Embodiment AT] A method of any one of Embodiments [A] to [V] above, or according to other embodiments of the invention, wherein the method results in orthostatic hypotension in a percentage of patients that is no more than placebo.

[Embodiment AU] A method of any one of Embodiments [A] to [V] above, or according to other embodiments of the invention, wherein the method minimizes orthostatic tachycardia in the patient.

[Embodiment AV] A method of any one of Embodiments [A] to [V] or [AU] above, or according to other embodiments of the invention, wherein the method results in orthostatic tachycardia in less than or equal to 5% of patients.

[Embodiment AW] A method of any one of Embodiments [A] to [V] or [AU] above, or according to other embodiments of the invention, wherein the patient has an elevated risk of orthostatic tachycardia from administration of an antipsychotic agent.

[Embodiment AX] A method of any one of Embodiments [A] to [V] above, or according to other embodiments of the invention, wherein the method results in orthostatic tachycardia in a percentage of patients that is about the same as or similar to placebo.

[Embodiment AY] A method of any one of Embodiments [A] to [AX] above, or according to other embodiments of the invention, wherein the method results in (i) a reduction from baseline in PANSS total score of at least 17.2 or (ii) an effect size in PANSS total score of at least 0.45.

[Embodiment AZ] A method of Embodiment [AY] above, or according to other embodiments of the invention, wherein the result is measured after 29 days of treatment.

[Embodiment BA] A method of any one of Embodiments [AX] or [AY] above, or according to other embodiments of the invention, wherein the method results in a reduction from baseline in PANSS total score of at least about 30 after 30 weeks of treatment.

[Embodiment BB] A method of any one of Embodiments [A] to [BA] above, or according to other embodiments of the invention, wherein the method results in (i) a reduction from baseline in PANSS positive subscale score of at least 5.5 or (ii) an effect size in PANSS positive subscale score of at least 0.32.

[Embodiment BC] A method of Embodiment [BB] above, or according to other embodiments of the invention, wherein the result is measured after 29 days of treatment.

[Embodiment BD] A method of any one of Embodiments [BB] or [BC] above, or according to other embodiments of the invention, wherein the method results in a reduction from baseline in PANSS positive subscale score of at least about 10 after 30 weeks of treatment.

[Embodiment BE] A method of any one of Embodiments [A] to [BD] above, or according to other embodiments of the invention, wherein the method results in (i) a reduction from baseline in PANSS negative subscale score of at least 3.1 or (ii) an effect size in PANSS negative subscale score of at least 0.37.

[Embodiment BF] A method of Embodiment [BE] above, or according to other embodiments of the invention, wherein the result is measured after 29 days of treatment.

[Embodiment BG] A method of any one of Embodiments [BE] or [BF] above, or according to other embodiments of the invention, wherein the method results in a reduction from baseline in PANSS negative subscale score of at least about 5 after 30 weeks of treatment.

[Embodiment BH] A method of any one of Embodiments [A] to [BG] above, or according to other embodiments of the invention, wherein the method results in (i) a reduction from baseline in PANSS general psychopathology subscale score of at least 9 or (ii) an effect size in PANSS general psychopathology subscale score of at least 0.51.

[Embodiment BI] A method of Embodiment [BH] above, or according to other embodiments of the invention, wherein the result is measured after 29 days of treatment.

[Embodiment BJ] A method of any one of Embodiments [BH] or [BI] above, or according to other embodiments of the invention, wherein the method results in a reduction from baseline in PANSS general psychopathology subscale score of at least about 15 after 30 weeks of treatment.

[Embodiment BK] A method of any one of Embodiments [A] to [BJ] above, or according to other embodiments of the invention, wherein the method results in (i) a reduction from baseline in CGI-S score of at least 1 or (ii) an effect size in CGI-S score of at least 0.52.

[Embodiment BL] A method of Embodiment [BK] above, or according to other embodiments of the invention, wherein the result is measured after 29 days of treatment.

[Embodiment BM] A method of any one of Embodiments [BK] or [BL] above, or according to other embodiments of the invention, wherein the method results in a reduction from baseline in CGI-S score of at least about 1.5 after 30 weeks of treatment.

[Embodiment BN] A method of any one of Embodiments [A] to [BM] above, or according to other embodiments of the invention, wherein the method results in (i) a reduction from baseline in BNSS total score of at least 7.1 or (ii) an effect size in BNSS total score of at least 0.48.

[Embodiment BO] A method of Embodiment [BN] above, or according to other embodiments of the invention, wherein the result is measured after 29 days of treatment.

[Embodiment BP] A method of any one of Embodiments [BN] or [BO] above, or according to other embodiments of the invention, wherein the method results in a reduction from baseline in BNSS total score of at least about 10 after 30 weeks of treatment.

[Embodiment BQ] A method of any one of Embodiments [A] to [BP] above, or according to other embodiments of the invention, wherein the method results in (i) a reduction from baseline in MADRS total score of at least 3.3 or (ii) an effect size in MADRS total score of at least 0.32.

[Embodiment BR] A method of Embodiment [BQ] above, or according to other embodiments of the invention, wherein the result is measured after 29 days of treatment.

[Embodiment BS] A method of any one of Embodiments [BQ] or [BR] above, or according to other embodiments of the invention, wherein the method results in a reduction from baseline in MADRS total score of at least about 5 after 30 weeks of treatment.

[Embodiment BT] A method of any one of Embodiments [A] to [V] above, or according to other embodiments of the invention, comprising treating a symptom of insomnia, anxiety, or headache in the patient.

[Embodiment BU] A method of any one of Embodiments [A] to [V] above, or according to other embodiments of the invention, wherein the method minimizes insomnia, anxiety, headache or any combination thereof in the patient.

[Embodiment BV] A method of any one of Embodiments [BT] or [BU] above, or according to other embodiments of the invention, wherein the risk of insomnia, anxiety, headache, or any combination thereof in the patient is less than placebo.

[Embodiment BW] A method of any one of Embodiments [A] to [BV] above, or according to other embodiments of the invention, wherein Compound 1, or a pharmaceutically acceptable salt thereof, is administered orally and daily at a first dose for 1 to 3 days, followed by administering to the patient Compound 1, or a pharmaceutically acceptable salt thereof, daily at a therapeutic dose, wherein the first dose is less than the therapeutic dose, wherein the neurological or psychiatric disease or disorder is schizophrenia.

[Embodiment BX] A method of any one of Embodiments [A] to [BW] above, or according to other embodiments of the invention, wherein Compound 1, or a pharmaceutically acceptable salt thereof, is administered daily at the first dose on days 1-3, and Compound 1, or a pharmaceutically acceptable salt thereof, is administered daily at the therapeutic dose on days 4-29.

[Embodiment BY] A method of any one of Embodiments [BW] or [BX] above, or according to other embodiments of the invention, wherein the first dose is 50 mg and the therapeutic dose is 75 mg.

[Embodiment BZ] A method of treating schizophrenia in a patient, comprising:
orally administering or having administered to the patient 75 mg daily of Compound 1

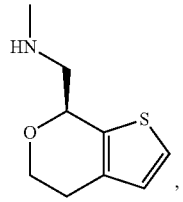

Compound 1 or a pharmaceutically acceptable salt thereof, during a treatment period;
determining or having determined if the patient has experienced an adverse event during the treatment period; and
reducing or having reduced administration to 50 mg daily of Compound 1, or a pharmaceutically acceptable salt thereof, if the patient experiences an adverse event during the treatment period.

[Embodiment CA] A method of treating a symptom of insomnia, anxiety, or headache, in a patient having schizophrenia, comprising administering to the patient a therapeutically effective amount of Compound 1

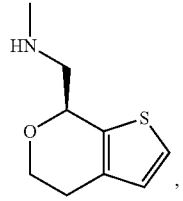

Compound 1 or a pharmaceutically acceptable salt thereof.

[Embodiment CB] A method of any one of Embodiments [A] to [CA] above, or according to other embodiments of the invention, wherein Compound 1, or a pharmaceutically acceptable salt thereof, is Compound 1 hydrochloride of crystalline Form A.

[Embodiment CC] A method for preparing (S)-(4,5-dihydro-7H-thieno[2,3-c]pyran-7-yl)-N-methylmethanamine hydrochloride crystalline Form A comprising the sequential steps of:

(c) dissolving 4,5-dihydro-7H-thieno[2,3-c]pyran-7-yl)-N-methylmethanamine free base in acetonitrile to provide a 25%-35% solution by weight and adding said solution to a 15-20% (weight-to-weight) solution of (R)-mandelic acid in acetone at 40-55° C., cooling to 10-25° C., and filtering off (S)-(−)-4,5-dihydro-7H-thieno[2,3-c]pyran-7-yl)-N-methylmethanamine (R) mandelate;

(d) reacting said (S)-(−)-4,5-dihydro-7H-thieno[2,3-c]pyran-7-yl)-N-methylmethanamine (R) mandelate with an excess of aqueous base to provide (S)-4,5-dihydro-7H-thieno[2,3-c]pyran-7-yl)-N-methylmethanamine free base; and (e) dissolving said (S)-4,5-dihydro-7H-thieno[2,3-c]pyran-7-yl)-N-methylmethanamine free base to a concentration of 6-10% by weight in isopropyl alcohol, adding 6% HCl (w/w) solution in isopropanol at a rate chosen to minimize supersaturation, holding the mixture at 35-45° C. for a period of 15 to 60 minutes, cooling to 15-25° C., and filtering off (S)-(4,5-dihydro-7H-thieno[2,3-c]pyran-7-yl)-N-methylmethanamine hydrochloride crystalline Form A.

[Embodiment CD] A method of Embodiment [CC] above, or according to other embodiments of the invention, wherein 4,5-dihydro-7H-thieno[2,3-c]pyran-7-yl)-N-methylmethanamine free base is prepared by the sequential steps of:
(a) reacting 3-thiopheneethanol with N-methylaminoacetaldehyde dimethyl acetal in the presence of trifluoromethanesulfonic acid to provide 4,5-dihydro-7H-thieno[2,3-c]pyran-7-yl)-N-methylmethanamine triflate; and
(b) reacting said 4,5-dihydro-7H-thieno[2,3-c]pyran-7-yl)-N-methylmethanamine triflate with an excess of aqueous base to provide 4,5-dihydro-7H-thieno[2,3-c]pyran-7-yl)-N-methylmethanamine free base.

[Embodiment CE] Compound 1 hydrochloride crystalline Form A prepared by the method of Embodiment [CC] or Embodiment [CD], or according to other embodiments of the invention.

[Embodiment CF] A method of any one of Embodiments [A] to [CB] above, or according to other embodiments of the invention, further comprising administering Compound 1, or a pharmaceutically acceptable salt thereof, in conjunction with one or more pharmaceutical agents.

[Embodiment CG] A method of Embodiment [CF], or according to other embodiments of the invention, wherein the one or more pharmaceutical agents are anti-Parkinson's drugs, anti-Alzheimer's drugs, anti-depressants, anti-psychotics, anti-ischemics, CNS depressants, anti-cholinergics, nootropics, epilepsy medication, attention (e.g., ADD/ADHD) medications, sleep-promoting medications, wakefulness-promoting medications, or pain medications.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

We claim:
1. A method of treating a neurological or psychiatric disease or disorder without decreasing sleep quality in a human patient in need thereof, comprising once daily orally administering to the patient a therapeutically effective amount of from 25 to 100 mg of Compound 1

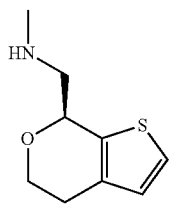

Compound 1 or a pharmaceutically acceptable salt thereof at about bedtime.

2. The method of claim 1, wherein the therapeutically effective amount comprises from 25 to 75 mg.

3. The method of claim 1, wherein the neurological or psychiatric disease or disorder is selected from schizophrenia, depression, and anxiety.

4. The method of claim 1, wherein the administration produces a $C_{trough}$ of 7.97-31.5 ng/mL after multiple administrations.

5. The method of claim 1, wherein the administration produces a $t_{max}$ of 2.0-4.0 hours after single or multiple administrations.

6. The method of claim 1, for treating the neurological or psychiatric disease or disorder in the patient continuously for a period of 6 months or more, comprising administering the therapeutically effective amount for 6 months or more.

7. A method of treating a neurological or psychiatric disease or disorder, in a human patient in need thereof, comprising once-daily administering to the patient a therapeutically effective amount of Compound 1

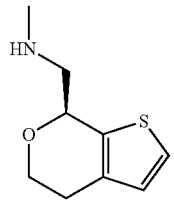

Compound 1 or a pharmaceutically acceptable salt thereof at about bedtime, so as to produce a $t_{max}$ of 2.0-4.0 hours after single or multiple administrations.

8. The method of claim 7, wherein the neurological or psychiatric disease or disorder is selected from schizophrenia, depression, and anxiety.

9. The method of claim 7, wherein the therapeutically effective amount comprises from 25 to 75 mg.

10. The method of claim 7, wherein the administration produces a $C_{trough}$ of 7.97-31.5 ng/mL after multiple administrations.

11. The method of claim 7, for treating the neurological or psychiatric disease or disorder in the patient continuously for a period of 6 months or more, comprising administering the therapeutically effective amount for 6 months or more.

12. The method of claim 7, wherein the neurologic or psychiatric disease or disorder is schizophrenia in a patient having a PANSS total score <80.

13. The method of claim 7, wherein the neurologic or psychiatric disease or disorder is depression.

14. The method of claim 7, wherein the neurologic or psychiatric disease or disorder is anxiety.

15. The method of claim 11, wherein the neurologic or psychiatric disease or disorder is schizophrenia in a patient having a PANSS total score <80.

16. The method of claim 11, wherein the neurologic or psychiatric disease or disorder is depression.

17. The method of claim 11, wherein the neurologic or psychiatric disease or disorder is anxiety.

18. A method of treating a neurological or psychiatric disease or disorder, in a human patient in need thereof, comprising once-daily administering to the patient a therapeutically effective amount of Compound 1

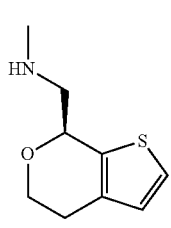

Compound 1 or a pharmaceutically acceptable salt thereof at about bedtime, so as to produce a $C_{trough}$ of 7.97-31.5 ng/mL after multiple administrations.

19. The method of claim 18, wherein the neurological or psychiatric disease or disorder is selected from schizophrenia, depression, and anxiety.

20. The method of claim 18, wherein the therapeutically effective amount comprises from 25 to 75 mg.

21. The method of claim 18, for treating the neurological or psychiatric disease or disorder in the patient continuously for a period of 6 months or more, comprising administering the therapeutically effective amount for 6 months or more.

* * * * *